United States Patent
Blackaby et al.

(10) Patent No.: US 7,030,128 B2
(45) Date of Patent: Apr. 18, 2006

(54) IMIDAZO-PYRIMIDINE DERIVATIVES AS LIGANDS FOR GABA RECEPTORS

(75) Inventors: Wesley Peter Blackaby, Buckhurst Hill (GB); Jose Luis Castro Pineiro, Bishops Stortford (GB); Mark Stuart Chambers, Puckeridge (GB); Simon Charles Goodacre, Benington (GB); David James Hallett, Watford (GB); Philip Jones, Pomezia (IT); Richard Thomas Lewis, Bishops Stortford (GB); Angus Murray MacLeod, Bishops Stortford (GB); Robert James Maxey, Amersham (GB); Kevin William Moore, Buntingford (GB); Leslie Joseph Street, Little Hallingbury (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 140 days.

(21) Appl. No.: 10/472,680

(22) PCT Filed: Mar. 19, 2002

(86) PCT No.: PCT/GB02/01354

§ 371 (c)(1),
(2), (4) Date: Sep. 19, 2003

(87) PCT Pub. No.: WO02/076983

PCT Pub. Date: Oct. 3, 2002

(65) Prior Publication Data

US 2004/0092533 A1 May 13, 2004

(30) Foreign Application Priority Data

Mar. 23, 2001 (GB) .............................................. 0107358
Nov. 23, 2001 (GB) .............................................. 0128157

(51) Int. Cl.
*A61K 31/519* (2006.01)
*C07D 487/04* (2006.01)
*A61P 25/22* (2006.01)

(52) U.S. Cl. .............................. 514/259.1; 514/252.01; 514/234.2; 514/255.05; 544/282; 544/122; 544/238

(58) Field of Classification Search ................. 544/282, 544/122, 238; 514/259.1, 252.01, 234.2, 514/255.05
See application file for complete search history.

(56) References Cited

U.S. PATENT DOCUMENTS 5,922,725 A    7/1999   Teuber et al.

FOREIGN PATENT DOCUMENTS

WO    WO 99 19323 A    4/1999
WO    WO 01 64674 A    9/2001

OTHER PUBLICATIONS

Martin I. L. et al: "Benzodiazepine Recognition Site Ligands and Gabaa Receptors" Expert Opinion on Therapeutic Patents, Ashley Publications, GB, vol. 9, No. 10, 1999, pp. 1347–1358.

Tully W. R. et al: "General Approach Leading to the Development of Imidazoquinoline andimidazopyrimidine Benzodiazepine Receptor Ligands" Drug Development Research, New York, NY. US, vol. 22, 1991, pp. 299–308.

*Primary Examiner*—Evelyn Mei Huang
(74) *Attorney, Agent, or Firm*—J. Eric Thies; Melvin Winokur

(57) ABSTRACT

A class of imidazo[1,2-α]pyrimidine derivatives, substituted at the 3-position by an optionally substituted five-membered or six-membered heteroaromatic ring, are selective ligands for $GABA_A$ receptors, in particular having good affinity for the α2 and/or α3 and/or α5 subunit thereof, and are accordingly of benefit in the treatment and/or prevention of adverse conditions of the central nervous system, including anxiety, convulsions and cognitive disorders.

10 Claims, No Drawings

IMIDAZO-PYRIMIDINE DERIVATIVES AS LIGANDS FOR GABA RECEPTORS

CROSS REFERENCE TO RELATED APPLICATIONS

This application is a U.S. National Phase application under 35 U.S.C. § 371 of PCT Application No. PCT/GB02/01354, filed Mar. 19, 2002, which claims priority under 35 U.S.C. § 119 from GB Application No. 0107358.4, filed Mar. 23, 2001, and GB Application No. 0128157.5, filed Nov. 23, 2001.

The present invention relates to a class of substituted imidazo-pyrimidine derivatives and to their use in therapy. More particularly, this invention is concerned with imidazo [1,2-$\alpha$]pyrimidine analogues which are substituted in the 3-position by an optionally substituted heteroaromatic ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta\gamma1$, $\alpha2\beta2/3\gamma2$, $\alpha3\beta\gamma2/3$, $\alpha4\beta\delta$, $\alpha5\beta3\gamma2/3$, $\alpha6\beta\gamma2$ and $\alpha6\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect.

Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Moreover, agents which are inverse agonists of the $\alpha5$ subunit are likely to be beneficial in enhancing cognition, for example in subjects suffering from dementing conditions such as Alzheimer's disease. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for GABA$_A$ receptors may be beneficial in enhancing cognition, for example in subjects suffering from dementing conditions such as Alzheimer's disease; and may also be effective as pre-medication prior to anaesthesia or minor procedures such as endoscopy, including gastric endoscopy.

In addition, the compounds in accordance with the present invention may be useful as radioligands in assays for detecting compounds capable of binding to the human GABA$_A$ receptor.

The present invention provides a class of imidazopyrimidine derivatives which possess desirable binding properties at various GABA$_A$ receptor subtypes. The compounds in accordance with the present invention have good affinity as ligands for the α2 and/or α3 and/or α5 subunit of the human GABA$_A$ receptor. The compounds of this invention may interact more favourably with the α2 and/or α3 subunit than with the α1 subunit; and/or may interact more favourably with the α5 subunit than with the α1 subunit.

The compounds of the present invention are GABA$_A$ receptor subtype ligands having a binding affinity (K$_i$) for the α2 and/or α3 and/or α5 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 and/or α5 subunit relative to the α1 subunit. However, compounds which are not selective in terms of their binding affinity for the α2 and/or α3 and/or α5 subunit relative to the α1 subunit are also encompassed within the scope of the present invention; such compounds will desirably exhibit functional selectivity in terms of zero or weak (positive or negative) efficacy at the α1 subunit and (i) a full or partial agonist profile at the α2 and/or α3 subunit, and/or (ii) an inverse agonist profile at the α5 subunit.

The present invention provides a compound of formula I, or a salt or prodrug thereof:

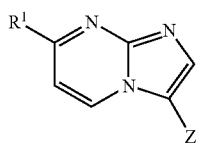

(I)

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and R$^a$ and R$^b$ independently represent hydrogen, hydrocarbon or a heterocyclic group.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z.

Where Z in the compounds of formula I above represents a six-membered heteroaromatic ring, this ring may be optionally substituted by one or more substituents, typically by one or two substituents.

Suitably, the group Z is unsubstituted or monosubstituted.

Examples of optional substituents on the five-membered or six-membered heteroaromatic ring as specified for Z include halogen, cyano, trifluoromethyl, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy(C$_{1-6}$)alkyl, C$_{3-7}$ cycloalkyl, C$_{3-7}$ heterocycloalkyl, benzyltetrahydropyridinyl, C$_{1-6}$ alkoxy, methyltriazolyl(C$_{1-6}$) alkoxy, C$_{1-6}$ alkylthio, C$_{1-6}$ alkylsulphonyl, C$_{2-6}$ alkylcarbonyl, amino, C$_{1-6}$ alkylamino, di(C$_{1-6}$)alkylamino, C$_{2-6}$ alkylcarbonylamino, phenyl, (C$_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, (C$_{2-6}$) alkylcarbonyl-phenyl, trifluorothio-phenyl, (C$_{1-6}$) alkylsulphonyl-phenyl, di(C$_{1-6}$)alkylaminocarbonyl-phenyl, di(C$_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl and optionally substituted heteroaryl, the optional substituents on the heteroaryl moiety being typically selected from oxy, halogen, cyano and C$_{1-6}$ alkyl.

Examples of typical substituents on the five-membered or six-membered ring as specified for Z include halogen, cyano, trifluoromethyl, C$_{1-6}$ alkyl, halo(C$_{1-6}$)alkyl, C$_{1-6}$ alkoxy(C$_{1-6}$)alkyl, C$_{3-7}$ cycloalkyl, C$_{3-7}$ heterocycloalkyl, C$_{1-6}$ alkoxy, methyltriazolyl(C$_{1-6}$)alkoxy, C$_{1-6}$ alkylthio, C$_{1-6}$ alkylsulphonyl, amino, C$_{1-6}$ alkylamino, di(C$_{1-6}$) alkylamino, C$_{2-6}$ alkylcarbonylamino, phenyl, fluorophenyl, chlorophenyl, cyanophenyl, (fluoro)(cyano)phenyl, nitrophenyl, methoxyphenyl, thiadiazolyl-phenyl, methylthiadiazolyl-phenyl, methyltetrazolyl-phenyl and optionally substituted heteroaryl, the optional substituents on the heteroaryl moiety being typically selected from oxy, halogen, cyano and C$_{1-6}$ alkyl.

Examples of suitable substituents on the five-membered or six-membered heteroaromatic ring as specified for Z include halogen, cyano, trifluoromethyl, C$_{1-6}$ alkyl, halo(C$_{1-6}$)alkyl, C$_{3-7}$ cycloalkyl, C$_{3-7}$ heterocycloalkyl, C$_{1-6}$ alkoxy, C$_{1-6}$ alkylthio, amino, C$_{1-6}$ alkylamino, di(C$_{1-6}$)alkylamino, cyanophenyl, methoxyphenyl and heteroaryl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "$C_{1-6}$ alkoxy", "$C_{1-6}$ alkylamino" and "$C_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl($C_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in Design of Prodrugs, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Where the group Z represents an optionally substituted five-membered heteroaromatic ring, this is suitably a thiophene, thiazole or thiadiazole ring, either of which may be optionally substituted by one or, where possible, two substituents.

Where the group Z represents an optionally substituted six-membered heteroaromatic ring, this is suitably a pyridinyl or pyrimidinyl ring, either of which may be optionally substituted by one or more substituents, typically by one or two substituents. In one embodiment, Z represents monosubstituted pyridinyl. In another embodiment, Z represents monosubstituted pyrimidinyl.

Illustrative examples of optional substituents on the group Z include fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, methoxy, ethoxy, isopropoxy, tert-butoxy, methyltriazolyl-methoxy, methylthio, ethylthio, methanesulphonyl, acetyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl)phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Suitable examples of optional substituents on the group Z include fluoro, chloro, bromo, iodo, cyano, trifluoromethyl, methyl, tert-butyl, chloromethyl, methoxymethyl, cyclopentyl, pyrrolidinyl, morpholinyl, methoxy, ethoxy, isopropoxy, tert-butoxy, methyltriazolyl-methoxy, methylthio, ethylthio, methanesulphonyl, tert-butylamino, dimethylamino, acetylamino, phenyl, fluorophenyl, chlorophenyl, cyanophenyl, (cyano)(fluoro)phenyl, nitrophenyl, methoxyphenyl, thiadiazolyl-phenyl, methylthiadiazolyl-phenyl, methyltetrazolyl-phenyl, pyridinyl, oxypyridinyl, chloropyridinyl, cyanopyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Typical examples of optional substituents on the group Z include halogen, cyano, trifluoromethyl, $C_{1-6}$ alkyl, halo($C_{1-6}$)alkyl, $C_{3-7}$ cycloalkyl, $C_{3-7}$ heterocycloalkyl, $C_{1-6}$ alkoxy, cyanophenyl, thienyl and pyridinyl. Examples of specific substituents on the group Z include chloro, bromo, cyano, trifluoromethyl, methyl, chloromethyl, cyclopentyl, pyrrolidinyl (especially pyrrolidin-1-yl), methoxy, cyanophenyl (especially 2-cyanophenyl), thienyl (especially thien-2-yl) and pyridinyl (especially pyridin-3-yl).

One particular substituent on the group Z is cyanophenyl, especially 2-cyanophenyl.

Another particular substituent on the group Z is fluorophenyl.

A preferred substituent on the group Z is difluorophenyl.

Illustrative values of Z include pyridinyl, bromopyridinyl, cyanopyridinyl, trifluoromethyl-pyridinyl, methylpyridinyl, cyclopentylpyridinyl, pyrrolidinyl-pyridinyl, methoxypyridinyl, cyanophenyl-pyridinyl, chloropyrimidinyl, cyanophenyl-pyrimidinyl, pyridinyl-thienyl, thiazolyl, pyridinyl-thiazolyl, chloromethyl-thiadiazolyl and thienyl-thiadiazolyl.

Specific values of Z include pyridin-2-yl, 3-bromopyridin-2-yl, 5-cyanopyridin-2-yl, 5-trifluoromethylpyridin-2-yl, 6-trifluoromethylpyridin-2-yl, 5-methylpyridin-2-yl, 6-methylpyridin-2-yl, 6-cyclopentylpyridin-2-yl, 6-(pyrrolidin-1-yl)pyridin-2-yl, 6-methoxypyridin-2-yl, 6-(2-cyanophenyl)pyridin-2-yl, 2-(2-cyanophenyl)pyridin-4-yl, 2-chloropyrimidin-4-yl, 2-(2-cyanophenyl)pyrimidin-4-yl, 4-(pyridin-3-yl)thien-2-yl, 2-(pyridin-3-yl)thien-4-yl, thiazol-2-yl, 4-(pyridin-3-yl)thiazol-2-yl, 3-chloromethyl-[1,2,4]thiazol-5-yl and 3-(thien-2-yl)-[1,2,4]thiazol-5-yl.

A favoured value of Z is fluorophenyl-pyrimidinyl.

A preferred value of Z is difluorophenyl-pyrimidinyl.

Typically, $R^1$ represents hydrogen, hydrocarbon, a heterocyclic group, halogen, cyano, trifluoromethyl, —$OR^a$, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl, especially hydrogen or dimethylaminoethyl.

Representative values of $R^1$ include hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl and —$CR^a$=$NOR^b$, in which $R^a$ and $R^b$ are as defined above. In addition, $R^1$ may represent cyano($C_{1-6}$)alkyl.

Individual values of $R^1$ include $C_{1-6}$ alkyl, halo($C_{1-6}$)alkyl, cyano($C_{1-6}$)alkyl, hydroxy($C_{1-6}$)alkyl, di($C_{1-6}$)alkoxy($C_{1-6}$)alkyl, heteroaryl($C_{1-6}$)alkyl, trifluoromethyl and $C_{2-6}$ alkylcarbonyl.

Itemised values of $R^1$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, cyclopropyl, cyclobutyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl. In addition, $R^1$ may represent cyanopropyl (especially 2-cyanoprop-2-yl).

Representative values of $R^1$ include dimethoxyethyl (especially 1,1-dimethoxyethyl), cyanopropyl (especially 2-cyanoprop-2-yl), hydroxypropyl (especially 2-hydroxyprop-2-yl), fluoropropyl (especially 2-fluoroprop-2-yl), tert-butyl, triazolylmethyl, trifluoromethyl and acetyl.

A favoured value of $R^1$ is 2-hydroxyprop-2-yl.

A particular value of $R^1$ is trifluoromethyl.

Suitably, $R^2$ is hydrogen.

Suitably, $R^3$ represents hydrogen or dimethylaminoethyl, especially hydrogen.

A particular sub-class of compounds according to the invention is represented by the compounds of formula IA, and salts and prodrugs thereof:

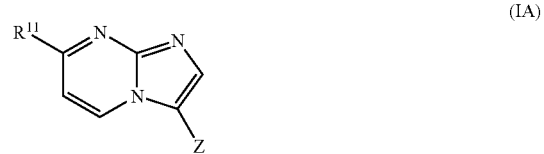

(IA)

wherein

Z is as defined above;

$R^{11}$ represents hydrogen, $C_{1-6}$ alkyl, cyano($C_{1-6}$)alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl or —$CR^4$=$NOR^5$;

$R^4$ represents hydrogen or $C_{1-6}$ alkyl; and $R^5$ represents hydrogen, $C_{1-6}$ alkyl, hydroxy($C_{1-6}$)alkyl or di($C_{1-6}$)alkylamino($C_{1-6}$)alkyl.

The present invention also provides a compound of formula IA as depicted above, or a salt thereof or a prodrug thereof, wherein $R^{11}$ represents hydrogen, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, $C_{3-7}$ cycloalkyl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl or —$CR^4$=$NOR^5$; and Z, $R^4$ and $R^5$ are as defined above.

Suitably, $R^4$ represents hydrogen or methyl, especially hydrogen.

Suitably, $R^5$ represents hydrogen, methyl, ethyl, hydroxyethyl or dimethylaminoethyl. Particular values of $R^5$ include hydrogen, hydroxyethyl and dimethylaminoethyl. Typically, $R^5$ represents hydrogen or dimethylaminoethyl, especially hydrogen.

Where $R^{11}$ represents heteroaryl, this group is suitably pyridinyl, furyl, thienyl or oxazolyl.

Where $R^{11}$ represents $C_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where $R^{11}$ represents heteroaryl($C_{1-6}$)alkyl, this group is suitably imidazolylmethyl or triazolylmethyl.

Itemised values of $R^{11}$ include hydrogen, methyl, fluoromethyl, difluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, cyclopropyl, cyclobutyl, pyridinyl, furyl, thienyl, oxazolyl, methylthiazolyl, methyloxadiazolyl, imidazolylmethyl, triazolylmethyl, chloro, cyano, trifluoromethyl, methoxy, formyl, acetyl, methoxycarbonyl and —$CR^2$=$NOR^3$, in which $R^2$ and $R^3$ are as defined above. In addition, $R^{11}$ may represent cyanopropyl (especially 2-cyanoprop-2-yl).

Representative values of $R^{11}$ include dimethoxyethyl (especially 1,1-dimethoxyethyl), cyanopropyl (especially 2-cyanoprop-2-yl), hydroxypropyl (especially 2-hydroxyprop-2-yl), fluoropropyl (especially 2-fluoroprop-2-yl), tert-butyl, triazolylmethyl, trifluoromethyl and acetyl.

A favoured value of $R^{11}$ is 2-hydroxyprop-2-yl.

A particular value of $R^{11}$ is trifluoromethyl.

One representative subset of the compounds of formula IA above is represented by the compounds of formula IIA, and salts and prodrugs thereof:

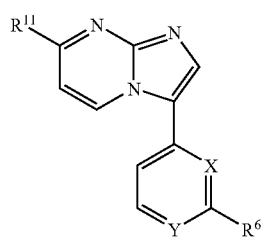

(IIA)

wherein

X represents CH and Y represents N; or

X represents N and Y represents CH or N;

$R^6$ represents hydrogen, halogen, cyano, trifluoromethyl, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, $C_{3-7}$ cycloalkyl, $C_{3-7}$ heterocycloalkyl, benzyl-tetrahydropyridinyl, $C_{1-6}$ alkoxy, methyltriazolyl($C_{1-6}$)alkoxy, $C_{1-6}$ alkylthio, $C_{1-6}$ alkylsulphonyl, $C_{2-6}$ alkylcarbonyl, amino, $C_{1-6}$ alkylamino, di($C_{1-6}$)alkylamino, $C_{2-6}$ alkylcarbonylamino, phenyl, ($C_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl) phenyl, (halo)(trifluoromethyl)phenyl, nitrophenyl, methoxyphenyl, (halo)(methoxy)phenyl, trifluoromethoxy-phenyl, (halo)(trifluoromethoxy) phenyl, methylenedioxy-phenyl, ($C_{2-6}$)alkylcarbonyl-phenyl, trifluorothio-phenyl, ($C_{1-6}$)alkylsulphonyl-phenyl, di($C_{1-6}$)alkylaminocarbonyl-phenyl, di($C_{1-6}$)alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, methyltetrazolyl-phenyl or optionally substituted heteroaryl, the optional substituents on the heteroaryl moiety being selected from oxy, halogen, cyano and $C_{1-6}$ alkyl; and $R^{11}$ is as defined above.

The present invention also provides a compound of formula IIA as depicted above, or a salt thereof or a prodrug thereof, wherein $R^6$ represents hydrogen, halogen, cyano, trifluoromethyl, $C_{1-6}$ alkyl, halo($C_{1-6}$)alkyl, $C_{1-6}$ alkoxy($C_{1-6}$)alkyl, $C_{3-7}$ cycloalkyl, $C_{3-7}$ heterocycloalkyl, $C_{1-6}$ alkoxy, methyltriazolyl($C_{1-6}$)alkoxy, $C_{1-6}$ alkylthio, $C_{1-6}$ alkylsulphonyl, amino, $C_{1-6}$ alkylamino, di($C_{1-6}$) alkylamino, $C_{2-6}$ alkylcarbonylamino, phenyl, fluorophenyl, chlorophenyl, cyanophenyl, (fluoro)(cyano)phenyl, nitrophenyl, methoxyphenyl, thiadiazolyl-phenyl, methylthiadiazolyl-phenyl, methyltetrazolyl-phenyl or optionally substituted heteroaryl, the optional substituents on the heteroaryl moiety being selected from oxy, halogen, cyano and $C_{1-6}$ alkyl; and X, Y and $R^{11}$ are as defined above.

The present invention further provides a compound of formula IIA as depicted above, or a salt thereof or a prodrug thereof, wherein $R^6$ represents hydrogen, halogen, cyano, trifluoromethyl, $C_{1-6}$ alkyl, $C_{3-7}$ cycloalkyl, $C_{3-7}$ heterocycloalkyl, $C_{1-6}$ alkoxy or cyanophenyl; and X, Y and $R^{11}$ are as defined above.

Illustrative values of $R^6$ include hydrogen, fluoro, chloro, bromo, iodo, cyano, trifluoromethyl, methyl, isopropyl, tert-butyl, chloromethyl, fluoropropyl (especially 2-fluoroprop-2-yl), difluoroethyl (especially 1,1-difluoroethyl), hydroxypropyl (especially 2-hydroxyprop-2-yl), methoxymethyl, cyclopentyl, pyrrolidinyl, morpholinyl, benzyl-tetrahydropyridinyl, methoxy, ethoxy, isopropoxy, tert-butoxy, methyltriazolyl-methoxy, methylthio, ethylthio, methanesulphonyl, acetyl, tert-butylamino, dimethylamino, acetylamino, phenyl, methylphenyl, isopropylphenyl, tert-butylphenyl, fluorophenyl, chlorophenyl, bromophenyl, difluorophenyl, dichlorophenyl, dibromophenyl, (chloro)(fluoro)phenyl, trifluorophenyl, trichlorophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (chloro)(trifluoromethyl)phenyl, nitrophenyl, methoxyphenyl, (fluoro)(methoxy)phenyl, trifluoromethoxy-phenyl, (fluoro)(trifluoromethoxy)phenyl, methylenedioxy-phenyl, acetylphenyl, trifluorothio-phenyl, methanesulphonyl-phenyl, ethanesulphonyl-phenyl, dimethylaminocarbonyl-phenyl, dimethylaminosulphonyl-phenyl, (fluoro)(morpholinylmethyl)phenyl, (fluoro)(pyridinyl)phenyl, imidazolyl-phenyl, thiadiazolyl-phenyl, methylthiadiazolyl-phenyl, (fluoro)(triazolyl)phenyl, methyltetrazolyl-phenyl, pyridinyl, oxypyridinyl, fluoropyridinyl, chloropyridinyl, cyanopyridinyl, methylpyridinyl, dimethyl-pyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Suitable values of $R^6$ include hydrogen, fluoro, chloro, bromo, iodo, cyano, trifluoromethyl, methyl, tert-butyl, chloromethyl, methoxymethyl, cyclopentyl, pyrrolidinyl, morpholinyl, methoxy, ethoxy, isopropoxy, tert-butoxy, methyltriazolyl-methoxy, methylthio, ethylthio, methanesulphonyl, tert-butylamino, dimethylamino, acetylamino, phenyl, fluorophenyl, chlorophenyl, cyanophenyl, (fluoro)(cyano)phenyl, nitrophenyl, methoxyphenyl, thiadiazolyl-phenyl, methylthiadiazolyl-phenyl, methyltetrazolyl-phenyl, pyridinyl, oxypyridinyl, chloropyridinyl, cyanopyridinyl, pyridazinyl, pyrimidinyl, pyrazinyl, furyl, thienyl, cyanothienyl, pyrrolyl, pyrazolyl, oxazolyl, thiazolyl, isothiazolyl, imidazolyl, methylimidazolyl and triazolyl.

Typical values of $R^6$ include hydrogen, chloro, bromo, cyano, trifluoromethyl, methyl, cyclopentyl, pyrrolidinyl (especially pyrrolidin-1-yl), methoxy and cyanophenyl (especially 2-cyanophenyl).

A favoured value of $R^6$ is fluorophenyl.

A preferred value of $R^6$ is difluorophenyl.

An illustrative subset of the compounds of formula IIA above is represented by the compounds of formula IIB, and salts and prodrugs thereof:

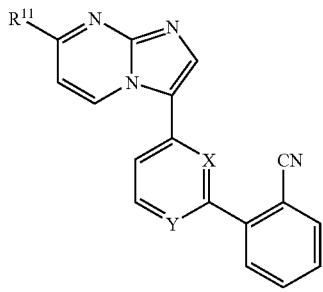

(IIB)

wherein X, Y and $R^{11}$ are as defined above.

Another illustrative subset of the compounds of formula IIA above is represented by the compounds of formula IIC, and salts and prodrugs thereof:

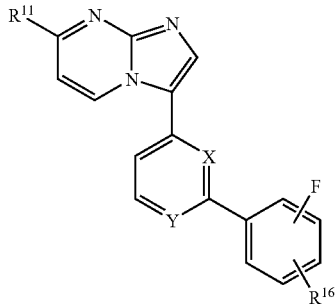

(IIC)

wherein
$R^{16}$ represents hydrogen, fluoro or cyano; and
X, Y and $R^{11}$ are as defined above.
In a favoured embodiment, $R^{16}$ represents hydrogen.
In another embodiment, $R^{16}$ represents cyano.

In a preferred embodiment, $R^{16}$ represents fluoro.

In one embodiment of the compounds of formula IIA, IIB and IIC, X is CH and Y is N.

In another embodiment of the compounds of formula IIA, IIB and IIC, X is N and Y is CH.

In a further embodiment of the compounds of formula IIA, IIB and IIC, X and Y are both N.

Specific compounds within the scope of the present invention include:

3-(6-bromopyridin-2-yl)-7-trifluoromethylimidazo[1,2-α]pyrimidine;
2-[6-(7-trifluoromethylimidazo[1,2-α]pyrimidin-3-yl)pyridin-2-yl]-benzonitrile;
2-[4-(7-trifluoromethylimidazo[1,2-α]pyrimidin-3-yl)pyridin-2-yl]-benzonitrile;
3-(3-chloromethyl-[1,2,4]thiadiazol-5-yl)-7-trifluoromethylimidazo[1,2-α]pyrimidine;
3-(2-chloropyrimidin-4-yl)-7-trifluoromethylimidazo[1,2-α]pyrimidine;
3-(thiazol-2-yl)-7-trifluoromethylimidazo[1,2-α]pyrimidine;
6-(7-trifluoromethylimidazo[1,2-α]pyrimidin-3-yl)nicotinonitrile;
3-(pyridin-2-yl)-7-trifluoromethylimidazo[1,2-α]pyrimidine;
3-[6-(pyrrolidin-1-yl)pyridin-2-yl]-7-trifluoromethylimidazo[1,2-α]pyrimidine;
7-trifluoromethyl-3-(6-trifluoromethylpyridin-2-yl)imidazo[1,2-α]pyrimidine;
3-(6-methylpyridin-2-yl)-7-trifluoromethylimidazo[1,2-α]pyrimidine;
3-(6-methoxypyridin-2-yl)-7-trifluoromethylimidazo[1,2-α]pyrimidine;
3-(6-cyclopentylpyridin-2-yl)-7-trifluoromethylimidazo[1,2-α]pyrimidine;
3-(5-methylpyridin-2-yl)-7-trifluoromethylimidazo[1,2-α]pyrimidine;
7-trifluoromethyl-3-(5-trifluoromethylpyridin-2-yl)imidazo[1,2-α]pyrimidine;
2-[4-(7-trifluoromethylimidazo[1,2-α]pyrimidin-3-yl)pyrimidin-2-yl]-benzonitrile;
3-[3-(thien-2-yl)-[1,2,4]thiadiazol-5-yl]-7-trifluoromethylimidazo[1,2-α]pyrimidine;
3-[4-(pyridin-3-yl)thien-2-yl]-7-trifluoromethylimidazo[1,2-α]pyrimidine;
3-[5-(pyridin-3-yl)thien-3-yl]-7-trifluoromethylimidazo[1,2-α]pyrimidine;
3-[4-(pyridin-3-yl)thiazol-2-yl]-7-trifluoromethylimidazo[1,2-α]pyrimidine;
2-{6-[7-(1-hydroxy-1-methylethyl)imidazo[1,2-α]pyrimidin-3-yl]pyridin-2-yl}benzonitrile;
5-fluoro-2-{6-[7-(1-hydroxy-1-methylethyl)imidazo[1,2-α]pyrimidin-3-yl]pyridin-2-yl}benzonitrile;
3-{6-[7-(1-hydroxy-1-methylethyl)imidazo[1,2-α]pyrimidin-3-yl]pyridin-2-yl}thiophene-2-carbonitrile;
4-fluoro-2-{6-[7-(1-hydroxy-1-methylethyl)imidazo[1,2-α]pyrimidin-3-yl]pyridin-2-yl}benzonitrile;
3-(6-bromopyridin-2-yl)-7-(1-fluoro-1-methylethyl)imidazo[1,2-α]pyrimidine;
2-{6-[7-(1-fluoro-1-methylethyl)imidazo[1,2-α]pyrimidin-3-yl]pyridin-2-yl}benzonitrile;
2-{6-[7-(1-cyano-1-methylethyl)imidazo[1,2-α]pyrimidin-3-yl]pyridin-2-yl}benzonitrile;
2-[6-(7-tert-butylimidazo[1,2-α]pyrimidin-3-yl)pyridin-2-yl]-5-fluorobenzonitrile;
4-fluoro-2-[6-(7-trifluoromethylimidazo[1,2-α]pyrimidin-3-yl)pyridin-2-yl]benzonitrile;

3-(2-fluoropyridin-5-yl)-7-trifluoromethylimidazo[1,2-α]
pyrimidine;
3-(2-phenylpyridin-5-yl)-7-trifluoromethylimidazo[1,2-α]
pyrimidine;
3-[2-(4-fluorophenyl)pyridin-5-yl)]-7-
trifluoromethylimidazo[1,2-α]pyrimidine;
3-[2-(1H-pyrrol-1-yl)pyridin-5-yl]-7-
trifluoromethylimidazo[1,2-α]pyrimidine;
3-(2-chloropyrimidin-4-yl)-7-(1-hydroxy-1-methylethyl)
imidazo[1,2-α]pyrimidine;
5-fluoro-2-{4-[7-(1-hydroxy-1-methylethyl)imidazo[1,2-α]
pyrimidin-3-yl]-pyrimidin-2-yl}benzonitrile;
2-[3-(2-(pyridin-3-yl)pyrimidin-4-yl)imidazo[1,2-α]
pyrimidin-7-yl]propan-2-ol;
2-{4-[7-(1-hydroxy-1-methylethyl)imidazo[1,2-α]
pyrimidin-3-yl]pyrimidin-2-yl}thiophene-3-carbonitrile;
5-fluoro-2-{4-[7-trifluoromethylimidazo[1,2-α]pyrimidin-
3-yl]pyrimidin-2-yl}benzonitrile;
2-[3-(2-trifluoromethylpyrimidin-4-yl)imidazo[1,2-α]
pyrimidin-7-yl]propan-2-ol;
2-[3-(2-(thiazol-2-yl)pyrimidin-4-yl)imidazo[1,2-α]
pyrimidin-7-yl]propan-2-ol;
2-[3-(2-(imidazol-1-yl)pyrimidin-4-yl)imidazo[1,2-α]
pyrimidin-7-yl]propan-2-ol;
2-[3-(2-(pyridin-4-yl)pyrimidin-4-yl)imidazo[1,2-α]
pyrimidin-7-yl]propan-2-ol
2-[3-(2-(furan-2-yl)pyrimidin-4-yl)imidazo[1,2-α]
pyrimidin-7-yl]propan-2-ol;
2-[3-(2-(furan-3-yl)pyrimidin-4-yl)imidazo[1,2-α]
pyrimidin-7-yl]propan-2-ol;
2-{3-[2-(1-oxypyridin-4-yl)pyrimidin-4-yl]imidazo[1,2-α]
pyrimidin-7-yl}propan-2-ol;
3-[6-(1H-imidazol-1-yl)pyridin-2-yl]-7-
trifluoromethylimidazo[1,2-α]pyrimidine;
3-[6-(morpholin-4-yl)pyridin-2-yl]-7-
trifluoromethylimidazo[1,2-α]pyrimidine;
3-(6-phenylpyridin-2-yl)-7-trifluoromethylimidazo[1,2-α]
pyrimidine;
6-(7-trifluoromethylimidazo[1,2-α]pyrimidin-3-yl)-2,3'-
bipyridine;
N-[6-(7-trifluoromethylimidazo[1,2-α]pyrimidin-3-yl)
pyridin-2-yl]acetamide;
N-(tert-butyl)-6-(7-trifluoromethylimidazo[1,2-α]
pyrimidin-3-yl)pyridin-2-ylamine;
3-[6-(1H-[1,2,4]triazol-1-yl)pyridin-2-yl]-7-
trifluoromethylimidazo[1,2-α]pyrimidine;
3-[6-(isothiazol-4-yl)pyridin-2-yl]-7-
trifluoromethylimidazo[1,2-α]pyrimidine;
3-(6-isopropoxypyridin-2-yl)-7-trifluoromethylimidazo[1,
2-α]pyrimidine;
3-(6-ethoxypyridin-2-yl)-7-trifluoromethylimidazo[1,2-α]
pyrimidine;
6-(7-trifluoromethylimidazo[1,2-α]pyrimidin-3-yl)-2,2'-
bipyridine;
6-(7-trifluoromethylimidazo[1,2-α]pyrimidin-3-yl)-2,4'-
bipyridine;
3-(6-methoxymethylpyridin-2-yl)-7-trifluoromethylimidazo
[1,2-α]pyrimidine;
3-[6-(thien-3-yl)pyridin-2-yl]-7-trifluoromethylimidazo[1,
2-α]pyrimidine;
7-(1,1-dimethoxyethyl)-3-[2-(pyridin-4-yl)pyrimidin-4-yl]
imidazo[1,2-α]pyrimidine;
2-{3-[2-(3-nitrophenyl)pyrimidin-4-yl]imidazo[1,2-α]
pyrimidin-7-yl}propan-2-ol;
2-{3-[2-(3-fluorophenyl)pyrimidin-4-yl]imidazo[1,2-α]
pyrimidin-7-yl}propan-2-ol;
1-[3-(2-(pyridin-4-yl)pyrimidin-4-yl)imidazo[1,2-α]
pyrimidin-7-yl]ethanone;
6-[7-([1,2,4]triazol-1-ylmethyl)imidazo[1,2-α]pyrimidinyl-
3-yl]-2,3'-bipyridine;
2-[6-(7-([1,2,4]triazol-1-ylmethyl)imidazo[1,2-α]
pyrimidin-3-yl)pyridin-2-yl]benzonitrile;
6'-(7-trifluoromethylimidazo[1,2-α]pyrimidin-3-yl)-2,2'-
bipyridinyl-3-carbonitrile;
6'-[7-(1-fluoro-1-methylethyl)imidazo[1,2-α]pyrimidin-3-
yl]-2,2'-bipyridinyl-3-carbonitrile;
the compounds whose structures are depicted in the accompanying Tables as Examples 68 to 109;
2-{3-[2-(2,4-difluorophenyl)pyrimidin-4-yl]imidazo[1,2-α]
pyrimidin-7-yl}propan-2-ol;
2-{3-[2-(3,4-difluorophenyl)pyrimidin-4-yl]imidazo[1,2-α]
pyrimidin-7-yl}propan-2-ol;
2-{3-[2-(1-benzyl-1,2,3,6-tetrahydropyridin-4-yl)
pyrimidin-4-yl]imidazo[1,2-α]pyrimidin-7-yl}propan-2-
ol;
2-{3-[2-(1,1-difluoroethyl)pyrimidin-4-yl]imidazo[1,2-α]
pyrimidin-7-yl}propan-2-ol;
1-{4-[7-(1-hydroxy-1-methylethyl)imidazo[1,2-α]
pyrimidin-3-yl]pyrimidin-2-yl}ethanone;
2-{3-[2-(1-hydroxy-1-methylethyl)pyrimidin-4-yl]imidazo
[1,2-α]pyrimidin-7-yl}propan-2-ol;
2-{3-[2-(1-fluoro-1-methylethyl)pyrimidin-4-yl]imidazo[1,
2-α]pyrimidin-7-yl}propan-2-ol;
2-[3-(2-isopropylpyrimidin-4-yl)imidazo[1,2-α]pyrimidin-
7-yl]propan-2-ol;
the compounds whose structures are depicted in the accompanying Tables as Examples 118 to 200;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the anxiolytic compounds of the invention is ideally 50 nM or less, preferably 10 nM or less, and more preferably 5 nM or less.

The anxiolytic compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention may exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are likely to be substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In another aspect, the present invention provides a method for the treatment and/or prevention of cognitive disorders, including dementing conditions such as Alzheimer's disease, which comprises administering to a patient in need of such treatment an effective amount of a compound of formula I as defined above or a pharmaceutically acceptable salt thereof.

Cognition enhancement can be shown by testing the compounds in the Morris watermaze as reported by McNamara and Skelton, *Psychobiology*, 1993, 21, 101–108. Further details of relevant methodology are described in WO 96/25948.

Cognitive disorders for which the compounds of the present invention may be of benefit include delirium, dementia, amnestic disorders, and cognition deficits, including age-related memory deficits, due to traumatic injury, stroke, Parkinson's disease and Down Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV disease, head trauma, Parkinson's disease or Creutzfeld-Jakob disease.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of neurological disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

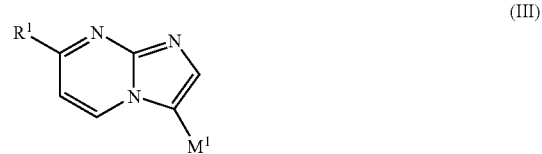

(III)

(IV)

wherein Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, 1,3-propanediol or neopentyl glycol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo or chloro.

The transition metal catalyst of use in the reaction between compounds III and IV is suitably tetrakis(triphenylphosphine)-palladium(0). The reaction is conveniently carried out at an elevated temperature in a solvent such as tetrahydrofuran, 1,4-dioxane or N,N-dimethylacetamide, typically in the presence of potassium phosphate, cesium carbonate or copper(I) iodide.

In an alternative procedure, the compounds according to the present invention may be prepared by a process which comprises reacting a compound of formula V with a compound of formula VI:

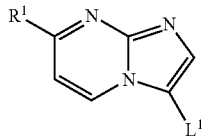
(V)

M¹—Z (VI)

wherein Z, R¹, L¹ and M¹ are as defined above; in the presence of a transition metal catalyst; under conditions analogous to those described above for the reaction between compounds III and IV.

In another procedure, the compounds according to the present invention wherein Z represents a thiazol-2-yl moiety substituted at the 4-position by a substituent $R^7$, in which $R^7$ represents any allowable substituent on the group Z (in particular wherein $R^7$ represents pyridin-3-yl), may be prepared by a process which comprises reacting a compound of formula VII with a compound of formula VIII:

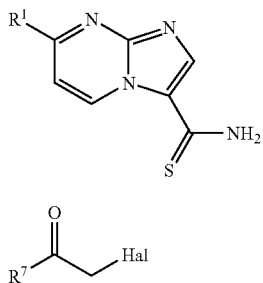
(VII)

(VIII)

wherein R¹ and $R^7$ are as defined above, and Hal represents a halogen atom, e.g. bromo.

The reaction between compounds VII and VIII is conveniently effected at an elevated temperature in a solvent such as N,N-dimethylformamide.

Where M¹ in the intermediates of formula III above represents —Sn(Alk)₃ in which Alk is n-butyl, this compound may be prepared by reacting a compound of formula V as defined above with tributyltin chloride.

The reaction is conveniently effected by stirring compound V with isopropylmagnesium chloride in a solvent such as tetrahydrofuran, with subsequent addition of tributyltin chloride.

Where L¹ in the intermediates of formula V above represents bromo, this compound may be prepared by bromination of the corresponding compound of formula IX:

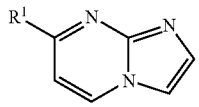
(IX)

wherein R¹ is as defined above; typically by treatment with bromine in methanol, in the presence of sodium acetate and optionally also potassium bromide.

The intermediates of formula IX may be prepared by reacting chloroacetaldehyde or bromoacetaldehyde, or an acetal derivative thereof, e.g. the dimethyl or diethyl acetal thereof, with the requisite compound of formula X:

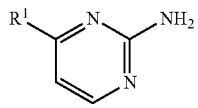
(X)

wherein R¹ is as defined above.

Where chloroacetaldehyde or bromoacetaldehyde is utilised as one of the reactants, the reaction is conveniently carried out by heating the reactants under basic conditions in a suitable solvent, e.g. sodium methoxide or sodium hydrogencarbonate in a lower alkanol such as methanol and/or ethanol at the reflux temperature of the solvent. Where an acetal derivative of chloroacetaldehyde or bromoacetaldehyde, e.g. the dimethyl or diethyl acetal thereof, is utilised as one of the reactants, the reaction is conveniently effected by heating the reactants under acidic conditions in a suitable solvent, e.g. aqueous hydrobromic acid in a lower alkanol such as methanol or ethanol, typically at the reflux temperature of the solvent.

The intermediates of formula IX may also be prepared by reacting a compound of formula XI or XII with the compound of formula XIII, or with an acid addition salt of the latter compound, e.g. the hemisulfate salt:

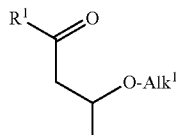
(XI)

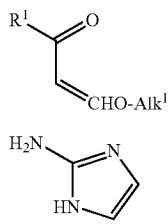
(XII)

(XIII)

wherein R¹ is as defined above, and Alk¹ represents $C_{1-6}$ alkyl.

Typical values of Alk¹ include methyl and ethyl.

The reaction is conveniently effected by heating the reactants under basic conditions in a suitable solvent, e.g. a lower alkoxide such as sodium methoxide or ethoxide in a lower alkanol such as methanol or ethanol, typically at the reflux temperature of the solvent.

The intermediates of formula VII above may be prepared from the appropriate compound of formula XIV:

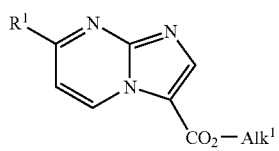
(XIV)

wherein R¹ and Alk¹ are as defined above; by treatment with ammonia, typically in aqueous ethanol, followed by treatment of the resulting amide derivative with Lawesson's reagent [2,4-bis(4-methoxyphenyl)-1,3-dithia-2,4-diphosphetane-2,4-disulfide], typically in refluxing toluene.

The intermediates of formula XIV may be prepared by reacting a compound of formula X as defined above with N,N-dimethylformamide dimethyl acetal, followed by treatment of the product thereby obtained with ethyl bromoacetate.

Both steps of this transformation may conveniently be accomplished by heating under reflux in toluene.

In another procedure, the compounds according to the present invention wherein $R^1$ represents an aryl or heteroaryl moiety may be prepared by a process which comprises reacting a compound of formula XV with a compound of formula XVI:

$$R^{1a}—M^1 \quad \text{(XV)}$$

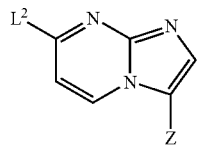

(XVI)

wherein Z and $M^1$ are as defined above, $R^{1a}$ represents an aryl or heteroaryl moiety, and $L^2$ represents a suitable leaving group; in the presence of a transition metal catalyst.

The leaving group $L^2$ is typically a halogen atom, e.g. chloro.

The transition metal catalyst of use in the reaction between compounds XV and XVI is suitably tetrakis(triphenylphosphine)-palladium(0), in which case the reaction is conveniently effected at an elevated temperature in a solvent such as N,N-dimethylacetamide, typically in the presence of potassium phosphate or in the presence of lithium chloride and copper(I) iodide. Alternatively, the transition metal catalyst may suitably be tris(dibenzylideneacetone)palladium(0), in which case the reaction is conveniently effected at an elevated temperature in a solvent such as 1,4-dioxane, typically in the presence of tri-tert-butylphosphine and cesium carbonate.

Where $L^2$ in the compounds of formula XVI above represents a halogen atom, these compounds correspond to compounds of formula I as defined above wherein $R^1$ represents halogen, and they may therefore be prepared by any of the methods described above for the preparation of the compounds according to the invention.

In a further procedure, the compounds according to the invention may be prepared by a process which comprises reacting a compound of formula IV as defined above with a compound of formula IX as defined above in the presence of a transition metal catalyst.

The transition metal catalyst of use in the reaction between compounds IV and IX is suitably tetrakis(triphenylphosphine)-palladium(0), in which case the reaction is conveniently effected at an elevated temperature in a solvent such as 1,4-dioxane, typically in the presence of cesium carbonate.

The compound of formula XIII above is commercially available from the Sigma-Aldrich Company Ltd., Dorset, United Kingdom.

Where they are not commercially available, the starting materials of formula IV, VI, VIII, X, XI, XII and XV may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein the moiety Z is substituted by a halogen atom, e.g. bromo, may be converted into the corresponding compound wherein the moiety Z is substituted by an aryl or heteroaryl group, e.g. 2-cyanophenyl or pyridin-3-yl, by treatment with the requisite aryl or heteroaryl boronic acid or cyclic ester thereof formed with an organic diol, e.g. 2-cyanophenylboronic acid or pyridine-3-boronic acid-1,3-propanediol cyclic ester, in the presence of a transition metal catalyst such as tetrakis(triphenylphosphine)palladium(0), in which case the reaction is conveniently effected at an elevated temperature in a solvent such as N,N-dimethylacetamide, aqueous 1,4-dioxane or aqueous tetrahydrofuran, typically in the presence of potassium phosphate, sodium carbonate or cesium carbonate; or by treatment with the appropriate stannyl reagent, e.g. 2-tributylstannylbenzonitrile, in the presence of a transition metal catalyst such as dichloro[1,1'-bis(diphenylphosphino)ferrocene]-palladium(II), in which case the reaction is conveniently effected at a elevated temperature in a solvent such as N,N-dimethylacetamide, typically in the presence of lithium chloride and copper(I) chloride; or by treatment with the appropriate stannyl reagent in the presence of a transition metal catalyst such as tetrakis(triphenylphosphine)-palladium(0), in which case the reaction is conveniently accomplished at an elevated temperature in a solvent such as tetrahydrofuran or 1,4-dioxane, typically in the presence of copper(I) iodide; or, where the moiety Z in the desired compound of formula I is substituted by imidazol-1-yl, simply by treatment with imidazole in the presence of a strong base such as lithium hexamethyldisilazide (LiHMDS). A compound of formula I wherein the moiety Z is substituted by pyridinyl may be converted into the corresponding compound wherein Z is substituted by N-oxypyridinyl by treatment with meta-chloroperbenzoic acid. A compound of formula I wherein Z is substituted by a halogen atom, e.g. iodo, may be converted, by treatment with isopropylmagnesium chloride, into a Grignard reagent which may be reacted with an aldehyde such as acetaldehyde to afford a secondary alcohol, e.g. the 1-hydroxyethyl derivative; and this compound may in turn be treated with an oxidising agent, e.g. Dess-Martin periodinane, to afford the corresponding compound of formula I wherein Z is substituted by acetyl. The resulting acetyl derivative may be converted, by treatment with methylmagnesium chloride, into the corresponding compound wherein Z is substituted by 2-hydroxyprop-2-yl; and this compound may in turn be treated with (diethylamino)sulfur trifluoride (DAST) to afford the corresponding compound of formula I wherein Z is substituted by 2-fluoroprop-2-yl. A compound of formula I wherein $R^1$ represents —C(O—Alk$^1$)$_2$R$^a$ initially obtained, wherein Alk$^1$ is as defined above, may be converted into the corresponding compound of formula I wherein $R^1$ represents —COR$^a$ by hydrolysis with a mineral acid, typically aqueous hydrochloric acid. A compound wherein $R^1$ represents formyl may be reduced with sodium triacetoxyborohydride to the corresponding compound wherein $R^1$ represents hydroxymethyl. A compound of formula I wherein $R^1$ represents hydroxymethyl may be oxidised to the corresponding compound of formula I wherein $R^1$ represents formyl by treatment with manganese dioxide. The formyl derivative thereby obtained may be condensed with a hydroxylamine derivative of formula $H_2N—OR^b$ to provide a compound of formula I wherein $R^1$ represents —CH=NOR$^b$. Furthermore, a compound of formula I wherein $R^1$ represents —CH=NOH may be treated with triethylamine in the presence of 1,1'-carbonyldiimidazole to afford a corresponding compound of formula I wherein $R^1$ represents cyano. Alternatively, the compound of formula I wherein $R^1$ represents formyl may be reacted with a Grignard reagent of formula $R^aMgBr$ to afford a compound of formula I wherein $R^1$ represents —CH(OH)$R^a$, and this compound may in turn be oxidised using manganese dioxide to the corresponding compound of formula I wherein $R^1$ represents —CO$R^a$. The latter compound may then be condensed with a hydroxylamine derivative of formula $H_2N$—O$R^b$ to provide a compound of formula I wherein $R^1$ represents —C$R^a$=NO$R^b$. A compound of formula I wherein $R^1$ represents —CH(OH)$R^a$ may be converted into the corresponding compound of formula I wherein $R^1$ represents —CHF$R^a$ by treatment with DAST. Similarly, a compound of formula I wherein $R^1$ represents —CO$R^a$ may be converted into the corresponding compound of formula I wherein $R^1$ represents —CF$_2R^a$ by treatment with DAST. A compound of formula I wherein $R^1$ represents amino may be converted into the corresponding compound of formula I wherein $R^1$ represents chloro by diazotisation, using sodium nitrite, followed by treatment with copper(I) chloride. A compound of formula I wherein $R^1$ represents —COCH$_3$ may be treated with thioacetamide in the presence of pyridinium tribromide to furnish the corresponding compound of formula I wherein $R^1$ represents 2-methylthiazol-5-yl. Moreover, a compound of formula I wherein $R^1$ is formyl may be treated with (p-tolylsulfonyl)methyl isocyanide (TosMIC) in the presence of potassium carbonate to afford the corresponding compound of formula I wherein $R^1$ represents oxazol-5-yl. A compound of formula I wherein $R^1$ represents hydroxymethyl may be treated with carbon tetrabromide and triphenylphosphine to afford the corresponding compound of formula I wherein $R^1$ represents bromomethyl, which may then be reacted (typically in situ) with the sodium salt of imidazole or 1H-[1,2,4]triazole to provide a compound of formula I wherein $R^1$ represents imidazol-1-ylmethyl or [1,2,4]triazol-1-ylmethyl respectively; or with the sodium salt of 1H-[1,2,3]triazole to provide a mixture of compounds of formula I wherein $R^1$ represents [1,2,3]triazol-1-ylmethyl and [1,2,3]triazol-2-ylmethyl; or with morpholine to provide a compound of formula I wherein $R^1$ represents morpholin-4-ylmethyl.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (-)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 and/or α3 and/or α5 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 and/or α5 subunit of the human GABA$_A$ receptor of 100 nM or less.

EXAMPLE 1

3-(6-Bromopyridin-2-yl)-7-trifluoromethylimidazo[1,2-α]pyrimidine

A mixture of 2-amino-4-(trifluoromethyl)pyrimidine (prepared according to Zanatta et al. in *J. Heterocyclic*

*Chem.*, 1997, 34(2), 509–513) (500 mg, 3.1 mmol) and bromoacetaldehyde diethyl acetal (1.38 ml, 9.2 mmol) in ethanol (10 ml) was treated with hydrobromic acid (0.5 ml of a 48% aqueous solution) and then heated at 70° C. for 12 h. The reaction was cooled to ambient temperature then pre-adsorbed onto silica. Purification by chromatography on silica eluting with dichloromethane (containing 1% conc. ammonia) on a gradient of methanol (1–5%) afforded 7-trifluoromethylimidazo[1,2-α]pyrimidine (500 mg, 87%) as a cream-coloured solid: $\delta_H$ (400 MHz, CDCl$_3$) 7.22 (1H, d, J 7), 7.74 (1H, d, J 1), 8.03 (1H, d, J 1), 8.67 (1H, d, J 7).

7-Trifluoromethylimidazo[1,2-α]pyrimidine (20. g, 10.7 mmol) and sodium acetate (1.1 mg, 13.4 mmol) were dissolved in methanol (30 ml) which had been saturated with potassium bromide and this mixture was cooled to −10° C. before dropwise addition of bromine (1.86 mg, 11.7 mmol) over 5 min. On complete addition the mixture was quenched by addition of 1M sodium sulfite solution (2 ml) and the solvent removed in vacuo. The residue was treated with water (100 ml) and saturated sodium hydrogencarbonate solution (100 ml) and extracted with ethyl acetate (3×100 ml). The organics were combined then washed with brine (100 ml), dried over anhydrous sodium sulfate and evaporated to give an off-white solid. This solid was purified by silica gel chromatography eluting with dichloromethane and 1% conc. ammonia on a gradient of methanol (1–2%) to give 3-bromo-7-trifluoromethylimidazo[1,2-α]pyrimidine (1.98 g) as a white solid: $\delta_H$ (400 MHz, CDCl$_3$) 7.35 (1H, d, J 7), 8.02 (1H, s), 8.62 (1H, d, J 7).

To a cooled (−78° C.) solution of 3-bromo-7-trifluoromethylimidazo[1,2-α]pyrimidine (1.0 g, 3.78 mmol) in tetrahydrofuran (20 ml) was added isopropylmagnesium chloride (2.08 ml of a 2M solution in tetrahydrofuran, 4.16 mmol). After stirring for 5 min tributyltin chloride (1.2 ml, 4.42 mmol) was added and the reaction stirred for 10 min at −78° C. then allowed to warm to ambient temperature to give a solution of 3-tributylstannyl-7-trifluoromethylimidazo[1,2-α]pyrimidine in tetrahydrofuran (ca. 0.15M): m/z (ES$^+$) 474, 476, 478 (M$^+$+H).

To the degassed solution of 3-tributylstannyl-7-trifluoromethyl-imidazo[1,2-α]pyrimidine was added 2,6-dibromopyridine (1.8 g, 7.5 mmol) and tetrakis(triphenylphosphine)palladium(0) (218 mg, 0.18 mmol) and the mixture heated at reflux for 3 h. The crude reaction was adsorbed onto silica and purified by chromatography on silica gel eluting with isohexane on a gradient of ethyl acetate (20–60%) to give a yellow solid. Crystallisation from ethyl acetate/isohexane afforded 3-(6-bromopyridin-2-yl)-7-trifluoromethylimidazo[1,2-α]pyrimidine (702 mg) as a white solid: $\delta_H$ (400 MHz, DMSO) 7.64 (1H, d, J 9), 7.83 (1H, d, J 8), 7.93 (1H, dd, J 9 and 9), 8.20 (1H, d, J 9), 8.92 (1H, s), 10.18 (1H, d, J 9); m/z (ES$^+$) 343, 345 (M$^+$+H).

EXAMPLE 2

2-[6-(7-Trifluoromethylimidazo[1,2-α]pyrimidin-3-yl)pyridin-2-yl]-benzonitrile

To a degassed solution of 3-(6-bromopyridin-2-yl)-7-trifluoromethyl-imidazo[1,2-α]pyrimidine (200 mg, 0.58 mmol), 2-cyanophenylboronic acid (172 mg, 1.16 mmol) and potassium phosphate (370 mg, 1.75 mmol) in N,N-dimethylacetamide (4 ml) was added tetrakis(triphenylphosphine)paladium(0) (33.8 mg, 29.2 μmol) and the reaction heated at 80° C. for 18 h. After cooling to ambient temperature the reaction was poured onto a cartridge of strong cation-exchange resin and non-basic impurities removed by elution with methanol. The product was then eluted with a 2M solution of ammonia in methanol and evaporated to give an orange oil. This residue was purified by silica gel chromatography eluting with isohexane on a gradient of ethyl acetate (20–60%) to give a solid. Crystallisation from ethyl acetate-dichloromethane gave 2-[6-(7-trifluoromethylimidazo[1,2-α]pyrimidin-3-yl)pyridin-2-yl]benzonitrile (26 mg) as a white solid: $\delta_H$ (400 MHz, CDCl$_3$) 7.38 (1H, d, J 7), 7.61 (2H, m), 7.78 (2H, m), 7.91 (2H, m), 7.99 (1H, dd, J 9 and 9), 8.58 (1H, s), 10.62 (1H, d, J 9); m/z (ES$^+$) 366 (M$^+$+H).

EXAMPLE 3

2-[4-(7-Trifluoromethylimidazo[1,2-α]pyrimidin-3-yl)pyridin-2-yl]-benzonitrile

A suspension of 2,4-dichloropyridine hydrochloride (prepared according to Effenberger et al. in *Chem. Ber.*, 1992, 125, 1131) (1.24 g, 6.75 mmol), 2-cyanophenylboronic acid (0.97 g, 0.98 mmol) and potassium carbonate (2.84 g, 20.5 mmol) in tetrahydrofuran (23 ml) and water (11 ml) was degassed with nitrogen for 15 min. Tetrakis(triphenylphosphine)-palladium(0) (382 mg, 0.3 mmol) was then added and the mixture heated at reflux for 3 h then cooled to ambient temperature. The tetrahydrofuran layer was removed and the aqueous layer extracted with ethyl acetate. The organics were combined, dried over magnesium sulfate, filtered and adsorbed onto silica. Purification by chromatography on silica gel eluting with isohexane on a gradient of ethyl acetate (10–50%) gave an oil. Trituration with diethyl ether afforded 2-(4-chloropyridin-2-yl)benzonitrile (122 mg) as a white solid: $\delta_H$ (400 MHz, CDCl$_3$) 7.39 (1H, dd, J 5.3 and 1.8), 7.53–7.57 (1H, m), 7.69–7.73 (1H, m), 7.76–7.84 (3H, m), 8.68 (1H, d, J 4.7); m/z (ES$^+$) 215, 217 (M$^+$+H).

2-(4-Chloropyridin-2-yl)benzonitrile (65 mg, 0.3 mmol) was coupled with 3-tributylstannyl-7-trifluoromethylimidazo[1,2-α]pyrimidine (0.6 mmol) as described in Example 1 to give 2-[4-(7-trifluoromethylimidazo[1,2-α]pyrimidin-3-yl)pyridin-2-yl]benzonitrile (15 mg) as a white solid: $\delta_H$ (400 MHz, DMSO) 7.62 (1H, d, J 7.0), 7.69 (1H, m), 7.88 (1H, m), 7.93 (1H, dd, J 5 and 2), 8.04 (2H, m), 8.27 (1H, d, J 1), 8.60 (1H, s), 8.92 (1H, dd, J 5 and 1), 9.60 (1H, d, J 8); m/z (ES$^+$) 366 (M$^+$+H).

EXAMPLE 4

3-(3-Chloromethyl-[1,2,4]thiadiazol-5-yl)-7-trifluoromethylimidazo[1,2-α]pyrimidine 5-Chloro-3-chloromethyl-[1,2,4]thiadiazole (360 mg, 2.13 mmol) was coupled to 3-tributylstannyl-7-trifluoromethylimidazo[1,2-α]pyrimidine (1.4 mmol) by the method of Example 1 to afford 3-(3-chloromethyl-[1,2,4]thiadiazol-5-yl)-7-trifluoromethylimidazo[1,2-α]pyrimidine (115 mg) as a yellow solid: $\delta_H$ (400 MHz, DMSO) 5.08 (2H, s), 7.94 (1H, d, J 7), 9.12 (1H, s), 10.03 (1H, d, J 7); m/z (ES$^+$) 320 (M$^+$+H).

EXAMPLE 5

3-(2-Chloropyrimidin-4-yl)-7-trifluoromethylimidazo[1,2-α]pyrimidine 2,4-Dichloropyrimidine (317 mg, 2.13 mmol) was coupled to 3-tributylstannyl-7-trifluoromethylimidazo[1,2-α]pyrimidine (1.4 mmol) by the method of Example 1 to give 3-(2-chloropyrimidin-4-yl)-7-trifluoromethylimidazo[1,2-α]pyrimidine (167 mg) as a white solid: $\delta_H$ (400 MHz, DMSO) 7.91 (1H, d, J 7), 8.25 (1H, d, J 5), 8.83 (1H, d, J 5), 9.17 (1H, s), 10.22 (1H, d, J 7); m/z (ES$^+$) 300, 302 (M$^+$+H).

EXAMPLE 6

3-(Thiazol-2-yl)-7-trifluoromethylimidazo[1,2-α]pyrimidine

2-Bromothiazole (341 μl, 3.78 mmol) was coupled to 3-tributylstannyl-7-trifluoromethylimidazo[1,2-α]pyrimidine (1.8 mmol) by the method of Example 1 to give 3-(thiazol-2-yl)-7-trifluoromethyl-imidazo[1,2-α]pyrimidine (162 mg) as an off-white solid: $\delta_H$ (400 MHz, CDCl$_3$) 7.40 (2H, dd, J 4 and 3), 7.93 (1H, d, J 3), 8.48 (1H, s), 10.22 (1H, d, J 8); m/z (ES$^+$) 271 (M$^+$+H).

EXAMPLE 7

6-(7-Trifluoromethylimidazo[1,2-α]pyrimidin-3-yl)nicotinonitrile

6-Chloronicotinonitrile (295 mg, 2.13 mmol) was coupled to 3-tributylstannyl-7-trifluoromethylimidazo[1,2-α]pyrimidine (1.4 mmol) by the method of Example 1 to give 6-(7-trifluoromethylimidazo[1,2-α]pyrimidin-3-yl)nicotinonitrile (142 mg) as a white solid: $\delta_H$ (400 MHz, DMSO) 7.79 (1H, d, J 7), 8.35 (1H, m), 8.43 (1H, m), 9.06 (1H, s), 9.14 (1H, s), 10.41 (1H, d, J 7); m/z (ES$^+$) 290 (M$^+$+H).

EXAMPLE 8

3-(Pyridin-2-yl)-7-trifluoromethylimidazo[1,2-α]pyrimidine

2-Chloropyridine (361 μl, 3.78 mmol) was coupled to 3-tributylstannyl-7-trifluoromethylimidazo[1,2-α]pyrimidine (1.89 mmol) by the method of Example 1 to give 3-(pyridin-2-yl)-7-trifluoromethyl-imidazo[1,2-α]pyrimidine (134 mg) as a white solid: $\delta_H$ (400 MHz, CDCl$_3$) 7.24–7.30 (1H, m), 7.33 (1H, d, J 7.0), 7.82–7.84 (2H, m), 8.51 (1H, s), 8.68–8.70 (1H, m), 10.54 (1H, d, J 7.0); m/z (ES$^+$) 265 (M$^+$+H).

EXAMPLE 9

3-[6-(Pyrrolidin-1-yl)pyridin-2-yl]-7-trifluoromethylimidazo[1,2-α]pyrimidine

2-Bromo-6-(pyrrolidin-1-yl)pyridine (481 mg, 2.1 mmol) (prepared by the method of T. Sammakia et al., *J. Org. Chem.*, 1999, 64(13), 4652–4664) was coupled to 3-tributylstannyl-7-trifluoromethylimidazo[1,2-α]pyrimidine (1.4 mmol) by the method of Example 1 to give 3-[6-(pyrrolidin-1-yl)pyridin-2-yl]-7-trifluoromethylimidazo[1,2-α]pyrimidine (125 mg) as a white solid: $\delta_H$ (360 MHz, DMSO) 2.02 (4H, t, J 6.5), 3.51 (4H, bs), 6.43 (1H, d, J 8.4), 7.27 (1H, d, J 7.7), 7.63 (1H, t, J 7.9), 7.71 (1H, d, J 7.4), 8.72 (1H, s), 10.51 (1H, d, J 7.4); m/z (ES$^+$) 334 (M$^+$+H).

EXAMPLE 10

7-Trifluoromethyl-3-(6-trifluoromethylpyridin-2-yl)imidazo[1,2-α]pyrimidine

2-Chloro-6-trifluoromethylpyridine (385 mg, 2.1 mmol) was coupled to 3-tributylstannyl-7-trifluoromethylimidazo[1,2-α]pyrimidine (1.4 mmol) by the method of Example 1 to give 7-trifluoromethyl-3-(6-trifluoromethyl-pyridin-2-yl)imidazo[1,2-α]pyrimidine (65 mg) as a white solid: $\delta_H$ (360 MHz, DMSO) 7.89 (2H, d, J 7.4), 8.27 (1H, t, J 7.9), 8.46 (1H, d, J 7.4), 9.01 (1H, s), 10.26 (1H, d, J 7.4); m/z (ES$^+$) 333 (M$^+$+H).

EXAMPLE 11

3-(6-Methylpyridin-2-yl)-7-trifluoromethylimidazo[1,2-α]pyrimidine

2-Bromo-6-methylpyridine (367 mg, 2.1 mmol) was coupled to 3-tributylstannyl-7-trifluoromethylimidazo[1,2-α]pyrimidine (1.4 mmol) by the method of Example 1 to give 3-(6-methylpyridin-2-yl)-7-trifluoromethylimidazo[1,2-α]pyrimidine (142 mg) as a white solid: $\delta_H$ (400 MHz, DMSO) 2.62 (3H, s), 7.26 (1H, d, J 7.4), 7.70 (1H, d, J 7.4), 7.86 (1H, t, J 7.8), 7.94 (1H, s), 8.83 (1H, s), 10.55 (1H, d, J 7.8); m/z (ES$^+$) 279 (M$^+$+H).

EXAMPLE 12

3-(6-Methoxypyridin-2-yl)-7-trifluoromethylimidazo[1,2-α]pyrimidine

2-Chloro-6-methoxypyridine (305 mg, 2.1 mmol) was coupled to 3-tributylstannyl-7-trifluoromethylimidazo[1,2-α]pyrimidine (1.4 mmol) by the method of Example 1 to give 3-(6-methoxypyridin-2-yl)-7-trifluoromethylimidazo[1,2-α]pyrimidine (43 mg) as a white solid: $\delta_H$ (400 MHz, DMSO) 4.04 (3H, s), 6.84 (1H, d, J 8.2), 7.73 (2H, t, J 6.7), 7.88 (1H, t, J 7.8), 8.81 (1H, s), 10.37 (1H, d, J 7.0); m/z (ES$^+$) 295 (M$^+$+H).

EXAMPLE 13

3-(6-Cyclopentylpyridin-2-yl)-7-trifluoromethylimidazo[1,2-α]pyrimidine

To 2,6-dibromopyridine (5.9 g, 25 mmol) and tetrakis(triphenylphosphine)palladium(0) (1.4 g, 1.2 mmol) was added cyclopentylzinc bromide (50 ml, 0.5 M solution in tetrahydrofuran) and the mixture heated at reflux for 18 h. The reaction was diluted with ethyl acetate and washed with water. The organic phase was separated, dried over magnesium sulfate, filtered and evaporated in vacuo to give an oil. The crude product was chromatographed on silica, eluting on a gradient from 1 to 5% methanol in dichloromethane, to give 2-bromo-6-cyclopentylpyridine (3.25 g) as a white solid: $\delta_H$ (400 MHz, CDCl$_3$) 1.60–1.90 (6H, m), 2.09 (2H, m), 3.17 (1H, m), 7.12 (1H, d, J 7.4), 7.28 (1H, d, J 7.4), 7.44 (1H, t, J 7.2); m/z (ES$^+$) 226:228 (1:1) (M$^+$+H).

2-Bromo-6-cyclopentylpyridine (479 mg, 2.1 mmol) was coupled to 3-tributylstannyl-7-trifluoromethylimidazo[1,2-α]pyrimidine (1.4 mmol) by the method of Example 1 to give 3-(6-cyclopentylpyridin-2-yl)-7-trifluoromethylimidazo[1,2-α]pyrimidine (49 mg) as a white solid: $\delta_H$ (400 MHz, DMSO) 1.70–1.87 (6H, m), 2.10–2.16 (2H, m), 7.29 (1H, d, J 7.4), 7.80 (1H, d, J 7.0), 7.87 (1H, t, J 7.8), 7.95–7.97 (1H, m), 8.84 (1H, s), 10.50 (1H, d, J 6.7); m/z (ES$^+$) 332 (M$^+$+H).

EXAMPLE 14

3-(5-Methylpyridin-2-yl)-7-trifluoromethylimidazo[1,2-α]pyrimidine

2-Bromo-5-methylpyridine (1.29 g, 7.5 mmol) was coupled to 3-tributylstannyl-7-trifluoromethylimidazo[1,2-

α]pyrimidine (3.8 mmol) by the method of Example 1. Purification by chromatography on silica gel eluting with dichloromethane containing 1% methanol, then crystallisation from toluene/isohexane, gave 3-(5-methylpyridin-2-yl)-7-trifluoromethyl-imidazo[1,2-α]pyrimidine as a yellow solid: $\delta_H$ (400 MHz, CDCl$_3$) 10.48 (1H, d, J 7), 8.50–8.52 (1H, m), 8.46 (1H, s), 7.72 (1H, d, J 8), 7.61–7.65 (1H, m), 7.31 (1H, d, J 7); m/z (ES$^+$) 279 (M$^+$+H).

EXAMPLE 15

7-Trifluoromethyl-3-(5-trifluoromethylpyridin-2-yl)imidazo[1,2-α]pyrimidine

2-Bromo-5-trifluoromethylpyridine (1.70 g, 7.5 mmol) was coupled to 3-tributylstannyl-7-trifluoromethylimidazo[1,2-α]pyrimidine (3.8 mmol) by the method of Example 1. Purification by chromatography on silica gel eluting with dichloromethane containing 1% methanol, then crystallisation from toluene, gave 7-trifluoromethyl-3-(5-trifluoromethylpyridin-2-yl)imidazo[1,2-α]pyrimidine as a yellow solid: $\delta_H$ (400 MHz, CDCl$_3$) 10.52 (1H, d, J 7), 8.94–8.97 (1H, m), 8.63 (1H, s), 8.03–8.07 (1H, m), 7.96 (1H, d, J 9), 7.41 (1H, d, J 7); m/z (ES$^+$) 333 (M$^+$+H).

EXAMPLE 16

2-[4-(7-Trifluoromethylimidazo[1,2-α]pyrimidin-3-yl)pyrimidin-2-yl]-benzonitrile To a degassed solution of the product of Example 5 (70 mg, 0.23 mmol) in N,N-dimethylacetamide (2 ml) was added 2-tributylstannylbenzonitrile (183 mg, 0.46 mmol), lithium chloride (27.5 mg, 0.58 mmol), copper(I) iodide (5 mg) and dichloro[1,1'-bis(diphenylphosphino)ferrocene]palladium(II) (9 mg) and the mixture heated at 90° C. for 4 h. After cooling to ambient temperature the reaction was poured onto a strong cation exchange cartridge and eluted with methanol. The product was then eluted with a 2.0M solution of ammonia in methanol and evaporated in vacuo. The residue was dissolved in 5% methanol in dichloromethane and applied to two preparative TLC plates (silica gel) and eluted with 1:1 ethyl acetate in isohexane. The appropriate band was collected and processed to give a solid which was recrystallised from dichloromethane/ethyl acetate/isohexane to give 2-[4-(7-trifluoromethylimidazo[1,2-α]pyrimidin-3-yl)pyrimidin-2-yl]benzonitrile (10 mg) as a white solid: $\delta_H$ (400 MHz, CDCl$_3$) 7.50 (1H, d, J 7.4), 7.65–7.69 (1H, m), 7.78–7.82 (2H, m), 7.94 (1H, dd, J 7.8 and 1.2), 8.34 (1H, dd, J 8.0 and 1.0), 8.74 (1H, s), 8.97 (1H, d, J 5.5), 10.74 (1H, d, J 7.4); m/z (ES$^+$) 366 (M$^+$+H).

EXAMPLE 17

3-[3-(Thien-2-yl)-[1,2,4]thiadiazol-5-yl]-7-trifluoromethylimidazo[1,2-α]pyrimidine A solution of $^i$PrMgCl (2.0M in THF, 1.13 ml, 2.26 mmol) was added dropwise to a stirred suspension of 3-bromo-7-trifluoromethylimidazo[1,2-α]pyrimidine (547 mg, 2.06 mmol) in THF (20 ml) at −78° C. under N$_2$. The resulting solution was stirred at −78° C. for 15 min and then tributyltin chloride (670 µl, 2.47 mmol) was added. The reaction was warmed to 0° C. and stirred for 1 h. 5-Chloro-3-(thien-2-yl)-[1,2,4]thiadiazole (500 mg, 2.47 mmol) and tetrakis(triphenylphosphine)palladium(0) (237 mg, 0.21 mmol) were added and the reaction heated at reflux for 1 h. Copper(I) iodide (50 mg, 0.26 mmol) was added and heating continued for a further 1.5 h. The mixture was concentrated under reduced pressure while dry loading onto silica. The resulting crude residue was purified by column chromatography on silica, using 50% EtOAc in hexane as the eluent, and subsequent recrystallisation from dichloromethane/isohexanes gave 3-[3-(thien-2-yl)-[1,2,4]thiadiazol-5-yl]-7-trifluoromethylimidazo[1,2-α]pyrimidine (188 mg, 26%): $\delta_H$ (400 MHz, d$^6$-DMSO) 7.30 (1H, t, J 3.7), 7.83–7.90 (2H, m), 8.11 (1H, dd, J 3.7 and 1.1), 9.14 (1H, s), 10.20 (1H, d, J 7.1); m/z (ES$^+$) 353 (M$^+$).

EXAMPLE 18

3-[4-(Pyridin-3-yl)thien-2-yl]-7-trifluoromethylimidazo[1,2-α]pyrimidine

3-Bromo-7-trifluoromethylimidazo[1,2-α]pyrimidine (547 mg, 2.06 mmol) was reacted with 2,4-dibromothiophene over 1 h as described in Example 17. The resulting crude residue was purified by column chromatography on silica, using 40% EtOAc in isohexanes as the eluent, to yield 3-(4-bromothien-2-yl)-7-trifluoromethylimidazo[1,2-α]pyrimidine (104 mg, 15%) after recrystallisation from dichloromethane/isohexanes: $\delta_H$ (400 MHz, d$^6$-DMSO) 7.57 (1H, d, J 8.3), 7.72 (1H, d, J 1.6), 8.10 (1H, d, J 1.6), 8.34 (1H, s), 9.34 (1H, d, J 7.0); m/z (ES$^+$) 347, 349 (1:1) (M$^+$).

A mixture of 3-(4-bromothien-2-yl)-7-trifluoromethylimidazo[1,2-α]pyrimidine (104 mg, 0.3 mmol), pyridine-3-boronic acid-1,3-propanediol cyclic ester (73 g, 0.45 mmol), cesium carbonate (0.29 g, 0.9 mmol) and tetrakis(triphenylphosphine)palladium(0) (34 mg, 0.03 mmol) in 1,4-dioxane (5 ml) and H$_2$O (0.5 ml) were degassed with a stream of N$_2$ for 10 min. The reaction mixture was then heated at reflux for 1 h. The mixture was concentrated under reduced pressure to remove the organic solvents and H$_2$O (20 ml) was added. The organics were extracted with dichloromethane (2×50 ml) and concentrated under reduced pressure while dry loading onto silica. The resulting crude residue was purified by column chromatography on silica using 70% EtOAc in hexanes containing 1% Et$_3$N and 1% MeOH as the eluent. The resulting material was taken up in MeOH and was poured onto a strong cation exchange cartridge and eluted with methanol. The product was then eluted with 2.0M NH$_3$ in MeOH and evaporated to give 3-[4-(pyridin-3-yl)thien-2-yl]-7-trifluoromethylimidazo[1,2-α]pyrimidine (83 mg, 80%): $\delta_H$ (400 MHz, d$^6$-DMSO) 7.46–7.53 (1H, m), 7.60 (1H, d, J 7.1), 8.18 (1H, d, J 1.5), 8.22–8.30 (1H, m), 8.26 (1H, d, J 1.5), 8.42 (1H, s), 8.56–8.60 (1H, m), 9.10 (1H, s), 10.20 (1H, d, J 7.1); m/z (ES$^+$) 346 (M$^+$).

EXAMPLE 19

3-[5-(Pyridin-3-yl)thien-3-yl]-7-trifluoromethylimidazo[1,2-α]pyrimidine

A mixture of 2,4-dibromothiophene (3 g, 12.4 mmol) and pyridine-3-boronic acid-1,3-propanediol cyclic ester (2.22 g, 13.6 mmol) in EtOH (30 ml) and toluene (30 ml) together with 2N Na$_2$CO$_3$ solution (12.4 ml) was degassed with a stream of N$_2$ for 10 min. Tetrakis-(triphenylphosphine)palladium(0) (0.25 g, 0.22 mmol) was added and the reaction heated at reflux for 4 h. The mixture was concentrated under reduced pressure to remove the organic solvents and H$_2$O (100 ml) was added. The organics were extracted with EtOAc (200 ml) and then washed with brine (75 ml), dried (MgSO$_4$), and concentrated under vacuum. The resulting crude residue was purified by column chromatography on silica using 70% diethyl ether in hexane as the eluent to yield 3-(4-bromothien-2-yl)pyridine (2.15 g, 75%): $\delta_H$ (360 MHz, CDCl$_3$) 7.26 (1H, s), 7.32 (1H, dd, J 8.6 and 4.9), 7.81 (1H, dt, J 8.6 and 1.7), 8.56 (1H, s), 8.86 (1H, s); m/z (ES$^+$) 240, 242 (1:1) (M$^+$+H).

A mixture of 3-(4-bromothien-2-yl)pyridine (948 mg, 4.0 mmol), bis-(neopentyl glycolato)diborane (985 g, 4.36 mmol), KOAc (1.16 g, 11.8 mmol) and Pd(dppf)Cl$_2$ (161 mg, 5 mol %) in 1,4-dioxane (50 ml) was degassed with a stream of N$_2$ for 10 min and then heated at 110° C. for 3 h. The reaction mixture was concentrated under reduced pressure and H$_2$O (100 ml) was added, and then was extracted with diethyl ether (2×75 ml). The combined ethereal extracts were washed with brine (50 ml) and dried (MgSO$_4$) to yield 3-[4-(5,5-dimethyl-[1,3,2]dioxaborinan-2-yl)thien-2-yl] pyridine (927 mg, 85%): $\delta_H$ (360 MHz, CDCl$_3$) 1.03 (6H, s), 3.77 (4H, s), 7.30 (1H, dd, J 7.6 and 4.4), 7.62 (1H, s), 7.83 (1H, s), 7.88 (1H, dt, J 7.6 and 1.8), 8.51 (1H, s), 8.91 (1H, s); m/z (ES$^+$) 273, 274 (1:4) (M$^+$+H).

A mixture of 3-bromo-7-trifluoromethylimidazo[1,2-α] pyrimidine (250 mg, 0.94 mmol), the foregoing boronate ester (537 mg, 1.88 mmol) and K$_3$PO$_4$ (866 mg, 3.76 mmol) in N,N-dimethylacetamide (6 ml) was degassed with a stream of N$_2$ for 5 min and then tetrakis(triphenylphosphine) palladium(0) (109 mg, 10 mol %) was added and the reaction was heated at 60° C. for 1 h. EtOAc (100 ml) was added and the mixture washed with H$_2$O (3×100 ml) and brine (100 ml), dried (MgSO$_4$) and concentrated under reduced pressure while dry loading onto silica. The residue was purified by column chromatography on silica using 70% EtOAc in hexanes containing 1% Et$_3$N and 1% MeOH as the eluent. The resulting material was taken up in MeOH and was poured on to a strong cation exchange cartridge and eluted with methanol. The product was then eluted with 2.0M NH$_3$ in MeOH and evaporated while dry loading onto silica. Subsequent purification by column chromatography on silica using 70% EtOAc in dichloromethane gave 3-[5-(pyridin-3-yl)thien-3-yl]-7-trifluoromethylimidazo[1,2-α] pyrimidine (129 mg, 40%): $\delta_H$ (400 MHz, d$^6$-DMSO) 7.46–7.54 (1H, m), 7.58 (1H, d, J 7.1), 8.16–8.20 (1H, m), 8.20 (1H, s), 8.41 (1H, s), 8.56 (1H, dd, J 4.7 and 1.4), 9.04 (1H, s), 9.45 (1H, d, J 7.1); m/z (ES$^+$) 347 (M$^+$+H).

EXAMPLE 20

3-[4-(Pyridin-3-yl)thiazol-2-yl]-7-trifluoromethylimidazo[1,2-α]pyrimidine

A mixture of 2-amino-4-trifluoromethylpyrimidine (2.0 g, 12.2 mmol) and N,N-dimethylformamide dimethyl acetal (1.79 ml, 13.5 mmol) in toluene (50 ml) was heated at reflux for 1 h and then concentrated under reduced pressure. The resulting formamide was treated with ethyl bromoacetate (1.49 ml, 13.4 mmol) in toluene (60 ml) at reflux for 12 h and then concentrated under reduced pressure. The product was treated with saturated sodium hydrogencarbonate solution (50 ml) and extracted with EtOAc (3×50 ml). The combined organic extracts were washed with brine (50 ml), dried (MgSO$_4$) and then concentrated while dry loading onto silica. Subsequent purification by column chromatography on silica using diethyl ether gave ethyl 7-trifluoromethylimidazo[1,2-α]pyrimidine-3-carboxylate (2.01 g, 64%): $\delta_H$ (360 MHz, CDCl$_3$) δ 1.45 (3H, t, J 7.1), 4.47 (2H, q, J 7.1), 7.44 (1H, d, J 7.1), 8.60 (1H, s), 9.77 (1H, d, J 7.1); m/z (ES$^+$) 347 (M$^+$+H).

A mixture of the foregoing ethyl ester (1.58 g, 6.1 mmol) and ammonia solution (25%, 50 ml) in EtOH (200 ml) was stirred at room temperature for 72 h. The organic solvent was removed under reduced pressure and the aqueous extracted with EtOAc (3×250 ml). The combined organic extracts were washed with brine (100 ml), dried (MgSO$_4$) and then concentrated while dry loading onto silica. Subsequent purification by column chromatography on silica using EtOAc/ether gave 7-trifluoromethylimidazo[1,2-α] pyrimidine-3-carboxamide (160 mg, 10%): $\delta_H$ (360 MHz, d$^6$-DMSO) 7.70 (1H, d, J 7.1), 7.72 (1H, s), 8.28 (1H, s), 8.69 (1H, s), 10.02 (1H, d, J 7.1).

Lawesson's reagent (281 mg, 0.7 mmol) was added to a stirred suspension of the foregoing amide (160 mg, 0.7 mmol) in toluene (16 ml). The resulting mixture was heated at reflux for 2.5 h and then concentrated under reduced pressure while dry loading onto silica. Subsequent purification by column chromatography on silica using firstly diethyl ether and then EtOAc/ether gave 7-trifluoromethylimidazo[1,2-α]pyrimidine-3-carbothioamide (160 mg, 93%): $\delta_H$ (360 MHz, d$^6$-DMSO) δ 7.80 (1H, d, J 7.2), 8.70 (1H, s), 9.73 (1H, s), 9.82 (1H, s), 10.87 (1H, d, J 7.2).

3-(Bromoacetyl)pyridinium bromide (41 mg, 0.14 mmol) was added to a stirred solution of the foregoing thioamide (24 mg, 0.1 mmol) in DMF (1 ml) at room temperature under N$_2$. The reaction was warmed to 60° C. for 1 h and then concentrated under reduced pressure while azeotroping with xylene (20 ml). The crude residue was taken up in EtOAc (50 ml), washed with saturated sodium hydrogencarbonate solution (20 ml) and concentrated under reduced pressure while dry loading onto silica. Subsequent purification by column chromatography on silica using 70% EtOAc in hexanes containing 1% Et$_3$N and 1% MeOH as the eluent gave 3-[4-(pyridin-3-yl)thiazol-2-yl]-7-trifluoromethylimidazo[1,2-α]pyrimidine (33 mg, 97%): $\delta_H$ (400 MHz, d$^6$-DMSO) 7.52–7.60 (1H, m), 7.80 (1H, d, J 7.1), 8.43 (1H, s), 8.50 (1H, dt, J 7.8 and 2.0), 8.62 (1H, m), 8.83 (1H, s), 9.39 (1H, s), 10.33 (1H, d, J 7.1); m/z (ES$^+$) 347 (M$^+$).

EXAMPLE 21

2-{6-[7-(1-Hydroxy-1-methylethyl)imidazo[1,2-α] pyrimidin-3-yl]pyridin-2-yl}benzonitrile A solution of 3-hydroxy-3-methyl-2-butanone (10.75 ml, 100 mmol) and triethylamine (21 ml, 150 mmol) in dichloromethane (125 ml) was treated with acetic anhydride (11.8 ml, 125 mmol) then with 4-dimethylaminopyridine (610 mg, 5 mmol) and the reaction was stirred at ambient temperature for 14 h. Methanol (10 ml) was added and stirring continued for 30 min before concentrating the reaction in vacuo. The residue was dissolved in ether (300 ml) and washed with 0.5N hydrochloric acid (2×300 ml), water, saturated aqueous sodium hydrogencarbonate, dried over anhydrous magnesium sulfate, filtered and evaporated to dryness to afford acetic acid 1,1-dimethyl-2-oxopropyl ester as a yellow liquid (13.5 g, 94%): $\delta_H$ (400 MHz, CDCl$_3$) 1.46 (6H, s), 2.09 (3H, s), 2.12 (3H, s).

Boron trifluoride etherate (17.03 g, 120.0 mmol) was added drop-wise over 15 min to a cooled (−40° C.) solution of triethyl orthoformate (14.82 g, 100.0 mmol) in dichloromethane (50 ml). Stirring was continued for 10 min then the solution was transferred to an ice-water bath and stirred at 0° C. for 20 min. The mixture was cooled to −78° C., and acetic acid 1,1-dimethyl-2-oxopropyl ester (7.21 g, 50.0 mmol) added followed by drop-wise addition of N,N-diisopropylethylamine (19.39 g, 150.0 mmol) over 15 min.

Stirring was continued for 1 h then the solution was poured onto a vigorously stirred mixture of saturated sodium hydrogencarbonate solution (500 ml) and dichloromethane (200 ml). The organic phase was separated, washed with ice-cold 1N sulfuric acid solution (2×500 ml) and ice-cold water (2×500 ml), dried over anhydrous sodium sulfate solution and evaporated to give acetic acid 4,4-diethoxy-1,1-dimethyl-2-oxobutyl ester (12.32 g, 100%) as a yellow oil.

Sodium methoxide (3.11 g, 57.5 mmol) was added to a stirred solution of 2-aminoimidazole hemisulfate (6.61 g, 25.0 mmol) and acetic acid 4,4-diethoxy-1,1-dimethyl-2-oxobutyl ester (12.32 g, 50.0 mmol) in ethanol (50 ml). The mixture was heated under reflux for 16 h, allowed to cool to ambient temperature then pre-adsorbed directly onto silica. Purification by silica gel chromatography eluting with dichloromethane and 1% conc. ammonia on a gradient of methanol (1–3%) gave 2-(imidazo[1,2-α]pyrimidin-7-yl)propan-2-ol as an orange solid: $\delta_H$ (400 MHz, CDCl$_3$) 1.60 (6H, s), 5.31 (1H, s), 7.10 (1H, d, J 7), 7.54 (1H, d, J 1), 7.72 (1H, d, J 1), 8.49 (1H, d, J 7).

2-(Imidazo[1,2-α]pyrimidin-7-yl)propan-2-ol was brominated as described in Example 1 to give 2-(3-bromoimidazo[1,2-α]pyrimidin-7-yl)-propan-2-ol as an off-white solid: $\delta_H$ (400 MHz, CDCl$_3$) 1.62 (6H, s), 4.20 (1H, s), 7.17 (1H, d, J 7), 7.76 (1H, s), 8.40 (1H, d, J 7).

Triethylsilyl trifluoromethanesulfonate (4.85 ml, 21.5 mmol) was added dropwise over 15 min to a cooled (−50° C.) solution of 2-(3-bromoimidazo[1,2-α]pyrimidin-7-yl)propan-2-ol (5.0 g, 19.5 mmol) and diisopropylethylamine (4.76 ml, 27.5 mmol) in dichloromethane (150 ml). The mixture was stirred for 20 min then allowed to warm to ambient temperature overnight. The reaction mixture was diluted with dichloromethane (100 ml) and washed with 1N hydrochloric acid (100 ml) and water (100 ml), dried over anhydrous magnesium sulfate, filtered and evaporated. The red oil was purified by dry flash column chromatography on silica eluting with dichloromethane on a gradient of methanol (0–3%). Collecting the appropriate fractions gave 3-bromo-7-(1-methyl-1-triethylsilanyloxyethyl)imidazo[1,2-α]pyrimidine as a pale yellow oil which crystallised on standing (6.21 g, 86%): $\delta_H$ (400 MHz, CDCl$_3$) 0.64 (6H, q, J 8), 0.97 (9H, t, J 8), 7.50 (1H, d, J 7), 7.72 (1H, s), 8.35 (1H, d, J 7).

7-(1-Methyl-1-triethylsilanyloxyethyl)-3-tributylstannylimidazo[1,2-α]pyrimidine was prepared from 3-bromo-7-(1-methyl-1-triethylsilanyloxyethyl)imidazo[1,2-α]pyrimidine in the same way as described in Example 1: m/z (ES$^+$) 578, 580, 582 (M$^+$+H).

2,6-Dibromopyridine was coupled with 7-(1-methyl-1-triethylsilanyloxyethyl)-3-tributylstannylimidazo[1,2-α]pyrimidine by the method of Example 1 to afford 3-(6-bromopyridin-2-yl)-7-(1-methyl-1-triethylsilanyloxyethyl)imidazo[1,2-α]pyrimidine as an orange oil: $\delta_H$ (360 MHz, CDCl$_3$) 0.69 (6H, q, J 8), 0.99 (9H, q, J 8), 1.69 (6H, s), 7.34 (1H, d, J 7), 7.54–7.62 (2H, m), 7.69 (1H, d, J 8), 8.29 (1H, s), 10.00 (1H, d, J 7).

A mixture of 2-bromobenzonitrile (18.2 g, 100 mmol), potassium acetate (19.63 g, 200 mmol), bis(pinacolato)diboron (27.93 g, 110 mmol) and dichloro[1,1'-bis(diphenylphosphino)ferrocene]palladium(II) dichloromethane adduct (1.63 g, 2 mmol) in 1,4-dioxane (300 ml containing 6 ml dimethylsulfoxide) was degassed with nitrogen for 1 h then heated at 90° C. for) 14 h. The reaction was cooled to ambient temperature and then concentrated in vacuo. The residue was stirred with 2N sodium hydroxide (1 l) for 10 min then filtered. The filtrate was extracted with diethyl ether (2×300 ml) and the organics discarded. The aqueous component was cooled to 0° C. then treated with 5N hydrochloric acid added dropwise over 15 min until pH 8. The aqueous phase was extracted with ethyl acetate (2×200 ml), the combined organics were dried over anhydrous sodium sulfate, filtered and evaporated to afford 2-(4,4,5,5-tetramethyl-[1,3,2]dioxaborolan-2-yl)benzonitrile (12.5 g, 55%) as a pale brown solid: $\delta_H$ (400 MHz, CDCl$_3$) 1.38 (12H, s), 7.47–7.58 (2H, m), 7.69 (1H, dd, J 9 and 2), 7.88 (1H, dd, J 9 and 2).

3-(6-Bromopyridin-2-yl)-7-(1-methyl-1-triethylsilanyloxyethyl)-imidazo[1,2-α]pyrimidine was coupled to 2-(4,4,5,5-tetramethyl-[1,3,2]dioxaborolan-2-yl)benzonitrile following the procedure in Example 2 to give 2-{6-[7-(1-methyl-1-triethylsilanyloxyethyl)imidazo[1,2-α]pyrimidin-3-yl]pyridin-2-yl}benzonitrile as an orange oil.

To a solution of crude 2-{6-[7-(1-methyl-1-triethylsilanyloxy-ethyl)imidazo[1,2-α]pyrimidin-3-yl]pyridin-2-yl}benzonitrile in ethanol (3 ml) was added 3 drops of concentrated hydrochloric acid and the mixture left to stir at ambient temperature for 18 h. The solvent was evaporated and the residue made basic by the addition of saturated aqueous sodium hydrogencarbonate. The aqueous phase was diluted with water (30 ml) and extracted with ethyl acetate (2×75 ml). The combined organic phase was washed with water (30 ml) and brine (30 ml), dried over anhydrous sodium sulfate, filtered and evaporated to give an orange oil. This oil was purified on silica eluting with dichloromethane (+1% 0.880 ammonia) on a gradient of methanol (1–3%). Collecting the appropriate fractions followed by recrystallisation from ethyl acetate/isohexane gave 2-{6-[7-(1-hydroxy-1-methylethyl)imidazo[1,2-α]pyrimidin-3-yl]pyridin-2-yl}benzonitrile as a white solid: $\delta_H$ (360 MHz, CDCl$_3$) 1.63 (6H, s), 4.52 (1H, s), 7.16 (1H, d, J 7), 7.55–7.62 (2H, m), 7.74–7.96 (5H, m), 8.36 (1H, s), 10.37 (1H, d, J 7); m/z (ES$^+$) 356 (M$^+$+H).

EXAMPLE 22

5-Fluoro-2-{6-[7-(1-hydroxy-1-methylethyl)imidazo[1,2-α]pyrimidin-3-yl]pyridin-2-yl}benzonitrile 3-(6-Bromopyridin-2-yl)-7-(1-methyl-1-triethylsilanyloxyethyl)-imidazo[1,2-α]pyrimidine (336 mg, 0.75 mmol) was coupled to 5-fluoro-2-(4,4,5,5-tetramethyl-[1,3,2]dioxaborolan-2-yl)benzonitrile (synthesised from 2-bromo-5-fluorobenzonitrile as in Example 21) following the procedure in Example 2 to give 5-fluoro-2-{6-[7-(1-methyl-1-triethylsilanyloxyethyl)imidazo[1,2-α]pyrimidin-3-yl]pyridin-2-yl}benzonitrile as an orange oil.

5-Fluoro-2-{6-[7-(1-methyl-1-triethylsilanyloxyethyl)imidazo[1,2-α]pyrimidin-3-yl]pyridin-2-yl}benzonitrile was deprotected using the procedure in Example 21 to give 5-fluoro-2-{6-[7-(1-hydroxy-1-methylethyl)imidazo[1,2-α]pyrimidin-3-yl]pyridin-2-yl}benzonitrile (80 mg, 29%) as a white solid: $\delta_H$ (400 MHz, CDCl$_3$) 1.63 (6H, s), 4.48 (1H, s), 7.16 (1H, d, J 7), 7.46 (1H, ddd, J 8, 5 and 1), 7.54 (1H, d, J 8), 7.59 (1H, dd, J 8 and 1), 7.80 (1H, dd, J 8 and 8), 7.86 (1H, dd, J 8 and 1), 7.94 (1H, dd, J 8 and 8), 8.37 (1H, s), 10.30 (1H, d, J 7); m/z (ES$^+$) 374 (M$^+$+H).

EXAMPLE 23

3-{6-[7-(1-Hydroxy-1-methylethyl)imidazo[1,2-α]pyrimidin-3-yl]pyridin-2-yl}thiophene-2-carbonitrile 3-(4,4,5,5-Tetramethyl-[1,3,2]dioxaborolan-2-yl)thiophene-2-carbonitrile was synthesised following the procedure in Example 21 from 3-bromo-2-cyanothiophene. 3-(6-Bromopyridin-2-yl)-7-(1-methyl-1-triethylsilanyloxyethyl)imidazo[1,2-α]pyrimidine was coupled to 3-(4,4,5,5-tetramethyl-[1,3,2]dioxaborolan-2-yl)thiophene-2-carbonitrile following the procedure in Example 2 to give 3-{6-[7-(1-methyl-1-triethylsilanyloxyethyl)imidazo[1,2-α]pyrimidin-3-yl]pyridin-2-yl}thiophene-2-carbonitrile as an orange oil.

3-{6-[7-(1-Methyl-1-triethylsilanyloxyethyl)imidazo[1,2-α]pyrimidin-3-yl]pyridin-2-yl}thiophene-2-carbonitrile was deprotected using the procedure in Example 21 to give 3-{6-[7-(1-hydroxy-1-methylethyl)imidazo[1,2-α]pyrimidin-3-yl]pyridin-2-yl}thiophene-2-carbonitrile (159 mg, 59%) as a pale brown solid: $\delta_H$ (360 MHz, CDCl$_3$) 1.64 (6H, s), 4.53 (1H, s), 7.20 (1H, d, J 7), 7.59 (1H, d, J 5), 7.67–7.71 (2H, m), 7.84 (1H, d, J 8), 7.92 (1H, dd, J 8 and 8), 8.35 (1H, s), 10.36 (1H, d, J 7); m/z (ES$^+$) 362 (M$^+$+H).

EXAMPLE 24

4-Fluoro-2-{6-[7-(1-hydroxy-1-methylethyl)imidazo[1.2-α]pyrimidin-3-yl]pyridin-2-yl}benzonitrile 4-Fluoro-2-(4,4,5,5-tetramethyl-[1,3,2]dioxaborolan-2-yl)benzonitrile was synthesised from 2-bromo-4-fluorobenzonitrile following the procedure in Example 22. 3-(6-Bromopyridin-2-yl)-7-(1-methyl-1-triethylsilanyloxyethyl)imidazo[1,2-α]pyrimidine was coupled to 4-fluoro-2-(4,4,5,5-tetramethyl-[1,3,2]dioxaborolan-2-yl)benzonitrile following the procedure in Example 2 to give 4-fluoro-2-{6-[7-(1-methyl-1-triethylsilanyloxyethyl)imidazo[1,2-α]pyrimidin-3-yl]pyridin-2-yl}benzonitrile as an orange oil.

4-Fluoro-2-{6-[7-(1-methyl-1-triethylsilanyloxyethyl)imidazo[1,2-α]pyrimidin-3-yl]pyridin-2-yl}benzonitrile was deprotected using the procedure in Example 21 to give 4-fluoro-2-{6-[7-(1-hydroxy-1-methylethyl)imidazo[1,2-α]pyrimidin-3-yl]pyridin-2-yl}benzonitrile (195 mg, 65%) as a white solid: $\delta_H$ (360 MHz, CDCl$_3$) 1.63 (6H, s), 4.48 (1H, s), 7.18 (1H, d, J 7), 7.29 (1H, ddd, J 8, 2 and 1), 7.52 (1H, dd, J 9 and 2), 7.59 (1H, dd, J 8 and 1), 7.87–7.98 (3H, m), 8.37 (1H, s), 10.31 (1H, d, J 7); m/z (ES$^+$) 374 (M$^+$+H).

EXAMPLE 25

3-(6-Bromopyridin-2-yl)-7-(1-fluoro-1-methylethyl)imidazo[1,2-α]pyrimidine

3-Fluoro-3-methylbutan-2-one was prepared from 3-bromo-3-methylbutan-2-one as described by Fry and Migron (*Tetrahedron Lett.*, 1979, 3357–3360) to give 3-fluoro-3-methylbutan-2-one as a colourless oil (contaminated with 6% 3-methyl-3-buten-2-one): bp 74–6° C.; $\delta_H$ (360 MHz, CDCl$_3$) 1.45 (6H, d, J 22), 2.28 (3H, d, J 5).

3-Fluoro-3-methylbutan-2-one (5.75 g, 55.2 mmol) was converted to 1,1-diethoxy-4-fluoro-4-methylpentan-3-one as described in Example 21 and condensed with 2-aminoimidazole hemisulfate as in Example 21 to give 7-(1-fluoro-1-methylethyl)imidazo[1,2-α]pyrimidine as an orange oil which crystallised on standing (7.41 g, 75%): $\delta_H$ (400 MHz, CDCl$_3$) 1.77 (6H, d, J 22), 7.21 (1H, dd, J 7 and 2), 7.54 (1H, d, J 1), 7.79 (1H, d, J 1), 8.45 (1H, d, J 7).

7-(1-Fluoro-1-methylethyl)imidazo[1,2-α]pyrimidine (2.0 g, 11.1 mmol) was brominated as described in Example 1 to give 3-bromo-7-(1-fluoro-1-methylethyl)imidazo[1,2-α]pyrimidine (1.65 g, 58%) as an off-white solid: $\delta_H$ (360 MHz, CDCl$_3$) 1.78 (6H, d, J 22), 7.35 (1H, d, J 7 and 2), 7.77 (1H, s), 8.42 (1H, d, J 7).

7-(1-Fluoro-1-methylethyl)-3-tributylstannylimidazo[1,2-α]pyrimidine was prepared from 3-bromo-7-(1-fluoro-1-methyl-ethyl)imidazo[1,2-α]pyrimidine (1.13 g, 4.38 mmol) in the same way as described in Example 1: m/z (ES$^+$) 580, 582, 584 (M$^+$+H).

2,6-Dibromopyridine was coupled with 7-(1-fluoro-1-methylethyl)-3-tributylstannylimidazo[1,2-α]pyrimidine by the method of Example 1 to afford 3-(6-bromopyridin-2-yl)-7-(1-fluoro-1-methylethyl)imidazo[1,2-α]pyrimidine (1.0 g, 68%) as a pale yellow solid: $\delta_H$ (360 MHz, CDCl$_3$) 1.81 (6H, d, J 22), 7.37 (1H, d, J 8), 7.42 (1H, dd, J 7 and 2), 7.61 (1H, dd, J 8 and 8), 7.71 (1H, dd, J 8 and 1), 8.33 (1H, s), 10.09 (1H, d, J 7).

EXAMPLE 26

2-{6-[7-(1-Fluoro-1-methylethyl)imidazo[1,2-α]pyrimidin-3-yl]pyridin-2-yl}benzonitrile The product of Example 25 (0.34 g, 1.0 mmol) was coupled to 2-(4,4,5,5-tetramethyl-[1,3,2]dioxaborolan-2-yl)benzonitrile following the procedure in Example 2 to give 2-{6-[7-(1-fluoro-1-methyl-ethyl)imidazo[1,2-α]pyrimidin-3-yl]pyridin-2-yl}benzonitrile (0.133 g, 37%) as a white solid: $\delta_H$ (360 MHz, CDCl$_3$) 1.80 (6H, d, J 22), 7.38 (1H, dd, J 7 and 2), 7.59 (1H, ddd, J 8, 7 and 1), 7.75 (1H, ddd, J 8, 7 and 1), 7.80–7.96 (5H, m), 8.38 (1H, s), 10.36 (1H, d, J 7); m/z (ES$^+$) 358 (M$^+$+H).

EXAMPLE 27

2-{6-[7-(1-Cyano-1-methylethyl)imidazo[1,2-α]pyrimidin-3-yl]pyridin-2-yl}benzonitrile 2,6-Dibromopyridine (0.47 g, 2.0 mmol), 2-(4,4,5,5-tetramethyl-[1,3,2]dioxaborolan-2-yl)benzonitrile (0.69 g, 3.0 mmol) and potassium phosphate (0.85 g, 4.0 mmol) were dissolved in N,N-dimethylformamide (10 ml) and degassed with nitrogen for 15 min. Tetrakis(triphenylphosphine)palladium(0) (70 mg, 0.06 mmol) was added then the mixture heated at 80° C. for 16 h. The mixture was allowed to cool to ambient temperature, diluted with water (200 ml) and extracted into ethyl acetate (2×150 ml). The combined organics were washed with brine (200 ml), dried over anhydrous sodium sulfate and evaporated to give a yellow oil. Purification by flash column chromatography on silica eluting with isohexane on a gradient of ethyl acetate (10–30%) gave 2-(6-bromopyridin-2-yl)benzonitrile (0.518 g, 100%) as a waxy solid: $\delta_H$ (360 MHz, CDCl$_3$) 7.53–7.57 (2H, m), 7.68–7.72 (2H, m), 7.80 (1H, d, J 8), 7.86–7.90 (1H, m).

2,2-Dimethyl-3-oxobutyronitrile was prepared from 3-methyl-2-butanone as described by Rasmussen (*Synthesis*, 1973, 682): bp 74–6° C. (30 mmHg); $\delta_H$ (360 MHz, CDCl$_3$) 1.51 (6H, s), 2.43 (3H, s).

2,2-Dimethyl-3-oxobutyronitrile was converted to 5,5-diethoxy-2,2-dimethyl-3-oxopentanenitrile then condensed with 2-aminoimidazole hemisulfate following the procedure in Example 21 to give 2-(imidazo[1,2-α]pyrimidin-7-yl)-2-methylpropionitrile (5.15 g, 69%) as a white solid: $\delta_H$ (400 MHz, CDCl$_3$) 1.84 (6H, s), 7.27 (1H, d, J 7), 7.58 (1H, d, J 1), 7.84 (1H, d, J 1), 8.49 (1H, d, J 7).

2-(Imidazo[1,2-α]pyrimidin-7-yl)-2-methylpropionitrile (100 mg, 0.51 mmol), 2-(6-bromopyridin-2-yl)benzonitrile (159 mg, 0.61 mmol) and cesium carbonate (332 mg, 1.02 mmol) were suspended in 1,4-dioxane and degassed with nitrogen for 20 min. Tetrakis(triphenylphosphine)-palladium(0) (29 mg, 0.025 mmol) was added and the mixture was heated at 80° C. for 3 h. The reaction was cooled to ambient temperature then diluted with water (60 ml) and extracted with ethyl acetate (2×100 ml). The combined organic extracts were washed with brine (70 ml), dried over anhydrous sodium sulfate, filtered and evaporated to give a pale yellow oil. The oil was purified by chromatography on silica gel eluting with dichloromethane on a gradient of methanol (0–1%). Collecting appropriate fractions followed by recrystallisation from ethyl acetate/isohexane gave 2-{6-[7-(1-cyano-1-methylethyl)imidazo[1,2-α]pyrimidin-3-yl]pyridin-2-yl}benzonitrile (70 mg, 38%) as a white solid: $\delta_H$ (360 MHz, CDCl$_3$) 1.86 (6H, s), 7.43 (1H, d, J 7), 7.59–7.63 (2H, m), 7.80 (2H, m), 7.86–7.97 (3H, m), 8.42 (1H, s), 10.44 (1H, d, J 7); m/z (ES$^+$) 365 (M$^+$+H).

EXAMPLE 28

2-[6-(7-tert-Butylimidazo[1,2-α]pyrimidin-3-yl)pyridin-2-yl]-5-fluorobenzonitrile 2,6-Dibromopyridine (1.17 g, 5.0 mmol) was coupled to 5-fluoro-2-(4,4,5,5-tetramethyl-[1,3,2]dioxaborolan-2-yl)benzonitrile (synthesised as in Example 22) (1.48 g, 6.0 mmol) as described in Example 27 to afford 2-(6-bromopyridin-2-yl)-5-fluorobenzonitrile (0.69 g, 50%) as a white solid: $\delta_H$ (400 MHz, CDCl$_3$) 1.42 (9H, s), 6.96 (1H, d, J 7), 7.45 (1H, d, J 1), 7.72 (1H, d, J 1), 8.33 (1H, d, J 7).

3,3-Dimethylbutan-2-one was converted to 1,1-diethoxy-4,4-dimethylpentan-3-one as described in Example 21 and condensed with 2-aminoimidazole hemisulfate as described in Example 21 to give 7-tert-butylimidazo[1,2-α]pyrimidine as a pale-orange solid: $\delta_H$ (400 MHz, CDCl$_3$) 1.42 (9H, s), 6.96 (1H, d, J 7), 7.45 (1H, d, J 1), 7.72 (1H, d, J 1), 8.33 (1H, d, J 7).

7-tert-Butylimidazo[1,2-α]pyrimidine was coupled with 2-(6-bromopyridin-2-yl)-5-fluorobenzonitrile as described in Example 27 to give 2-[6-(7-tert-butylimidazo[1,2-α]pyrimidin-3-yl)pyridin-2-yl]-5-fluorobenzonitrile (0.235 g, 63%) as a white powder: $\delta_H$ (360 MHz, CDCl$_3$) 1.43 (9H, s), 7.05 (1H, d, J 7), 7.37–7.73 (6H, m), 7.81 (1H, s), 7.85 (1H, dd, J 8 and 1), 8.75 (1H, d, J 7); m/z (ES$^+$) 371 (M$^+$+H).

EXAMPLE 29

4-Fluoro-2-[6-(7-trifluoromethylimidazo[1,2-α]pyrimidin-3-yl)pyridin-2-yl]benzonitrile 4-Fluoro-2-(4,4,5,5-tetramethyl-[1,3,2]dioxaborolan-2-yl)-benzonitrile (synthesised as in Example 24) was coupled with 2,6-dibromopyridine as described in Example 27 to give 2-(6-bromopyridin-2-yl)-4-fluorobenzonitrile as a white solid: $\delta_H$ (360 MHz, d$_6$-DMSO) 7.55–7.60 (1H, m), 7.67–7.84 (2H, m), 7.89–8.02 (2H, m), 8.12 (1H, dd, J 9 and 6).

3-Tributylstannyl-7-trifluoromethylimidazo[1,2-α]pyrimidine was coupled with 2-(6-bromopyridin-2-yl)-4-fluorobenzonitrile as in Example 1 to give 4-fluoro-2-[6-(7-trifluoromethylimidazo[1,2-α]pyrimidin-3-yl)pyridin-2-yl]benzonitrile as a pale pink solid (16 mg, 14%): $\delta_H$ (400 MHz, CDCl$_3$) 7.29–7.32 (1H, m), 7.40 (1H, d, J 7), 7.53 (1H, dd, J 9 and 2), 7.66 (1H, dd, J 8 and 1), 7.88–8.03 (3H, m), 8.59 (1H, s), 10.56 (1H, d, J 7).

EXAMPLE 30

3-(2-Fluoropyridin-5-yl)-7-trifluoromethylimidazo[1,2-α]pyrimidine

To a degassed solution of 3-tributylstannyl-7-trifluoromethylimidazo[1,2-α]pyrimidine was added 5-bromo-2-fluoropyridine (0.128 ml, 1.3 mmol) and tetrakis(triphenylphosphine)palladium(0) (173 mg, 0.15 mmol) and the mixture heated at reflux for 5 h. The crude reaction was washed with water and extracted with ethyl acetate. After adding isohexane a dark solid was collected by suction filtration. The solid was adsorbed onto silica and purified by chromatography on silica gel, eluting with isohexane on a gradient of ethyl acetate (20–60%), to give 3-(2-fluoropyridin-5-yl)-7-trifluoromethylimidazo[1,2-α]pyrimidine (150 mg) as a dark solid: $\delta_H$ (500 MHz, CDCl$_3$) 7.12 (1H, m), 7.30 (1H, d, J 7), 7.99–8.02 (1H, m), 8.10 (1H, s), 8.46 (1H, s), 8.72 (1H, d, J 7); m/z (ES$^+$) 282, 283 (M$^+$+H).

EXAMPLE 31

3-(2-Phenylpyridin-5-yl)-7-trifluoromethylimidazo[1,2-α]pyrimidine

3-Tributylstannyl-7-trifluoromethylimidazo[1,2-α]pyrimidine was reacted with 5-bromo-2-phenylpyridine (prepared according to the procedure of Tilley and Zawoiski, *J. Org. Chem.*, 1988, 53(2), 386–90) by the method of Example 1 to afford 3-(2-phenylpyridin-5-yl)-7-trifluoromethylimidazo[1,2-α]pyrimidine as a yellow solid: $\delta_H$ (400 MHz, CDCl$_3$) 7.30 (1H, d, J 7), 7.47–7.56 (3H, m), 7.96 (2H, m), 8.09 (2H, dd, J 8 and 1), 8.19 (1H, s), 8.83 (1H, d, J 7), 8.93 (1H, d, J 2); m/z (ES$^+$) 340 (M$^+$+H).

EXAMPLE 32

3-[2-(4-Fluorophenyl)pyridin-5-yl)]-7-trifluoromethylimidazo[1,2-α]pyrimidine

To a degassed mixture of 2,5-dibromopyridine (500 mg, 2.11 mmol) and 4-fluorobenzeneboronic acid (444 mg, 3.17 mmol) in ethylene glycol dimethyl ether (4.2 ml) and 2M aqueous sodium carbonate (2.1 ml) was added tetrakis(triphenylphosphine)palladium(0) (98 mg, 0.08 mmol). This mixture was heated at reflux for 14 h. After cooling the crude reaction was partitioned between water and dichloromethane. The organics were dried over anhydrous magnesium sulfate, filtered and adsorbed onto silica. Purification by chromatography on silica gel, eluting with a mixture of 4% diethyl ether in isohexane, gave 5-bromo-2-(4-fluorophenyl)pyridine (470 mg) as a white solid: $\delta_H$ (360 MHz, CDCl$_3$) 7.30 (1H, d, J 7), 7.12–7.19 (2H, m), 7.57 (1H, d, J 8), 7.86 (1H, dd, J 2 and 8), 7.92–7.98 (2H, m), 8.72 (1H, d, J 2), m/z (ES$^+$) 251, 252, 253, 254 (M$^+$+H).

3-Tributylstannyl-7-trifluoromethylimidazo[1,2-α]pyrimidine was reacted with 5-bromo-2-(4-fluorophenyl)pyridine by the method of Example 1 to furnish 3-[2-(4-fluorophenyl)pyridin-5-yl]-7-trifluoromethylimidazo[1,2-α]pyrimidine (47mg) as a yellow solid: $\delta_H$ (400 MHz, CDCl$_3$) 7.19–7.25 (2H, m), 7.31 (1H, d, J 7), 7.90–7.97 (2H, m), 8.06–8.11 (2H, m), 8.19 (1H, s), 8.82 (1H, d, J 7), 8.91 (1H, dd, J 2 and 1); m/z (ES$^+$) 358, 359 (M$^+$+H).

EXAMPLE 33

3-[2-(1H-Pyrrol-1-yl)pyridin-5-yl]-7-trifluoromethylimidazo[1,2-α]pyrimidine

3-Tributylstannyl-7-trifluoromethylimidazo[1,2-α]pyrimidine was reacted with 5-bromo-2-(pyrrol-1-yl)pyridine by the method of Example 1 to afford 3-[2-(1H-pyrrol-1-yl)pyridin-5-yl]-7-trifluoromethylimidazo[1,2-α]pyrimidine as a yellow solid: $\delta_H$ (400 MHz, CDCl$_3$) 6.42 (2H, m), 7.28 (1H, d, J 8), 7.52 (1H, dd, J 8 and 1), 7.58 (2H,

EXAMPLE 34

3-(2-Chloropyrimidin-4-yl)-7-(1-hydroxy-1-methylethyl)imidazo[1,2-α]pyrimidine 7-(1-Methyl-1-triethylsilanyloxyethyl)-3-tributylstannyl-imidazo[1,2-α]pyrimidine was reacted with 2,4-dichloropyrimidine by the method of Example 5 to afford 3-(2-chloropyrimidin-4-yl)-7-(1-methyl-1-triethylsilanyloxyethyl)imidazo[1,2-α]pyrimidine as a white solid: $\delta_H$ (400 MHz, CDCl$_3$) 0.70 (6H, q, J 8.0), 1.00 (9H, t, J 8.0), 1.69 (6H, s), 7.57 (1H, d, J 5.5), 7.67 (1H, d, J 7.0), 8.53 (2H, m), 10.07 (1H, d, J 7.0); m/z (ES$^+$) 403 (M$^+$+H).

The foregoing compound was deprotected using the procedure of Example 21 to afford 3-(2-chloropyrimidin-4-yl)-7-(1-hydroxy-1-methylethyl)imidazo[1,2-α]pyrimidine as a white solid: $\delta_H$ (400 MHz, CDCl$_3$) 1.65 (6H, s), 4.12 (1H, s), 7.36 (1H, d, J 7.4), 7.61 (1H, d, J 5.1), 8.58 (2H, dd, J 6.7, 5.5), 10.15 (1H, d, J 7.4); m/z (ES$^+$) 290 (M$^+$+H).

EXAMPLE 35

5-Fluoro-2-{4-[7-(1-hydroxy-1-methylethyl)imidazo[1,2-α]pyrimidin-3-yl]-pyrimidin-2-yl}benzonitrile To a degassed solution of 3-(2-chloropyrimidin-4-yl)-7-(1-methyl-1-triethylsilanyloxyethyl)imidazo[1,2-α]pyrimidine (300 mg, 1.0 mmol) and 5-fluoro-2-(4,4,5,5-tetramethyl-[1,3,2]dioxaborolan-2-yl)benzonitrile (371 mg, 1.5 mmol) (synthesised as in Example 22) in THF was added degassed sodium carbonate solution (2 ml) followed by tetrakis(triphenylphosphine)palladium(0) (58 mg, 0.05 mmol) and the mixture heated at reflux for 2.5 hours. The reaction was diluted with dichloromethane (DCM) (20 ml) and washed with water (10 ml) and brine (10 ml). The organic phase was dried (Mg$_2$SO$_4$), filtered and evaporated to give an orange oil. The crude product was chromatographed on silica eluting on a gradient of 1–5% MeOH in DCM. Appropriate fractions were pooled and evaporated to give an off-white solid (163 mg). The solid was recrystallised from DCM/EtOAc to give 5-fluoro-2-{4-[7-(1-methyl-1-triethylsilanyloxyethyl)imidazo[1,2-α]pyrimidin-3-yl]-pyrimidin-2-yl}benzonitrile as a cream-coloured solid (148 mg): $\delta_H$ (400 MHz, CDCl$_3$) 0.69 (6H, q, J 7.8), 0.99 (9H, t, J 7.8), 1.70 (6H, s), 7.49–7.52 (1H, m), 7.61 (1H, d, J 8.2), 7.62 (1H, d, J 7.0), 7.68 (1H, d, J 5.5), 8.34 (1H, dd, J 5.5, 8.6), 8.53 (1H, s), 8.84 (1H, d, J 5.5), 10.28 (1H, d, J 7.4); m/z (ES$^+$) 489 (M$^+$+H).

The foregoing compound was deprotected using the procedure of Example 21 to afford 5-fluoro-2-{4-[7-(1-hydroxy-1-methylethyl)imidazo[1,2-α]pyrimidin-3-yl]pyrimidin-2-yl}benzonitrile as a white solid: $\delta_H$ (400 MHz, CDCl$_3$) 1.65 (6H, s), 4.27 (1H, s), 7.32 (1H, d, J 7.4), 7.40–7.61 (2H, m), 7.71 (1H, d, J 5.5), 8.35 (1H, dd, J 5.5, 9.0), 8.55 (1H, s), 8.87 (1H, d, J 5.5), 10.40 (1H, d, J 7.4); m/z (ES$^+$) 375 (M$^+$+H).

EXAMPLE 36

2-[3-(2-(Pyridin-3-yl)pyrimidin-4-yl)imidazo[1,2-α]pyrimidin-7-yl]propan-2-ol 3-(2-Chloropyrimidin-4-yl)-7-(1-methyl-1-triethylsilanyloxyethyl)imidazo[1,2-α]pyrimidine was reacted with diethyl(3-pyridyl)borane by the method of Example 35 to afford 7-(1-methyl-1-triethylsilanyloxyethyl)-3-[2-(pyridin-3-yl)pyrimidin-4-yl]imidazo[1,2-α]pyrimidine as a white solid: $\delta_H$ (400 MHz, CDCl$_3$) 0.73 (6H, q, J 8.1), 1.01 (9H, t, J 8.0), 1.72 (6H, s), 7.46–7.53 (2H, m), 7.61 (1H, d, J 5.5), 7.67 (1H, d, J 7.0), 8.52 (1H, s), 8.72–8.79 (2H, m), 9.71 (1H, m), 10.24 (1H, d, J 7.0); m/z (ES$^+$) 447 (M$^+$+H).

The foregoing compound was deprotected using the procedure of Example 21 to afford 2-[3-(2-(pyridin-3-yl)pyrimidin-4-yl)imidazo[1,2-α]pyrimidin-7-yl]propan-2-ol as a white solid: $\delta_H$ (400 MHz, d$^6$-DMSO) 1.55 (6H, s), 5.61 (1H, s), 7.60–7.64 (1H, m), 7.76 (1H, d, J 7.4), 8.06 (1H, d, J 5.5), 8.75–8.78 (1H, m), 8.78 (1H, s), 8.86 (1H, s), 8.92 (1H, d, J 5.5), 9.60 (1H, m), 10.21 (1H, d, J 7.4); m/z (ES$^+$) 333 (M$^+$+H).

EXAMPLE 37

2-{4-[7-(1-Hydroxy-1-methylethyl)imidazo[1,2-α]pyrimidin-3-yl]pyrimidin-2-yl}thiophene-3-carbonitrile 3-(2-Chloropyrimidin-4-yl)-7-(1-methyl-1-triethylsilanyloxyethyl)imidazo[1,2-α]pyrimidine was reacted with 2-(4,4,5,5-tetramethyl-[1,3,2]dioxaborolan-2-yl)thiophene-3-carbonitrile (synthesised from 2-bromothiophene-3-carbonitrile following the procedure in Example 21) by the method of Example 35 to afford 2-{4-[7-(1-methyl-1-triethylsilanyloxyethyl)imidazo[1,2-α]pyrimidin-3-yl]pyrimidin-2-yl}thiophene-3-carbonitrile as a white solid: $\delta_H$ (400 MHz, CDCl$_3$) 0.67 (6H, q, J 8.1), 0.99 (9H, t, J 8.0), 1.71 (6H, s), 7.66 (2H, m), 7.97 (1H, d, J 5.5), 8.51 (1H, s), 8.79 (1H, d, J 5.5), 9.71 (1H, m), 10.34 (1H, d, J 7.0); m/z (ES$^+$) 477 (M$^+$+H).

The foregoing compound was deprotected using the procedure of Example 21 to afford 2-{4-[7-(1-hydroxy-1-methylethyl)imidazo[1,2-α]pyrimidin-3-yl]pyrimidin-2-yl}thiophene-3-carbonitrile as a white solid: $\delta_H$ (400 MHz, d$^6$-DMSO) 1.56 (6H, s), 7.85 (1H, d, J 7.4), 8.09 (1H, d, J 5.5), 8.17 (1H, d, J 5.5), 8.21 (1H, d, J 5.5), 9.04 (1H, d, J 5.5), 9.15 (1H, s), 10.35 (1H, d, J 7.0); m/z (ES$^+$) 363 (M$^+$+H).

EXAMPLE 38

5-Fluoro-2-{4-[7-trifluoromethylimidazo[1,2-α]pyrimidin-3-yl]pyrimidin-2-yl}benzonitrile 3-(2-Chloropyrimidin-4-yl)-7-trifluoromethylimidazo[1,2-α]pyrimidine was coupled to 5-fluoro-2-(4,4,5,5-tetramethyl-[1,3,2]dioxaborolan-2-yl)benzonitrile (synthesised as in Example 22) by the method of Example 1 to afford 5-fluoro-2-{4-[7-trifluoromethylimidazo[1,2-α]pyrimidin-3-yl]pyrimidin-2-yl}benzonitrile as a white solid: $\delta_H$ (400 MHz, CDCl$_3$) 7.48–7.53 (2H, m), 7.63 (1H, dd, J 2.5, 8.0), 7.78 (1H, d, J 5.5), 8.39 (1H, dd, J 5.5, 9.0), 8.74 (1H, s), 8.95 (1H, d, J 5.5), 10.67 (1H, d, J 6.7); m/z (ES$^+$) 385 (M$^+$+H).

EXAMPLE 39

2-[3-(2-Trifluoromethylpyrimidin-4-yl)imidazo[1,2-α]pyrimidin-7-yl]propan-2-ol

A solution of isopropylmagnesium chloride (2.0M in THF, 525 μl, 1.05 mmol) was added dropwise to a stirred suspension of 3-bromo-7-(1-methyl-1-triethylsilanyloxyethyl)imidazo[1,2-α]pyrimidine (370 mg, 1.0 mmol) in THF (5 ml) at −78° C. under N$_2$. The resulting solution was stirred at −78° C. for 15 min and then tributyltin chloride (298 μl, 1.1 mmol) was added. The reaction was warmed to 0° C. and stirred for 1 h. 4-Chloro-2-trifluoromethylpyrimidine (200 mg, 1.1 mmol) and tetrakis(triphenylphosphine)palladium(0) (110 mg, 10 mol %) were added and the reaction heated at reflux for 18 h. The mixture was concentrated under reduced pressure while dry loading onto silica and then purified by column chromatography on silica using 50–80% EtOAc/isohexanes as the eluent to afford 7-(1-methyl-1-triethylsilanyloxyethyl)-3-(2-trifluoromethylpyrimidin-4-yl)imidazo[1,2-α]pyrimidine (136 mg): $^1$H NMR (400 MHz, CDCl$_3$) δ 10.10 (1H, d, J 7.4), 8.82 (1H, d, J 5.5), 8.57 (1H, s), 7.78 (1H, d, J 5.5), 7.67 (1H, d, J 7.4), 1.70 (6H, s), 1.00 (9H, t, J 8.0), 0.68 (6H, q, J 8.0); m/z (ES$^+$) 438 (M+H$^+$).

7-(1-Methyl-1-triethylsilanyloxyethyl)-3-(2-trifluoromethylpyrimidin-4-yl)imidazo[1,2-α]pyrimidine (136 mg, 0.31 mmol) in EtOH (5 ml) was treated with conc. HCl (5 drops) and the mixture stirred at room temperature for 16 h. The resulting mixture was concentrated under reduced pressure and then NaHCO$_3$ solution (20 ml) added. The organics were extracted with CH$_2$Cl$_2$ (3×20 ml) and concentrated under reduced pressure while dry loading onto MgSO$_4$. The residue was purified by column chromatography on silica using 5% MeOH/CH$_2$Cl$_2$ as the eluent to afford 2-[3-(2-trifluoromethylpyrimidin-4-yl)imidazo[1,2-α]pyrimidin-7-yl]propan-2-ol (60 mg, 60%): $^1$H NMR (400 MHz, d$^6$-DMSO) δ 9.97 (1H, d, J 7.4), 9.00 (1H, d, J 5.6), 8.97 (1H, s), 8.35 (1H, d, J 5.6), 7.73 (1H, d, J 7.4), 1.53 (6H, s); m/z (ES$^+$) 324 (M+H$^+$).

EXAMPLE 40

2-[3-(2-(Thiazol-2-yl)pyrimidin-4-yl)imidazo[1,2-α]pyrimidin-7-yl]propan-2-ol

A solution of 3-(2-chloropyrimidin-4-yl)-7-(1-methyl-1-triethylsilanyloxyethyl)imidazo[1,2-α]pyrimidine (prepared as in Example 34) (200 mg, 0.50 mmol) and 2-tributylstannylthiazole (370 mg, 1.0 mmol) in THF (10 ml) was degassed with a stream of N$_2$ for 10 min, then tetrakis(triphenylphosphine)palladium(0) (29 mg, 5 mol %) was added and the reaction heated at reflux for 5 h. The mixture was concentrated under reduced pressure while dry loading onto silica and then purified by column chromatography on silica using 100% EtOAc as the eluent to afford 7-(1-methyl-1-triethylsilanyloxyethyl)-3-[2-(thiazol-2-yl)pyrimidin-4-yl]imidazo[1,2-α]pyrimidine (128 mg, 57%); m/z (ES$^+$) 453 (M+H$^+$).

The foregoing compound (128 mg, 0.28 mmol) was deprotected as described in Example 39 to yield, after column chromatography on silica using 5% MeOH(CH$_2$Cl$_2$, 2-[3-(2-(thiazol-2-yl)pyrimidin-4yl)imidazo[1,2-α]pyrimidin-7-yl]propan-2-ol (54 mg, 56%): $^1$H NMR (400 MHz, d$^6$-DMSO) δ 10.37 (1H, d, J 7.2), 8.90–8.83 (2H, m), 8.17 (1H, d, J 3.1), 8.11 (1H, d, J 5.6), 8.05 (1H, d, J 3.1), 7.71 (1H, d, J 7.2), 5.61 (1H, s), 1.55 (6H, s); m/z (ES$^+$) 339 (M+H$^+$).

EXAMPLE 41

2-[3-(2-(Imidazol-1-yl)pyrimidin-4-yl)imidazo[1,2-α]pyrimidin-7-yl]propan-2-ol

A solution of LiHMDS (370 μl) in hexanes (1.0M, 370 μmol) was added to a stirred solution of imidazole (25 mg, 0.37 mmol) and 3-(2-chloropyrimidin-4-yl)-7-(1-methyl-1-triethylsilanyloxyethyl)imidazo[1,2-α]pyrimidine (from Example 34) (150 mg, 0.37 mmol) in THF (5 ml) at −78° C. under N$_2$. The reaction was allowed to warm slowly to room temperature overnight and was then quenched with NH$_4$Cl solution (10 ml). The organics were extracted with EtOAc (2×25 ml), washed with brine (10 ml) and concentrated under reduced pressure while dry loading onto silica. The residue was purified by column chromatography on silica using 100% EtOAc as the eluent to afford 3-[2-(imidazol-1-yl)pyrimidin-4-yl]-7-(1-methyl-1-triethylsilanyloxyethyl)imidazo[1,2-α]pyrimidine (73 mg, 45%): $^1$H NMR (400 MHz, d$^6$-DMSO) δ 10.08 (1H, d, J 7.2), 8.93 (1H, s), 8.85–8.78 (2H, m), 8.13 (1H, d, J 1.1), 8.03 (1H, d, J 5.5), 7.72 (1H, d, J 7.2), 7.21 (1H, s), 1.64 (6H, s), 0.96 (9H, t, J 8.0), 0.65 (6H, q, J 8.0); m/z (ES$^+$) 453 (M+H$^+$).

The foregoing compound (73 mg, 0.17 mmol) in EtOH (4 ml) was treated with conc. HCl (4 drops) and the mixture stirred at room temperature for 7 h. The resulting mixture was concentrated under reduced pressure and then triturated with CH$_2$Cl$_2$ (15 ml) and filtered. NaHCO$_3$ solution (20 ml) was added to the solid and the organics were extracted with CH$_2$Cl$_2$ (30 ml) and EtOAc (2×30 ml), then dried (MgSO$_4$) and concentrated under reduced pressure to afford 2-[3-(2-(imidazol-1-yl)pyrimidin-4-yl)imidazo[1,2-α]pyrimidin-7-yl]propan-2-ol (25 mg, 46%): $^1$H NMR (400 MHz, d$^6$-DMSO) δ 10.06 (1H, d, J 7.2), 8.92 (1H, s), 8.83–8.78 (2H, m), 8.12 (1H, s), 8.03 (1H, d, J 5.0), 7.77 (1H, d, J 7.2), 7.21 (1H, s), 5.63 (1H, s), 1.54 (6H, s); m/z (ES$^+$) 322 (M+H$^+$).

EXAMPLE 42

2-[3-(2-(Pyridin-4-yl)pyrimidin-4-yl)imidazo[1,2-α]pyrimidin-7-yl]propan-2-ol 3-(2-Chloropyrimidin-4-yl)-7-(1-methyl-1-triethylsilanyloxyethyl)-imidazo[1,2-α]pyrimidine (from Example 34) (403 mg, 1.0 mmol), 4-tributylstannylpyridine (736 mg, 2.0 mmol), tetrakis(triphenylphosphine)palladium (0) (115 mg, 10 mol %) and copper(I) iodide (115 mg) in 1,4-dioxane (20 ml) were heated at reflux overnight. Purification by column chromatography on silica using 3–6% MeOH/CH$_2$Cl$_2$ as the eluent afforded 7-(1-methyl-1-triethylsilanyloxyethyl)-3-[2-(pyridin-4-yl)pyrimidin-4-yl]imidazo[1,2-α]pyrimidine: $^1$H NMR (400 MHz, d$^6$-DMSO) δ 10.23 (1H, d, J 7.3), 8.98 (1H, d, J 5.4), 8.89 (1H, s), 8.85–8.80 (2H, m), 8.36 (2H, d, J 5.9), 8.14 (1H, d, J 5.5), 7.70 (1H, d, J 7.3), 1.65 (6H, s), 0.95 (9H, t, J 7.8), 0.66 (6H, q, J 7.8).

7-(1-Methyl-1-triethylsilanyloxyethyl)-3-[2-(pyridin-4-yl)pyrimidin-4-yl]imidazo[1,2-α]pyrimidine from above was treated with conc. HCl (10 drops) as described in Example 39 to yield after purification by column chromatography on silica, using 6% MeOH/CH$_2$Cl$_2$ as the eluent, 2-[3-(2-(pyridin-4-yl)pyrimidin-4-yl)imidazo[1,2-α]pyrimidin-7-yl]propan-2-ol (51 mg, 15%): $^1$H NMR (360 MHz, d$^6$-DMSO) δ 10.23 (1H, d, J 7.2), 8.98 (1H, d, J 5.5), 8.88 (1H, s), 8.85–8.80 (2H, m), 8.36 (2H, dd, J 4.5, 1.6), 8.14 (1H, d, J 5.5), 7.77 (1H, d, J 7.2), 5.62 (1H, s), 1.55 (6H, s); m/z (ES$^+$) 333 (M+H$^+$).

EXAMPLE 43

2-[3-(2-(Furan-2-yl)pyrimidin-4-yl)imidazo[1,2-α]pyrimidin-7-yl]propan-2-ol 3-(2-Chloropyrimidin-4-yl)-7-(1-methyl-1-triethylsilanyloxyethyl)-imidazo[1,2-α]pyrimidine (from Example 34) (58 mg, 0.14 mmol) and 2-tributylstannylfuran (102 mg, 0.29 mmol) were heated at reflux overnight as described in Example 40. Purification by column chromatography on silica using 70% EtOAc/isohexanes as the eluent gave 3-[2-(furan-2-yl)pyrimidin-4-yl]-7-(1-methyl-1-triethylsilanyloxyethyl)imidazo[1,2-α]pyrimidine (36 mg, 57%): m/z (ES$^+$) 435 (M+H$^+$).

The foregoing compound (36 mg, 0.08 mmol) was deprotected as described in Example 39 to yield, after column chromatography on silica using 5% MeOH/CH$_2$Cl$_2$, 2-[3-(2-(furan-2-yl)pyrimidin-4-yl)imidazo[1,2-α]pyrimidin-7-yl]propan-2-ol (12 mg, 45%): $^1$H NMR (360 MHz, d$^6$-DMSO) δ 10.29 (1H, d, J 7.2), 8.85–8.75 (2H, m), 7.99 (1H, broad s), 7.91 (1H, d, J 5.5), 7.72 (1H, d, J 7.2), 7.53 (1H, dd, J 3.5, 0.6), 6.77 (1H, dd, J 3.5, 1.7), 5.60 (1H, s), 1.54 (6H, s); m/z (ES$^+$) 322 (M+H$^+$).

EXAMPLE 44

2-[3-(2-(Furan-3-yl)pyrimidin-4-yl)imidazo[1,2-α]pyrimidin-7-yl]propan-2-ol

A mixture of 3-(2-chloropyrimidin-4-yl)-7-(1-methyl-1-triethylsilanyloxyethyl)imidazo[1,2-α]pyrimidine (from Example 34) (200 mg, 0.49 mmol), 3-furanboronic acid (111 mg, 0.98 mmol), K$_3$PO$_4$ (457 mg, 1.96 mmol) and tetrakis(triphenylphosphine)palladium(0) (50 mg, 9 mol %) in DMA (6 ml) was heated at 90° C. for 45 min under N$_2$. The reaction was concentrated under reduced pressure while azeotroping with xylene (3×30 ml). EtOAc (50 ml) and H$_2$O (50 ml) were added and the organics separated and concentrated under reduced pressure while loading onto MgSO$_4$. Purification by column chromatography on silica using 3% MeOH/CH$_2$Cl$_2$ as the eluent gave 3-[2-(furan-3-yl)pyrimidin-4-yl]-7-(1-methyl-1-triethylsilanyloxyethyl)imidazo[1,2-α]pyrimidine (203 mg, 94%): m/z (ES$^+$) 435 (M+H$^+$).

3-[2-(Furan-3-yl)pyrimidin-4-yl]-7-(1-methyl-1-triethylsilanyloxyethyl)imidazo[1,2-α]pyrimidine (203 mg, 0.47 mmol) in EtOH (10 ml) was treated with conc. HCl (15 drops) and the resulting solution was stirred at room temperature for 12 h during which time a precipitate formed. The solid was filtered off and was then partitioned between CH$_2$Cl$_2$ (20 ml) and NaHCO$_3$ solution (20 ml). The organic layer was separated and the aqueous extracted with CH$_2$Cl$_2$ (3×20 ml). The combined organic extracts were dried (MgSO$_4$) and concentrated under reduced pressure to afford 2-[3-(2-(furan-3-yl)pyrimidin-4-yl)imidazo[1,2-α]pyrimidin-7-yl]propan-2-ol (64 mg, 42%): $^1$H NMR (400 MHz, d$^6$-DMSO) δ 10.29 (1H, d, J 7.3), 8.81 (1H, s), 8.77 (1H, d, J 5.4), 8.68 (1H, s), 7.89 (1H, d, J 5.4), 7.87 (1H, s), 7.74 (1H, d, J 7.3), 7.20 (1H, s), 5.61 (1H, s), 1.54 (6H, s); m/z (ES$^+$) 322 (M+H$^+$).

EXAMPLE 45

2-{3-[2-(1-Oxypyridin-4-yl)pyrimidin-4-yl]imidazo[1,2-α]pyrimidin-7-yl}propan-2-ol m-CPBA (50%, 154 mg, 0.45 mmol) was added to a stirred solution of 7-(1-methyl-1-triethylsilanyloxyethyl)-3-[2-(pyridin-4-yl)pyrimidin-4-yl]imidazo[1,2-α]pyrimidine (200 mg, 0.45 mol) in CH$_2$Cl$_2$ (8 ml) and MeOH (2 ml). The reaction was stirred at room temperature for 12 h, then was diluted with CH$_2$Cl$_2$ (200 ml), washed with 1N NaOH (150 ml) and concentrated under reduced pressure while dry loading onto MgSO$_4$. Purification by column chromatography on silica using first 5% EtOH/EtOAc to remove unreacted starting material and then 5% MeOH/CH$_2$Cl$_2$ gave 7-(1-methyl-1-triethylsilanyloxyethyl)-3-[2-(1-oxypyridin-4-yl)pyrimidin-4-yl]imidazo[1,2-α]pyrimidine (111 mg, 54%): $^1$H NMR (400 MHz, CDCl$_3$) δ 10.06 (1H, d, J 7.2), 8.78 (1H, d, J 5.5), 8.52 (1H, s), 8.39–8.31 (4H, m), 7.68 (2H, d, J 7.3), 7.60 (1H, d, J 5.5), 1.72 (6H, s), 1.01 (9H, t, J 7.9), 0.69 (6H, q, J 7.9); m/z (ES$^+$) 463 (M+H$^+$).

7-(1-Methyl-1-triethylsilanyloxyethyl)-3-[2-(1-oxypyridin-4-yl)pyrimidin-4-yl]imidazo[1,2-α]pyrimidine (140 mg, 0.30 mmol) was treated with conc. HCl (15 drops) as described in Example 39 to yield, after purification by column-chromatography on silica, using 10% MeOH/CH$_2$Cl$_2$ as the eluent, 2-{3-[2-(1-oxypyridin-4-yl)pyrimidin-4-yl]imidazo[1,2-α]pyrimidin-7-yl}propan-2-ol (45 mg, 43%): $^1$H NMR (360 MHz, d$^6$-DMSO) δ 10.18 (1H, d, J 7.2), 8.93 (1H, d, J 5.5), 8.88 (1H, s), 8.45–8.33 (2H, m), 8.06 (1H, d, J 5.5), 7.73 (1H, d, J 7.2), 5.63 (1H, s), 1.55 (6H, s); m/z (ES$^+$) 349 (M+H$^+$).

EXAMPLE 46

3-[6-(1H-Imidazol-1-yl)pyridin-2-yl]-7-trifluoromethylimidazo[1,2-α]pyrimidine

A stirred solution of 2,6-dibromopyridine (2.0 g, 8.3 mmol) and imidazole sodium salt (1.0 g, 10.5 mmol) in dimethylsulfoxide (10 ml) was heated at 100° C. for 36 h. After cooling to ambient temperature the reaction was diluted with water and extracted into dichloromethane. Combined organic extracts were washed with water and saturated brine then dried over magnesium sulfate, filtered and evaporated in vacuo to give a solid. Purification by chromatography on silica gel eluting with dichloromethane, then dichloromethane containing 5% methanol, gave 2-bromo-6-(1H-imidazol-1-yl)pyridine (0.18 g) as an off-white solid: δ$_H$ (400 MHz, CDCl$_3$) 7.20 (1H, m), 7.32 (1H, d, J 8), 7.47 (1H, d, J 8), 7.62 (1H, m), 7.68 (1H, dd, J 8 and 8), 8.35 (1H, s); m/z (ES$^+$) 224/226 (M$^+$+H).

2-Bromo-6-(1H-imidazol-1-yl)pyridine (0.18 g, 0.8 mmol) was coupled to 3-tributylstannyl-7-trifluoromethylimidazo[1,2-α]pyrimidine (0.9 mmol) by the method of Example 1. Purification by chromatography on silica gel eluting with dichloromethane on a gradient of methanol (0–10%) and trituration with ethyl acetate gave 3-[6-(1H-imidazol-1-yl)pyridin-2-yl]-7-trifluoromethylimidazo[1,2-α]pyrimidine (42 mg) as an off-white solid: δ$_H$ (400 MHz, CDCl$_3$) 7.30 (1H, s), 7.35 (1H, d, J 8), 7.43 (1H, d, J 7), 7.65 (1H, s), 7.79 (1H, d, J 8), 8.00 (1H, dd, J 8 and 8), 8.38 (1H, s), 8.59 (1H, s), 10.24 (1H, d, J 7); m/z (ES$^+$) 331 (M$^+$+H).

EXAMPLE 47

3-[6-(Morpholin-4-yl)pyridin-2-yl]-7-trifluoromethylimidazo[1,2-α]pyrimidine

A stirred solution of 2,6-dibromopyridine (5.0 g, 20.7 mmol), triethylamine (3.0 ml, 21.7 mmol) and morpholine (1.8 g, 20.7 mmol) in dimethylsulfoxide (25 ml) was heated at 85° C. for 4 h. After cooling to ambient temperature the reaction was poured into water. After decanting off the aqueous, the gum was dissolved in dichloromethane, washed with water and saturated brine, then dried over magnesium sulfate, filtered and evaporated in vacuo to give a solid. Purification by chromatography on silica gel eluting with dichloromethane gave 4-(6-bromopyridin-2-yl)morpholine (3.0 g) as a white solid: δ$_H$ (400 MHz, CDCl$_3$) 3.50 (4H, t, J 5), 3.80 (4H, t, J 5), 6.50 (1H, d, J 8), 6.79 (1H, d, J 8), 7.31 (1H, dd, J 8 and 8); m/z (ES$^+$) 242/244 (M$^+$+H).

4-(6-Bromopyridin-2-yl)morpholine (0.46 g, 1.9 mmol) was coupled to 3-tributylstannyl-7-trifluoromethylimidazo

[1,2-α]pyrimidine (1.8 mmol) by the method of Example 1. Purification by chromatography on silica gel eluting with dichloromethane on a gradient of methanol (0–10%) and crystallisation from ethyl acetate-isohexane gave 3-[6-(morpholin-4-yl)pyridin-2-yl]-7-trifluoromethylimidazo[1,2-α]pyrimidine (220 mg) as a yellow solid: $\delta_H$ (400 MHz, CDCl$_3$) 3.57 (4H, t, J 5), 3.90 (4H, t, J 5), 6.65 (1H, d, J 8), 7.20 (1H, d, J 8), 7.33 (1H, d, J 7), 7.65 (1H, dd, J 8 and 8), 8.42 (1H, s), 10.19 (1H, d, J 7); m/z (ES$^+$) 350 (M$^+$+H).

EXAMPLE 48

3-(6-Phenylpyridin-2-yl)-7-trifluoromethylimidazo [1,2-α]pyrimidine

A degassed solution of 2,6-dibromopyridine (4.0 g, 16.5 mmol) and phenylboronic acid (2.1 g, 16.7 mmol) in dry tetrahydrofuran (30 ml) was stirred under an atmosphere of nitrogen then sodium carbonate (3.55 g, 33.5 mmol) and tetrakis(triphenylphosphine)palladium(0) (0.95 g, 5 mol %) added. This mixture was heated to reflux for 18 h. After cooling to ambient temperature, solvent was removed in vacuo, the residue dissolved in dichloromethane, washed with water and saturated brine, then dried over magnesium sulfate, filtered and evaporated in vacuo to give a solid. Purification by chromatography on silica gel eluting with dichloromethane gave 2-bromo-6-phenylpyridine (0.17 g) as a white solid: $\delta_H$ (400 MHz, CDCl$_3$) 7.45 (4H, m), 7.60 (1H, dd, J 8 and 8), 7.70 (1H, d, J 8), 7.99 (2H, d, J 8); m/z (ES$^+$) 233/235 (M$^+$+H).

2-Bromo-6-phenylpyridine (0.17 g, 0.7 mmol) was coupled to 3-tributylstannyl-7-trifluoromethylimidazo[1,2-α]pyrimidine (0.9 mmol) by the method of Example 1. Purification by chromatography on silica gel eluting with dichloromethane on a gradient of methanol (0–10%) and trituration with ethyl acetate gave 3-(6-phenylpyridin-2-yl)-7-trifluoromethylimidazo[1,2-α]pyrimidine (82 mg) as a pale yellow solid: $\delta_H$ (400 MHz, CDCl$_3$) 7.39 (1H, d, J 7), 7.53 (3H, m), 7.70 (1H, d, J 8), 7.78 (1H, d, J 8), 7.91 (1H, dd, J 8 and 8), 8.01 (2H, d, J 8), 8.53 (1H, s), 10.62 (1H, d, J 7); m/z (ES$^+$) 341 (M$^+$+H).

EXAMPLE 49

6-(7-Trifluoromethylimidazo[1,2-α]pyrimidin-3-yl)-2,3'-bipyridine

3-Tributylstannylpyridine (3.3 g, 9.0 mmol) was added to a degassed solution of 2,6-dibromopyridine (2.0 g, 8.3 mmol) and tetrakis(triphenylphosphine)palladium(0) (0.48 g, 5 mol %) in dry tetrahydrofuran (30 ml), stirred under an atmosphere of nitrogen and heated to reflux for 48 h. After cooling to ambient temperature, solvent was removed in vacuo, the residue dissolved in dichloromethane and purified by chromatography on silica gel eluting with dichloromethane on a gradient of methanol (0–4%). Trituration with isohexane gave 6-bromo-2,3'-bipyridine (0.4 g) as a solid: $\delta_H$ (400 MHz, CDCl$_3$) 7.42 (1H, dd, J 8 and 8), 7.49 (1H, d, J 7), 7.65 (1H, dd, J 7 and 7), 7.73 (1H, d, J 7), 8.35 (1H, m), 8.68 (1H, m), 9.16 (1H, s); m/z (ES$^+$) 235/236 (M$^+$+H).

6-Bromo-2,3'-bipyridine (0.37 g, 1.6 mmol) was coupled to 3-tributylstannyl-7-trifluoromethylimidazo[1,2-α] pyrimidine (1.6 mmol) by the method of Example 1. Purification by chromatography on silica gel eluting with dichloromethane on a gradient of methanol (0–5%) and trituration with isohexane gave 6-(7-trifluoromethylimidazo[1,2-α] pyrimidin-3-yl)-2,3'-bipyridine (130 mg) as a pale yellow solid: $\delta_H$ (400 MHz, CDCl$_3$) 7.40 (1H, d, J 7), 7.50 (1H, dd, J 8 and 8), 7.72 (1H, d, J 8), 7.85 (1H, d, J 8), 7.97 (1H, dd, J 8 and 8), 8.30 (1H, m), 8.59 (1H, s), 8.75 (1H, m), 9.29 (1H, s), 10.51 (1H, d, J 7); m/z (ES$^+$) 341 (M$^+$+H).

EXAMPLE 50

N-[6-(7-Trifluoromethylimidazo[1,2-α]pyrimidin-3-yl)pyridin-2-yl]acetamide

Acetyl chloride (0.90 ml, 12.6 mmol) was added dropwise to a stirred solution of 2-amino-6-bromopyridine (2.0 g, 11.3 mmol) and triethylamine (3.2 ml, 23.1 mmol) in dry dichloromethane (15 ml) under an atmosphere of nitrogen at 0° C. After allowing to return to ambient temperature, solvent was removed in vacuo and the residue purified by chromatography on silica gel eluting with 40% ethyl acetate in isohexane. This gave N-(6-bromopyridin-2-yl)acetamide (0.45 g) as a white solid: $\delta_H$ (400 MHz, CDCl$_3$) 2.19 (3H, s), 7.20 (1H, d, J 8), 7.55 (1H, dd, J 9 and 9), 7.90 (1H, s), 8.14 (1H, d, J 9).

N-(6-Bromopyridin-2-yl)acetamide (0.33 g, 1.56 mmol) was coupled to 3-tributylstannyl-7-trifluoromethylimidazo [1,2-α]pyrimidine (1.6 mmol) by the method of Example 1. Purification by chromatography on silica gel eluting with ethyl acetate on a gradient of methanol (0–5%) gave N-[6-(7-trifluoromethylimidazo[1,2-α]pyrimidin-3-yl)pyridin-2-yl]acetamide (14 mg) as an off-white solid: $\delta_H$ (400 MHz, DMSO) 2.19 (3H, s), 7.60 (1H, d, J 7), 7.85 (1H, d, J 7), 7.92 (1H, dd, J 8 and 8), 7.97 (1H, d, J 8), 8.90 (1H, s), 10.65 (1H, s), 10.75 (1H, d, J 7); m/z (ES$^+$) 321 (M$^+$+H).

EXAMPLE 51

N-(tert-Butyl)-6-(7-trifluoromethylimidazo[1,2-α] pyrimidin-3-yl)pyridin-2-ylamine A stirred solution of 2,6-dibromopyridine (4.0 g, 16.5 mmol) and tert-butylamine (1.8 ml, 17.2 mmol) in dimethylsulfoxide (10 ml) was heated at 100° C. in a sealed tube for 20 h. After cooling to ambient temperature the reaction was diluted with water and extracted into dichloromethane. Combined organic extracts were washed with water and saturated brine then dried over magnesium sulfate, filtered and evaporated in vacuo to give a solid. Purification by chromatography on silica gel eluting with 20% diethyl ether in isohexane gave 6-bromo-N-(tert-butyl)pyridin-2-ylamine (0.4 g) as a solid: $\delta_H$ (360 MHz, CDCl$_3$) 1.40 (9H, s), 6.34 (1H, d, J 8), 6.66 (1H, d, J 8), 7.18 (1H, dd, J 8 and 8); m/z (ES$^+$) 229/231 (M$^+$+H).

6-Bromo-N-(tert-butyl)pyridin-2-ylamine (0.36 g, 1.56 mmol) was coupled to 3-tributylstannyl-7-trifluoromethylimidazo[1,2-α]pyrimidine (1.6 mmol) by the method of Example 1. Purification by chromatography on silica gel eluting with isohexane on a gradient of ethyl acetate (20–80%) and trituration with isohexane gave N-(tert-butyl)-6-(7-trifluoromethylimidazo[1,2-α] pyrimidin-3-yl)pyridin-2-ylamine (115 mg) as a pale yellow solid: $\delta_H$ (400 MHz, CDCl$_3$) 1.56 (9H, s), 7.42 (1H, d, J 7), 7.45 (1H, d, J 8), 7.68 (1H, dd, J 8 and 8), 7.78 (1H, d, J 8), 8.53 (1H, s), 10.33 (1H, d, J 7).

EXAMPLE 52

3-[6-(1H-[1,2,4]Triazol-1-yl)pyridin-2-yl]-7-trifluoromethylimidazo[1,2-α]pyrimidine A stirred solution of 2,6-dibromopyridine (2.0 g, 8.3 mmol) and 1,2,4-triazole sodium salt (1.0 g, 9.9 mmol) in dimethylsulfoxide (10 ml) was heated at 60° C. for 5 h. After cooling to ambient temperature the reaction was diluted with water and extracted into dichloromethane. Combined organic extracts were washed with water and saturated brine then dried over magnesium sulfate, filtered and evaporated in vacuo to give a solid. Purification by chromatography on silica gel eluting with dichloromethane, then dichloromethane containing 5% methanol, gave 2-bromo-6-(1H-[1,2,4]triazol-1-yl)pyridine (0.84 g) as a white solid: $\delta_H$ (400 MHz, CDCl$_3$) 7.49 (1H, d, J 8), 7.74 (1H, dd, J 8 and 8), 7.87 (1H, d, J 8), 8.09 (1H, s), 9.15 (1H, s); m/z (ES$^+$) 224/226 (M$^+$+H).

2-Bromo-6-(1H-[1,2,4]triazol-1-yl)pyridine (0.25 g, 1.13 mmol) was coupled to 3-tributylstannyl-7-trifluoromethylimidazo[1,2-α]pyrimidine (1.13 mmol) by the method of Example 1. Purification by chromatography on silica gel eluting with ethyl acetate on a gradient of methanol (0–10%) and trituration with ethyl acetate gave 3-[6-(1H-[1,2,4]triazol-1-yl)pyridin-2-yl]-7-trifluoromethylimidazo[1,2-α]pyrimidine (117 mg) as a pale yellow solid: $\delta_H$ (400 MHz, CDCl$_3$) 7.44 (1H, d, J 7), 7.84 (1H, d, J 8), 7.90 (1H, d, J 8), 8.07 (1H, dd, J 8 and 8), 8.19 (1H, s), 8.59 (1H, s), 9.12 (1H, s), 10.16 (1H, d, J 7); m/z (ES$^+$) 331 (M$^+$+H).

EXAMPLE 53

3-[6-(Isothiazol-4-yl)pyridin-2-yl]-7-trifluoromethylimidazo[1,2-α]pyrimidine

A degassed solution of 4-bromoisothiazole (1.43 g, 8.7 mmol) and bis(neopentyl glycolato)diboron (1.97 g, 8.7 mmol) was reacted as in Example 19 and gave 4-(5,5-dimethyl-[1,3,2]dioxaborinan-2-yl)isothiazole (0.85 g) as an off-white solid: $\delta_H$ (400 MHz, CDCl$_3$) 1.03 (6H, s), 3.76 (2H, s), 8.74 (1H, s), 9.02 (1H, s); m/z (ES$^+$) 130 (M$^+$+H).

A degassed solution of 2,6-dibromopyridine (0.86 g, 3.56 mmol) and 4-(5,5-dimethyl-[1,3,2]dioxaborinan-2-yl)isothiazole (0.35 g, 1.78 mmol) in dry 1,4-dioxane (10 ml) was stirred under an atmosphere of nitrogen, then cesium carbonate (1.20 g, 3.68 mmol) and tetrakis(triphenylphosphine)-palladium(0) (0.10 g, 5 mol %) added. This mixture was heated to reflux for 18 h. After cooling to ambient temperature, solvent was removed in vacuo, the residue dissolved in dichloromethane, washed with water and saturated brine, then dried over magnesium sulfate, filtered and evaporated in vacuo to give a solid. Purification by chromatography on silica gel, eluting with dichloromethane on a gradient of methanol (0–5%), gave 2-bromo-6-(isothiazol-4-yl)pyridine (0.33 g) as a white solid: $\delta_H$ (400 MHz, CDCl$_3$) 7.42 (1H, dd, J 7 and 2), 7.60 (2H, m), 9.01 (1H, s), 9.16 (1H, s); m/z (ES$^+$) 240/242 (M$^+$+H).

2-Bromo-6-(isothiazol-4-yl)pyridine (0.27 g, 1.13 mmol) was coupled to 3-tributylstannyl-7-trifluoromethylimidazo[1,2-α]pyrimidine (1.13 mmol) by the method of Example 1. Purification by chromatography on silica gel eluting with isohexane on a gradient of ethyl acetate (20–80%) and trituration with isohexane gave 3-[6-(isothiazol-4-yl)pyridin-2-yl]-7-trifluoromethylimidazo[1,2-α]pyrimidine (130 mg) as a pale yellow solid: $\delta_H$ (400 MHz, CDCl$_3$) 7.41 (1H, d, J 7), 7.62 (1H, d, J 8), 7.78 (1H, d, J 8), 7.92 (1H, dd, J 8 and 8), 8.56 (1H, s), 9.12 (1H, s), 9.13 (1H, s), 10.45 (1H, d, J 7); m/z (ES$^+$) 347 (M$^+$+H).

EXAMPLE 54

3-(6-Isopropoxypyridin-2-yl)-7-trifluoromethylimidazo[1,2-α]pyrimidine

Sodium (0.50 g, 21.7 mmol) was dissolved in isopropanol (50 ml) under an atmosphere of nitrogen with warming at 80° C., then allowed to cool to ambient temperature. 2,6-Dibromopyridine (10.0 g, 41.4 mmol) was added and the solution heated to 90° C. After 5 h the cooled reaction mixture was partitioned between diethyl ether (150 ml) and water (100 ml). Diethyl ether extracts were washed with water and saturated brine then dried over magnesium sulphate, filtered and evaporated in vacuo to give a semi-solid. Addition of isohexane, filtration and concentration in vacuo gave a residue that was purified by chromatography on silica gel eluting with dichloromethane to give 2-bromo-6-isopropoxypyridine (2.1 g) as a colourless liquid: $\delta_H$ (400 MHz, CDCl$_3$) 1.33 (6H, d, J 6), 5.28 (1H, quin, J 6), 6.60 (1H, d, J 8), 7.00 (1H, d, J 7), 7.38 (1H, dd, J 7 and 8); m/z (ES$^+$) 214/216 (M$^+$+H).

2-Bromo-6-isopropoxypyridine (0.32 g, 1.58 mmol) was coupled to 3-tributylstannyl-7-trifluoromethylimidazo[1,2-α]pyrimidine (1.13 mmol) by the method of Example 1. Purification by chromatography on silica gel eluting with isohexane on a gradient of ethyl acetate (20–40%) and trituration with isohexane gave 3-(6-isopropoxypyridin-2-yl)-7-(trifluoromethyl)imidazo[1,2-α]pyrimidine (130 mg) as a pale yellow solid: $\delta_H$ (400 MHz, CDCl$_3$) 1.45 (6H, d, J 6), 5.29 (1H, quin, J 6), 6.69 (1H, d, J 8), 7.34 (1H, d, J 7), 7.39 (1H, d, J 7), 7.70 (1H, dd, J 8 and 7), 8.46 (1H, s), 10.26 (1H, d, J 7); m/z (ES$^+$) 323 (M$^+$+H).

EXAMPLE 55

3-(6-Ethoxypyridin-2-yl)-7-trifluoromethylimidazo[1,2-α]pyrimidine

Sodium (0.48 g, 20.9 mmol) was dissolved in ethanol (50 ml) under an atmosphere of nitrogen at ambient temperature. 2,6-Dibromopyridine (10.0 g, 41.4 mmol) was added and the solution heated to reflux. After 6 h the cooled reaction mixture was partitioned between diethyl ether (150 ml) and water (100 ml). Diethyl ether extracts were washed with water and saturated brine then dried over magnesium sulphate, filtered and evaporated in vacuo to give a semi-solid. Addition of isohexane, filtration and concentration in vacuo gave a residue that was purified by chromatography on silica gel eluting with 80% dichloromethane-isohexane to give 2-bromo-6-ethoxypyridine (1.7 g) as a colourless liquid: $\delta_H$ (400 MHz, CDCl$_3$) 1.38 (3H, t, J 7), 4.34 (2H, quartet, J 7), 6.65 (1H, d, J 8), 7.02 (1H, d, J 7), 7.40 (1H, dd, J 7 and 8); m/z (ES$^+$) 202/204 (M$^+$+H).

2-Bromo-6-ethoxypyridine (0.30 g, 1.48 mmol) was coupled to 3-tributylstannyl-7-trifluoromethylimidazo[1,2-α]pyrimidine (1.13 mmol) by the method of Example 1. Purification by chromatography on silica gel eluting with isohexane on a gradient of ethyl acetate (20–40%) and trituration with isohexane gave 3-(6-ethoxypyridin-2-yl)-7-(trifluoromethyl)imidazo[1,2-α]pyrimidine (90 mg) as a pale yellow solid: $\delta_H$ (400 MHz, CDCl$_3$) 1.50 (3H, t, J 7), 4.45 (2H, quartet, J 7), 6.73 (1H, d, J 8), 7.34 (1H, d, J 7), 7.41 (1H, d, J 7), 7.71 (1H, dd, J 8 and 7), 8.46 (1H, s), 10.31 (1H, d, J 7); m/z (ES$^+$) 309 (M$^+$+H).

EXAMPLE 56

6-(7-Trifluoromethylimidazo[1,2-α]pyrimidin-3-yl)-2,2'-bipyridine

2-Tri-n-butylstannylpyridine (3.80 g, 8.2 mmol) was added to a degassed and stirred solution of 2,6-dibromopyridine (2.00 g, 8.3 mmol) and tetrakis(triphenylphosphine)palladium(0) (5 mol %) in tetrahydrofuran (30 ml) under an atmosphere of nitrogen then heated to reflux for 48 h. Solvent was removed in vacuo and purification by chromatography on silica gel eluting with dichloromethane followed by trituration with isohexane gave 6-bromo-2,2'-bipyridine (0.45 g) as a white solid: $\delta_H$ (400 MHz, CDCl$_3$) 7.31–7.34 (1H, m), 7.49 (1H, d), 7.67 (1H, dd), 7.80–7.84 (1H, m), 7.37–8.42 (2H, m), 8.66–8.68 (1H, m); m/z (ES$^+$) 234/236 (M$^+$+H).

6-Bromo-2,2'-bipyridine (0.35 g, 1.44 mmol) was coupled to 3-tributylstannyl-7-trifluoromethylimidazo[1,2-α]pyrimidine (1.13 mmol) by the method of Example 1. Purification by chromatography on silica gel eluting with isohexane on a gradient of ethyl acetate (20–100%) and trituration with isohexane gave 6-(7-trifluoromethylimidazo[1,2-α]pyrimidin-3-yl)-2,2'-bipyridine (130 mg) as a pale yellow solid: $\delta_H$ (400 MHz, CDCl$_3$) 7.39–7.43 (2H, m), 7.85 (1H, d, J 8), 7.89–7.94 (1H, m), 7.99 (1H, dd, J 8 and 8), 8.31 (1H, d, J 8), 8.38 (1H, d, J 8), 8.56 (1H, s), 8.75–8.80 (1H, m), 10.53 (1H, d, J 7); m/z (ES$^+$) 342 (M$^+$+H).

EXAMPLE 57

6-(7-Trifluoromethylimidazo[1,2-α]pyrimidin-3-yl)-2,4'-bipyridine

4-Tri-n-butylstannylpyridine (3.30 g, 8.9 mmol) was added to a degassed and stirred solution of 2,6-dibromopyridine (2.00 g, 8.3 mmol) and tetrakis(triphenylphosphine)palladium(0) (5 mol %) in tetrahydrofuran (30 ml) under an atmosphere of nitrogen then heated to reflux for 48 h. Solvent was removed in vacuo and purification by chromatography on silica gel eluting with dichloromethane followed by trituration with isohexane gave 6-bromo-2,4'-bipyridinyl (1.05 g) as a white solid: $\delta_H$ (400 MHz, CDCl$_3$) 7.52–7.57 (1H, m), 7.66–7.70 (1H, m), 7.86 (2H, m), 8.10–8.50 (1H, m), 8.72–8.76 (1H, m), 8.77–8.81 (1H, m); m/z (ES$^+$) 234/236 (M$^+$+H).

6-Bromo-2,4'-bipyridine (0.34 g, 1.44 mmol) was coupled to 3-tributylstannyl-7-trifluoromethylimidazo[1,2-α]pyrimidine (1.13 mmol) by the method of Example 1. Purification by chromatography on silica gel eluting with isohexane on a gradient of ethyl acetate (20–100%) and trituration with isohexane gave 6-(7-trifluoromethylimidazo[1,2-α]pyrimidin-3-yl)-2,4'-bipyridine (180 mg) as a pale yellow solid: $\delta_H$ (400 MHz, CDCl$_3$) 7.43 (1H, d, J 7), 7.77 (1H, d, J 8), 7.88–7.91 (3H, m), 7.98 (1H, dd, J 8 and 8), 8.59 (1H, s), 8.80–8.85 (1H, m), 10.51 (1H, d, J 7); m/z (ES$^+$) 342 (M$^+$+M).

EXAMPLE 58

3-(6-Methoxymethylpyridin-2-yl)-7-trifluoromethylimidazo[1,2-α]pyrimidine

2-Bromo-6-methoxymethylpyridine (0.27 g, 1.34 mmol; prepared according to Shawcross et al. in *J. Heterocyclic Chem.*, 1993, 33(2), 563–565) was coupled to 3-tributylstannyl-7-trifluoromethylimidazo[1,2-α]pyrimidine (1.34 mmol) by the method of Example 1. Purification by chromatography on silica gel eluting with isohexane on a gradient of ethyl acetate (20–100%) and trituration with isohexane gave 3-(6-methoxymethylpyridin-2-yl)-7-trifluoromethylimidazo[1,2-α]pyrimidine (15 mg) as a yellow solid: $\delta_H$ (400 MHz, CDCl) 3.54 (3H, s), 4.68 (2H, s), 7.34 (1H, d, J 7), 7.39 (1H, d, J 7), 7.73 (1H, d, J 7), 7.84 (1H, t, J 7), 8.52 (1H, s), 10.51 (1H, d, J 7); m/z (ES$^+$) 309 (M$^+$+H).

EXAMPLE 59

3-[6-(Thien-3-yl)pyridin-2-yl]-7-trifluoromethylimidazo[1,2-α]pyrimidine

Tetrakis(triphenylphosphine)palladium(0) (5 mol %) was added to a degassed and stirred mixture of 2,6-dibromopyridine (3.78 g, 15.6 mmol) and thiophene-3-boronic acid (2.20 g, 16.8 mmol) in tetrahydrofuran (40 ml) under an atmosphere of nitrogen then heated to reflux for 24 h. Solvent was removed in vacuo and purification by chromatography on silica gel eluting with a gradient of diethyl ether-isohexane (5–10%) gave 2-bromo-6-(thien-3-yl)pyridine (2.20 g) as a white solid: $\delta_H$ (400 MHz, CDCl$_3$) 7.32–7.41 (2H, m), 7.53–7.55 (2H, m), 7.61–7.64 (1H, m), 7.94–7.96 (1H, m); m/z (ES$^+$) 240/242 (M$^+$+H).

2-Bromo-6-(thien-3-yl)pyridine (2.20 g, 9.1 mmol) was coupled to 3-tributylstannyl-7-trifluoromethylimidazo[1,2-α]pyrimidine (9.0 mmol) by the method of Example 1. Purification by chromatography on silica gel eluting with isohexane on a gradient of ethyl acetate (10–80%) and trituration with isohexane followed by crystallisation from ethyl acetate-isohexane gave 3-[6-(thien-3-yl)pyridin-2-yl]-7-trifluoromethyl-imidazo[1,2-α]pyrimidine (350 mg) as a pale yellow solid: $\delta_H$ (400 MHz, CDCl$_3$) 7.40 (1H, d, J 7), 7.48–7.50 (1H, m), 7.60 (1H, d, J 8), 7.69–7.73 (2H, m), 7.86 (1H, dd, J 8 and 8), 7.92–7.94 (1H, m), 8.54 (1H, s), 10.56 (1H, d, J 7); m/z (ES$^+$) 347 (M$^+$+H).

EXAMPLE 60

7-(1,1-Dimethoxyethyl)-3-[2-(pyridin-4-yl)pyrimidin-4-yl]imidazo[1,2-α]pyrimidine Boron trifluoride diethyl etherate (17.03 g, 120.0 mmol) was added dropwise over 15 min to a cooled (−40° C.) solution of triethyl orthoformate (14.82 g, 100.0 mmol) in dichloromethane (150 ml). Stirring was continued for 10 min then the solution was transferred to an ice-water bath and stirred at 0° C. for 20 min. The mixture was cooled to −78° C. and 3,3-dimethoxybutan-2-one (6.61 g, 50.0 mmol) was added followed by dropwise addition of N,N-diisopropylethylamine (19.39 g, 150.0 mmol) over 15 min. After stirring at −78° C. for 15 min the reaction was allowed to reach ambient temperature before pouring the resulting orange solution into a mixture of saturated sodium hydrogencarbonate solution (500 ml) and dichloromethane (200 ml). This mixture was vigorously stirred for 15 min, the organic phase was separated, washed with ice-cold 1M sulphuric acid solution (2×300 ml), ice-cold water (2×300 ml), dried over anhydrous magnesium sulfate and concentrated to give crude 1,1-diethoxy-4,4-dimethoxypentan-3-one (14 g, >100%) as an orange oil: $\delta_H$ (360 MHz, CDCl$_3$) 1.18 (6H, t, J 7), 1.36 (3H, s), 2.93 (1H, d, J 6), 3.23 (3H, s), 3.25 (3H, s), 3.51–3.73 (4H, m), 5.03 (1H, t, J 6).

A suspension of sodium methoxide (3.1 g, 57 mmol) and 2-aminoimidazole hemisulfate (6.6 g, 50 mmol) in methanol (50 ml) was heated at 80° C. for 30 min before adding a solution of crude 1,1-diethoxy-4,4-dimethoxypentan-3-one (14 g) in methanol (50 ml). The reaction was heated at 80° C. for 12 h, cooled to ambient temperature then evaporated to dryness. The residue was suspended in dichloromethane and the solids removed by filtration. Purification of the filtrate by chromatography on silica gel eluting with dichloromethane (containing 1% conc. ammonia) on a gradient of methanol (1–5%) afforded an orange solid. Trituration with 20% diethyl ether in isohexane gave 7-(1,1-dimethoxyethyl)imidazo[1,2-α]pyrimidine (6.73 g, 65% for sequence) as a cream-coloured solid: $\delta_H$ (400 MHz, CDCl$_3$) 1.70 (3H, s), 3.28 (6H, s), 7.30 (1H, d, J 7), 7.55 (1H, d, J 1), 7.84 (1H, d, J 1), 8.43 (1H, d, J 7).

A mixture of 7-(1,1-dimethoxyethyl)imidazo[1,2-α]pyrimidine (5.3 g, 26 mmol), potassium bromide (3.1 g, 26 mmol) and sodium acetate (3.2 g, 39 mmol) in methanol (50 ml) was cooled to 0° C. before dropwise addition of bromine (4.5 g, 28 mmol) over 10 min. After stirring at 0° C. for a further 15 min the reaction was treated with 1M sodium sulphite solution (5 ml) and the solvent removed in vacuo. The residue was treated with dichloromethane (100 ml) then saturated sodium hydrogencarbonate solution (100 ml) was added. After stirring vigorously for 10 min the organic layer was collected, washed with 1M sodium sulphite solution (100 ml), water, brine, dried over anhydrous sodium sulfate, filtered and concentrated in vacuo. Trituration of the residue with diethyl ether furnished 3-bromo-7-(1,1-dimethoxyethyl)imidazo[1,2-α]pyrimidine (5.05 g, 69%) as a cream-coloured solid: $\delta_H$ (360 MHz, CDCl$_3$) 1.70 (3H, s), 3.28 (6H, s), 7.43 (1H, d, J 7), 7.82 (1H, s), 8.39 (1H, d, J 7).

To a solution of 3-bromo-7-(1,1-dimethoxyethyl)imidazo[1,2-α]pyrimidine (1.0 g, 3.5 mmol) at −45° C. was added isopropylmagnesium chloride (2.6 ml of a 2M solution in THF, 5.2 mmol) dropwise. After stirring at −45° C. for 1.5 h tri-n-butylstannyl chloride (1.52 ml, 5.6 mmol) was added dropwise. The solution was stirred at −45° C. for 15 min then the cooling bath was removed and the solution stirred at room temperature for 1.5 h. After this time half of the solution was taken and degassed with N$_2$ for 15 min. 4-Chloro-2-(pyridin-4-yl)pyrimidine (prepared according to *J. Med. Chem.*, 1982, 25(7), 837–842) (487 mg, 2.55 mmol) and tetrakis(triphenylphosphine)palladium(0) (294 mg, 0.26 mmol) were then added and the mixture heated at reflux for 18 h. After this time the solvent was evaporated and the residue partitioned between dichloromethane (2×40 ml) and water (40 ml). The combined organic layers were washed with brine (40 ml), dried (MgSO$_4$) and evaporated. The residue was chromatographed on silica gel, eluting with 1:1 isohexane:ethyl acetate followed by dichloromethane:MeOH (97:3), to afford 7-(1,1-dimethoxyethyl)-3-[2-(pyridin-4-yl)pyrimidin-4-yl]imidazo[1,2-α]pyrimidine (171 mg, 28%) as an off-white solid: $\delta_H$ (360 MHz, CDCl$_3$) 1.76 (3H, s), 3.33 (6H, s), 7.66–7.69 (2H, m), 8.28 (2H, dd, J 4.6 and 1.5), 8.60 (1H, s), 8.80–8.90 (3H, m), 10.30 (1H, d, J 7.3); m/z (ES+) 363 (M$^+$+H).

EXAMPLE 61

2-{3-[2-(3-Nitrophenyl)pyrimidin-4-yl]imidazo[1,2-α]pyrimidin-7-yl}propan-2-ol

A mixture of 3-(2-chloropyrimidin-4-yl)-7-(1-methyl-1-triethylsilanyloxyethyl)imidazo[1,2-α]pyrimidine (prepared according to Example 34) (250 mg, 0.62 mmol), 3-nitrobenzeneboronic acid (207 mg, 1.24 mmol) and tetrakis(triphenylphosphine)palladium(0) (71 mg, 10 mol %) in THF (3 ml) and 2N Na$_2$CO$_3$ solution (1.24 ml, 2.48 mnmol) was heated at reflux for 2.5 h. The mixture was cooled to room temperature, diluted with CH$_2$Cl$_2$ (30 ml), separated and concentrated to approximately 2 ml under reduced pressure. Purification by column chromatography on silica using 3% MeOH/CH$_2$Cl$_2$ afforded 7-(1-methyl-1-triethylsilanyloxyethyl)-3-[2-(3-nitrophenyl)pyrimidin-4-yl]imidazo[1,2-α]pyrimidine: m/z (ES+) 491 (M$^+$H+).

7-(1-Methyl-1-triethylsilanyloxyethyl)-3-[2-(3-nitrophenyl)-pyrimidin-4-yl]imidazo[1,2-α]pyrimidine in EtOH (10 ml) was treated with conc. HCl (10 drops) and stirred at room temperature for 12 h. The crude mixture was poured onto an SCX cartridge (2 gram) and washed firstly with MeOH (20 ml) to remove the impurities and then 2N NH$_3$ in MeOH (20 ml) to elute the desired compound. Removal of the solvent under reduced pressure afforded 2-{3-[2-(3-nitrophenyl)pyrimidin-4-yl]imidazo[1,2-α]pyrimidin-7-yl}propan-2-ol (66 mg, 28%): $^1$H NMR (360 MHz, CDCl$_3$) δ 10.31 (1H, d, J 7.3), 9.31 (1H, t, J 1.8), 8.83 (1H, d, J 5.5), 8.80 (1H, d, J 8.0), 8.55 (1H, s), 8.40 (1H, d, J 8.0), 7.75 (1H, t, J 8.0), 7.66 (1H, d, J 5.5), 7.40 (1H, d, J 7.3), 1.68 (6H, s); m/z (ES$^+$) 377 (M+H$^+$).

EXAMPLE 62

2-{3-[2-(3-Fluorophenyl)pyrimidin-4-yl]imidazo[1,2-α]pyrimidin-7-yl}propan-2-ol 3-(2-Chloropyrimidin-4-yl)-7-(1-methyl-1-triethylsilanyloxyethyl)-imidazo[1,2-α]pyrimidine (250 mg, 0.62 mmol) and 3-fluorobenzene-boronic acid (173 mg, 1.24 mmol) were reacted as described in Example 61. Purification by column chromatography on silica using 3% MeOH/CH$_2$Cl$_2$ gave 3-[2-(3-fluorophenyl)pyrimidin-4-yl]-7-(1-methyl-1-triethylsilanyloxyethyl)imidazo[1,2-α]pyrimidine: m/z (ES$^+$) 464 (M+H$^+$).

The foregoing compound was deprotected as described in Example 61 and purified on an SCX cartridge to afford 2-(3-[2-{3-fluorophenyl)pyrimidin-4-yl]imidazo[1,2-α]pyrimidin-7-yl}propan-2-ol (141 mg, 65%): $^1$H NMR (360 MHz, d$^6$-DMSO) δ 10.19 (1H, d, J 7.3), 8.92 (1H, d, J 5.5), 8.83 (1H, s), 8.32 (1H, d, J 7.9), 8.15 (1H, dt, J 10.4, 1.6), 8.03 (1H, d, J 5.5), 7.76 (1H, d, J 7.3), 7.68–7.60 (1H, m), 7.47–7.38 (1H, m), 5.61 (1H, s), 1.55 (6H, s); m/z (ES$^+$) 350 (M+H$^+$).

EXAMPLE 63

1-[3-(2-(Pyridin-4-yl)pyrimidin-4-yl)imidazo[1,2-α]pyrimidin-7-yl]ethanone

A solution of 7-(1,1-dimethoxyethyl)-3-[2-(pyridin-4yl)pyrimidin-4-yl]imidazo[1,2-α]pyrimidine (Example 60) (3 g, 8.3 mmol) in 2.5N HCl (60 ml) was heated at 50° C. for 4 h. To the cooled solution was added 5% MeOH/DCM (500 ml) then neutralized by portionwise addition of a saturated solution of NaHCO$_3$. Organic layer was separated and the aqueous re-extracted twice with 5% MeOH/DCM. Combined organics washed with brine, dried (MgSO$_4$) and concentrated in vacuo to give the crude residue. The crude was purified using 100 g silica bond elute cartridge, eluting with 1–2.5% MeOH/DCM, to afford 1-[3-(2-(pyridin-4-yl)pyrimidin-4-yl)imidazo[1,2-α]pyrimidin-7-yl]ethanone as a yellow solid (1.6 g, 61%): $^1$H NMR (400 MHz, d$^6$DMSO) δ 2.74 (3H, s), 7.92 (1H, d, J 7.2), 8.23 (1H, d, J 5.5), 8.37 (2H, dd, J 1.6, 4.3), 8.83 (2H, dd, J 1.6, 4.3), 9.04 (1H, d, J 5.5), 9.15 (1H, s), 10.39 (1H, d, J 7.4); m/z (ES$^+$) 317 (M+H$^+$).

EXAMPLE 64

6-[7-([1,2,4]Triazol-1-ylmethyl)imidazo[1,2-α]pyrimidinyl-3-yl]-2,3'-bipyridine dihydrochloride Pyruvic aldehyde dimethyl acetal (8.43 g, 71.4 mmol) and N,N-dimethylformamide dimethyl acetal (8.51 g, 71.4 mmol) were heated at 100° C. for 18 h. The mixture was concentrated to give a brown oil and was then added dropwise over 10 min to a warm (60° C.) suspension of 2-aminoimidazole hemisulfate (9.43 g, 71.4 mmol) in water (50 ml). The mixture was heated at 50° C. for 36 h, cooled to ambient temperature and then pre-adsorbed directly onto silica. Purification by chromatography on silica gel eluting with dichloromethane (containing 1% conc. ammonia) on a gradient of methanol (1–2%) gave a 3:1 mixture of 7-dimethoxymethyl-imidazo[1,2-α]pyrimidine and 5-dimethoxymethylimidazo[1,2-α]pyrimidine respectively. Crystallisation from toluene gave 7-dimethoxymethylimidazo[1,2-α]pyrimidine (2.20 g, 16%) as a brown crystalline solid: $\delta_H$ (400 MHz, CDCl$_3$) 3.50 (6H, s), 5.26 (1H, s), 7.15 (1H, d, J 7), 7.56 (1H, d, J 1), 7.84 (1H, d, J 1), 8.47 (1H, d, J 7).

7-Dimethoxymethylimidazo[1,2-α]pyrimidine (1.00 g, 5.18 mmol) was dissolved in 3N hydrochloric acid and heated at 48° C. for 14 h. The solution was layered with ethyl acetate (30 ml) and solid sodium hydrogencarbonate (1.06 g, 12.6 mmol) was added in portions over 5 min. The mixture was diluted with water (6 ml) and extracted with dichloromethane (5×50 ml). The combined organics were dried over anhydrous sodium sulfate, filtered and evaporated to give imidazo[1,2-α]pyrimidine-7-carbaldehyde (749 mg, 99%) as a yellow solid: $\delta_H$ (360 MHz, CDCl$_3$) 7.53 (1H, d, J 7), 7.77 (1H, d, J 1), 8.10 (1H, d, J 1), 8.60 (1H, d, J 7), 10.05 (1H, s).

Sodium triacetoxyborohydride (21.5 g, 102 mmol) was added portionwise over 20 min to a stirred solution of imidazo[1,2-α]pyrimidine-7-carbaldehyde (5.00 g, 34.0 mmol) in methanol (100 ml) and the solution left to stir at ambient temperature for 18 h. The solvent was evaporated, the residue redissolved in methanol (150 ml) and pre-adsorbed onto silica. Purification by chromatography on silica gel eluting with dichloromethane (containing 1% conc. ammonia) on a gradient of methanol (1–10%) gave imidazo[1,2-α]pyrimidin-7-ylmethanol (5.06 g, 99%) as a white solid: $\delta_H$ (360 MHz, DMSO) 4.57 (2H, d, J 6), 5.62 (1H, t, J 6), 7.13 (1H, d, J 7), 7.64 (1H, d, J 1), 7.86 (1H, d, J 1), 8.94 (1H, d, J 7).

To a solution of imidazo[1,2-α]pyrimidin-7-ylmethanol (4.64 g, 34.1 mmol) in dichloromethane under an atmosphere of nitrogen was added triphenylphosphine (10.6 g, 40.5 mmol) and carbon tetrabromide (13.4 g, 40.5 mmol). This mixture was stirred at room temperature for 2.5 h before addition of ethereal hydrogen chloride (1.0M, 100 ml) in a dropwise manner and allowed to stir at room temperature for a further 1 h. Reaction mixture was evaporated to dryness under reduced pressure and the resulting solid washed with dichloromethane followed by ether and then dried under vacuum to give 7-chloromethylimidazo[1,2-α]pyrimidine hydrochloride salt (5.0 g, 79%) as a pale brown solid: $\delta_H$ (360 MHz, d$^6$-DMSO) 5.06 (2H, s), 7.77 (1H, d, J 7), 8.31–8.35 (2H, m), 9.37 (1H, d, J 7); m/z (ES$^+$) 168, 170 (M$^+$+H).

To a solution of 1H-[1,2,4]triazole (2.2 g, 31.9 mmol) in anhydrous N,N-dimethylformamide (20 ml) under a nitrogen atmosphere was added sodium hydride (1.18 g, 29.4 mmol, 60% dispersion in oil) with caution in a portionwise manner. This mixture was then stirred for 20 min at room temperature. To a separate solution of 7-chloromethylimidazo[1,2-α]pyrimidine hydrochloride (5.0 g, 24.5 mmol), also dissolved in N,N-dimethylformamide (50 ml) under nitrogen, was added potassium carbonate (6.76 g, 49.0 mmol) and the mixture stirred for 5 min at room temperature. To the 7-chloromethylimidazo[1,2-α]pyrimidine solution was added the triazole sodium salt as a solution in N,N-dimethylformamide and the mixture stirred at room temperature for 16 h. Solvent was removed under reduced pressure and the resulting residue purified by flash column chromatography on silica eluting with dichloromethane, methanol and aqueous ammonia solution (33%) in the ratios 90:5:0.5 respectively to give 7-([1,2,4]triazol-1-ylmethyl)imidazo[1,2-α]pyrimidine (3.38 g, 69%) as a tan solid: $\delta_H$ (360 Mz, d$^6$-DMSO) 5.63 (2H, s), 6.90 (1H, d, J 7), 7.71 (1H, d, J 1.3), 7.91 (1H, d, J 1.4), 8.04 (1H, s), 8.73 (1H, s), 8.97 (1H, d, J 7); m/z (ES$^+$) 201 (M$^+$+H).

To 7-([1,2,4]triazol-1-ylmethyl)imidazo[1,2-α] pyrimidine (3.38 g, 16.9 mmol) in methanol (300 ml) saturated with potassium bromide was added sodium acetate (4.16 g, 50.7 mmol). This mixture was cooled (−10° C.) and bromine (2.70 g, 16.9 mmol) added dropwise over a five minute period. Stirring at this temperature was continued for 15 min before quenching the reaction with 5% (w/v) sodium sulphite solution (20 ml). Mixture was stirred for 15 min and methanol removed under reduced pressure. Residue was partitioned between dichloromethane (100 ml) and saturated sodium hydrogencarbonate solution (100 ml). Product was extracted into dichloromethane (4×100 ml) then the combined organic extracts were washed with brine (300 ml) and dried over anhydrous magnesium sulphate. Drying agent was removed by filtration and filtrate dried under reduced pressure to give 3-bromo-7-([1,2,4]triazol-1-ylmethyl) imidazo[1,2-α]pyrimidine (4.60 g, 97%) as a pale yellow solid: $\delta_H$ (360 MHz, d$_6$-DMSO) 5.69 (2H, s), 7.06 (1H, d, J 7), 7.88 (1H, s), 8.05 (1H, s), 8.74 (1H, s), 8.80 (1H, d, J 7); m/z (ES$^+$) 279, 281 (M$^+$+H).

To a cooled (−78° C.) solution of 3-bromo-7-([1,2,4] triazol-1-ylmethyl)-imidazo[1,2-α]pyrimidine (0.42 g, 1.50 mmol) in tetrahydrofuran (15 ml) was added isopropylmagnesium chloride (0.82 ml of a 2M solution in tetrahydrofuran, 2.37 mmol). Mixture was allowed to warm to −45° C. and stirring at this temperature was continued for 0.5 h. Mixture was recooled to −78° C., tributyltin chloride (0.47 ml, 1.72 mmol) added in a dropwise fashion, stirred for 10 min at −78° C. and then allowed to warm to ambient temperature. This process of Grignard formation with subsequent transmetallation to the stannane intermediate was repeated to encourage completion of the reaction giving 7-([1,2,4]triazol-1-ylmethyl)-3-tributylstannylimidazo[1,2-α]pyrimidine as a solution in tetrahydrofuran (ca. 0.1M); m/z (ES$^+$) 487, 489, 490 (M$^+$+H).

To the degassed solution of 7-([1,2,4]triazol-1-ylmethyl)-3-tributylstannylimidazo[1,2-α]pyrimidine was added 6-bromo-2,3'-bipyridine (prepared according to Example 49) (0.39 g, 1.65 mmol) and tetrakis(triphenylphosphine) palladium(0) (173 mg, 0.10 mmol) and the mixture heated at reflux for 3 h. The crude reaction was adsorbed onto silica and purified by chromatography on silica gel eluting with a dichloromethane, methanol, aqueous ammonia (33%) mixture in the volume ratios of 90:5:0.5 respectively to give 6-[7-([1,2,4]triazol-1-ylmethyl)imidazo[1,2-α]pyrimidin-3-yl]-2,3'-bipyridine as a hygroscopic solid following crystallisation from dichloromethane/ethyl acetate. Addition of an excess of 1M HCl in ether to a solution of the product in a methanol/ether solvent mixture gave 50 mg of the dihydrochloride salt as a white solid: $\delta_H$ (360 MHz, CDCl$_3$) 5.62 (2H, s), 6.96 (1H, d, J 7), 7.47 (1H, dd, J 4.7 and 4.7), 7.66 (1H, d, J 7.7), 7.78 (1H, d, J 7.9), 7.91 (1H, t, J 9), 8.05 (1H, s), 8.23–8.27 (1H, m), 8.36 (1H, s), 8.41 (1H, s), 8.71–8.72 (1H, m), 9.25 (1H, s), 10.30 (1H, d, J 7.2); m/z (ES$^+$) 355 (M$^+$+H).

EXAMPLE 65

2-[6-(7-([1,2,4]Triazol-1-ylmethyl)imidazo[1,2-α] pyrimidin-3-yl)pyridin-2-yl]benzonitrile trifluoroacetate 3-Bromo-7-([1,2,4]triazol-1-ylmethyl)imidazo[1,2-α] pyrimidine (0.2 g, 0.72 mmol) was coupled to 2-(6-bromopyridin-2-yl)benzonitrile (prepared according to Example 27) following the procedure in Example 64 and purified by LC/MS to give 2-[6-(7-([1,2,4]triazol-1-ylmethyl)imidazo[1,2-α]pyrimidin-3-yl)pyridin-2-yl]benzonitrile trifluoroacetate as a white solid: $\delta_H$ (400 MHz, CDCl$_3$) 5.67 (2H, s), 7.26 (1H, d, J 7.2), 7.60–7.67 (2H, m), 7.75 (1H, dd, J 8, 7 and 1), 7.89–8.04 (3H, m), 8.10 (1H, s), 8.50 (1H, bs), 8.60 (1H, bs), 10.56 (1H, s); m/z (ES$^+$) 379 (M$^+$+H).

EXAMPLE 66

6'-(7-Trifluoromethylimidazo[1,2-α]pyrimidin-3-yl)-2,2'-bipyridinyl-3-carbonitrile To a degassed solution of 2-chloro-6-tributylstannylpyridine (prepared according to S. Choppin et al. in *Org. Lett.*, 2000, 2, 803–5) (600 mg, 1.49 mmol) and 2-chloro-3-cyanopyridine (412 mg, 2.98 mmol) in THF was added tetrakis(triphenylphosphine)palladium(0) (60 mg, 0.05 mmol) and the mixture heated at reflux for 96 hours. The solvent was removed under reduced pressure and the crude product chromatographed on silica, on a gradient of dichloromethane to 2% methanol in dichloromethane, to afford 6'-chloro-2,2'-bipyridinyl-3-carbonitrile as a white solid (231 mg): $\delta_H$ (400 MHz, d$^6$-DMSO) 7.71–7.74 (2H, m), 8.11 (1H, t, J 7.8), 8.20–8.23 (1H, m), 8.48 (1H, dd, J 1.8, 8.0), 8.97 (1H, dd, J 1.8, 4.9); m/z (ES$^+$) 216, 218 (M$^+$+H).

The foregoing compound was coupled to 3-tributylstannyl-7-trifluoromethylimidazo[1,2-α]pyrimidine by the method of Example 1 to give 6'-(7-trifluoromethylimidazo[1,2-α]pyrimidin-3-yl)-2,2'-bipyridinyl-3-carbonitrile: $\delta_H$ (400 MHz, CDCl$_3$) 7.40–7.57 (2H, m), 7.99–8.08 (2H, m), 8.16–8.18 (1H, m), 8.25 (1H, dd, J 2.0, 7.8), 8.59 (1H, s), 8.96 (1H, dd, J 1.8, 4.9), 10.61 (1H, d, J 7.4); m/z (ES$^+$) 367 (M$^+$+H).

EXAMPLE 67

6'-[7-(1-Fluoro-1-methylethyl)imidazo[1,2-α]pyrimidin-3-yl]-2,2'-bipyridinyl-3-carbonitrile 6'-Chloro-2,2'-bipyridinyl-3-carbonitrile was coupled to 7-(1-fluoro-1-methylethyl)-3-tributylstannylimidazo[1,2-α]pyrimidine (prepared according to Example 25) by the method of Example 1 to give 6'-[7-(1-fluoro-1-methylethyl)imidazo[1,2-α]pyrimidin-3-yl)-2,2'-bipyridinyl-3-carbonitrile: $\delta_H$ (400 MHz, CDCl$_3$) 1.78 (3H, s), 1.84 (3H, s), 7.42 (1H, dd, J 2.0, 7.0), 7.55 (1H, dd, J 4.7, 7.8), 7.95 (1H, d, J 1.2), 7.99 (1H, t, J 7.8), 8.06–8.08 (1H, m), 8.24 (1H, dd, J 1.6, 7.8), 8.39 (1H, s), 8.94 (1H, dd, J 1.6, 4.7), 10.36 (1H, d, J 7.0); m/z 359 (M$^+$+H).

EXAMPLES 68 TO 109

The following compounds were made by methods analogous to those described above.

| Example No. | Z |
|---|---|
|  | 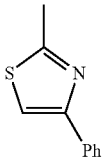 |
| 68 | 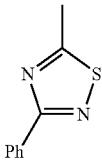 |
| 69 | 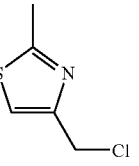 |
| 70 | 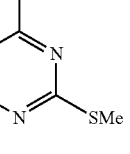 |
| 71 | 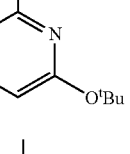 |
| 72 | 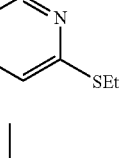 |
| 73 | 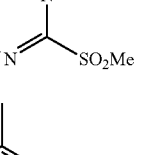 |
| 74 | 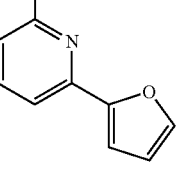 |
| 75 | 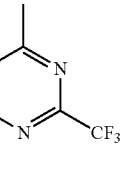 |
| 76 | 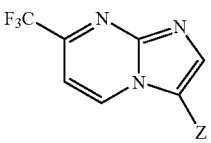 |

-continued
| Example No. | Z |
|---|---|
| 77 | 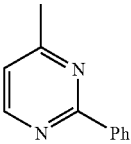 |
| 78 | 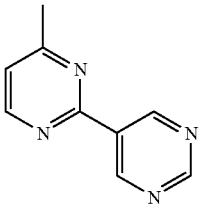 |
| 79 | 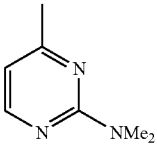 |
| 80 | 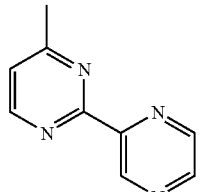 |
| | 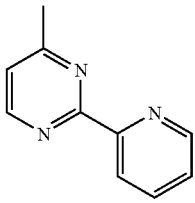 |
| 81 | 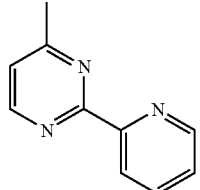 |
| 82 | 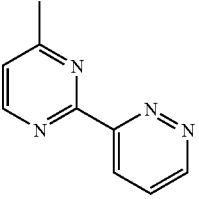 |
| 83 | 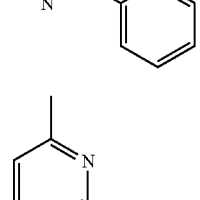 |
-continued
| Example No. | Z |
|---|---|
| 84 | 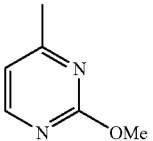 |
| 85 | 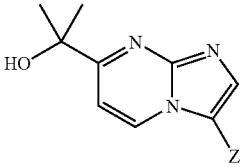 |
| 86 | 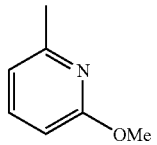 |
| 87 | 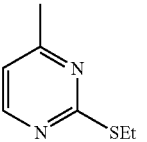 |
| 88 | 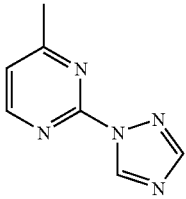 |
| 89 | 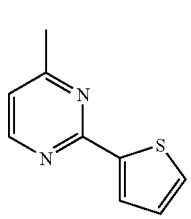 |
| 90 | 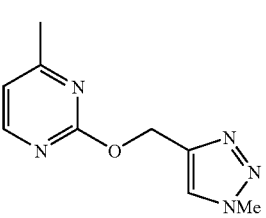 |
| 91 | 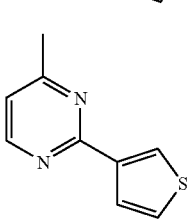 |

-continued
| Example No. | Z |
|---|---|
| 92 | 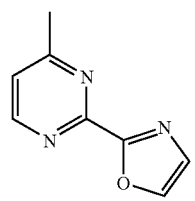 |
| 93 | 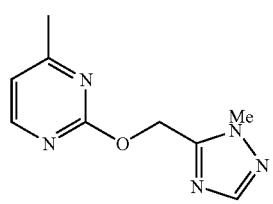 |
| 94 | 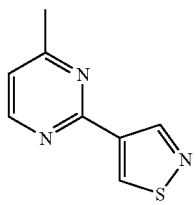 |
| 95 | 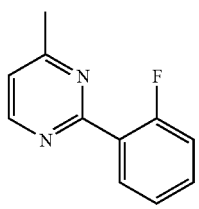 |
| 96 | 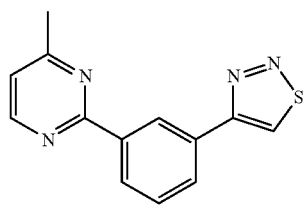 |
| 97 | 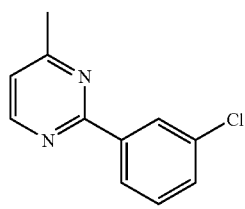 |
| 98 | 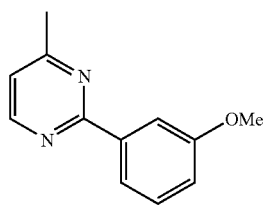 |
-continued
| Example No. | Z |
|---|---|
| 99 | 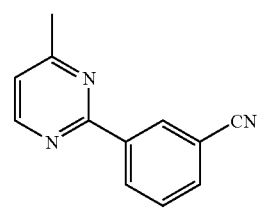 |
| 100 | 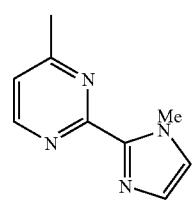 |
| 101 | 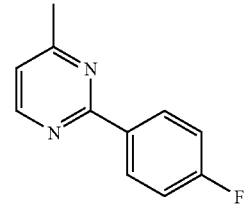 |
| 102 | 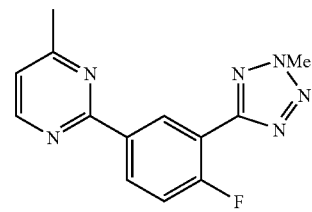 |
| 103 | 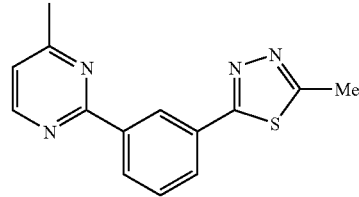 |
| 104 | 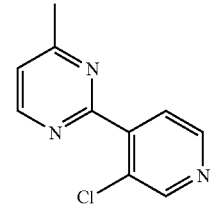 |
| 105 | 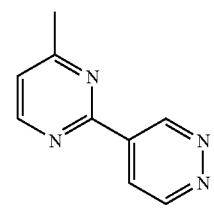 |

| Example No. | Z |
|---|---|
| 106 | (4-methylpyrimidin-2-yl)C(Me)(Me)(Me) |
| 107 | 6-methyl-2-(pyridin-4-yl)pyridine |
| 108 | 2-iodo-4-methylpyrimidine |
| 109 | 4-methyl-2-(2-methylimidazol-1-yl)pyrimidine |

EXAMPLE 110

2-{3-[2-(2,4-Difluorophenyl)pyrimidin-4-yl]imidazo[1,2-α]pyrimidin-7-yl}propan-2-ol 3-(2-Chloropyrimidin-4-yl)-7-(1-methyl-1-triethylsilanyloxyethyl)-imidazo[1,2-α]pyrimidine (250 mg, 0.62 mmol) and 2,4-difluorobenzeneboronic acid (196 mg, 1.24 mmol) were reacted together as described in Example 61. Purification by column chromatography on silica using 2.5% MeOH/CH$_2$Cl$_2$ gave 3-[2-(2,4-difluorophenyl)pyrimidin-4-yl]-7-(1-methyl-1-triethylsilanyloxyethyl)imidazo[1,2-α]pyrimidine: m/z (ES$^+$) 482 (M+H$^+$).

The foregoing compound was deprotected as described in Example 61, Step 2 and purified on an SCX cartridge to afford 2-{3-[2-(2,4-difluorophenyl)pyrimidin-4-yl]imidazo[1,2-α]pyrimidin-7-yl}propan-2-ol (72 mg, 32%): $^1$H NMR (360 MHz, CDCl$_3$) δ 10.19 (1H, d, J 7.2), 8.92 (1H, d, J 5.4), 8.52 (1H, s), 8.30–8.21 (1H, m), 7.60 (1H, d, J 5.4), 7.29 (1H, d, J 7.2), 7.10–6.95 (2H, m), 1.65 (6H, s); m/z (ES$^+$) 368 (M+H$^+$).

EXAMPLE 111

2-{3-[2-(3,4-Difluorophenyl)pyrimidin-4-yl]imidazo[1,2-α]pyrimidin-7-yl}propan-2-ol 3-(2-Chloropyrimidin-4-yl)-7-(1-methyl-1-triethylsilanyloxyethyl)-imidazo-[1,2-α]pyrimidine (250 mg, 0.62 mmol) and 3,4-difluorobenzeneboronic acid (196 mg, 1.24 mmol) were reacted together as described in Example 61. Purification by column chromatography on silica using 2.5% MeOH/CH$_2$Cl$_2$ gave 3-[2-(3,4-difluorophenyl)pyrimidin-4-yl]-7-(1-methyl-1-triethylsilanyloxyethyl)imidazo[1,2-α]pyrimidine: m/z (ES$^+$) 482 (M+H$^+$).

3-[2-(3,4-Difluorophenyl)pyrimidin-4-yl]-7-(1-methyl-1-triethylsilanyloxyethyl)imidazo[1,2-α]pyrimidine in EtOH (8 ml) was treated with conc. HCl (15 drops) and stirred at room temperature for 12 h. The resulting solid was filtered off and dried under reduced pressure. The resulting solid was added to a mixture of 1N NaOH (30 ml) and CH$_2$Cl$_2$ and stirred vigorously for 5 min. The organics were separated and the aqueous fraction extracted with CH$_2$Cl$_2$ (3×20 ml). The combined organic extracts were dried (MgSO$_4$) and concentrated under reduced pressure to yield 2-{3-[2-(3,4-difluorophenyl)pyrimidin-4-yl]imidazo[1,2-α]pyrimidin-7-yl}propan-2-ol (74 mg, 33%): $^1$H NMR (400 MHz, d$^6$-DMSO) δ 10.16 (1H, d, J 7.3), 8.90 (1H, d, J 5.5), 8.82 (1H, s), 8.40–8.30 (2H, m), 8.03 (1H, d, J 5.5), 7.73 (1H, d, J 7.3), 7.17–7.08 (1H, m), 7.61 (1H, s), 1.55 (6H, s).

EXAMPLE 112

2-{3-[2-(1-Benzyl-1,2,3,6-tetrahydropyridin-4-yl}pyrimidin-4-yl]imidazo[1,2-α]pyrimidin-7-yl)propan-2-ol Benzyl chloride (460 µl, 4.0 mmol) was added to a stirred suspension of 4-chloro-2-(pyridin-4-yl)pyrimidine (prepared according to *J. Med. Chem.*, 1982, 25(7), 837–842) (383 mg, 2.00 mmol) in MeCN (10 ml) and the mixture was heated at reflux for 30 h and then concentrated under reduced pressure. EtOH (5 ml) was then added, followed by NaBH$_4$ (151 mg, 4.0 mmol), and the mixture stirred at room temperature for 30 min. Water (10 ml) and EtOAc (70 ml) were added, separated and the organics washed with H$_2$O (20 ml), brine (20 ml) and concentrated under reduced pressure. The residue was purified by column chromatography on silica using 3% MeOH/CH$_2$Cl$_2$ as eluent to yield 2-(1-benzyl-1,2,3,6-tetrahydropyridin-4-yl)-4-chloropyrimidine (325 mg, 57%): $^1$H NMR (360 MHz, CDCl$_3$) δ 8.52 (1H, d, J 5.3), 7.40–7.23 (6H, m), 7.11 (1H, d, J 5.3), 3.66 (2H, s), 3.30–3.20 (2H, m), 2.80–2.63 (4H, m); m/z (ES$^+$) 286, 288 (1:1, M+H$^+$).

3-Bromo-7-(1-methyl-1-triethylsilanyloxyethyl)imidazo[1,2-α]pyrimidine (287 mg, 0.77 mmol) and 2-(1-benzyl-1,2,3,6-tetrahydropyridin-4-yl)-4-chloropyrimidine: (266 mg, 0.93 mmol) were reacted together as described in Example 39, Step 1. Purification by column chromatography on silica, using 4–7.5% MeOH/CH$_2$Cl$_2$, gave 3-[2-(1-benzyl-1,2,3,6-tetrahydropyridin-4-yl)pyrimidin-4-yl]-7-(1-methyl-1-triethylsilanyloxyethyl)imidazo[1,2-α]pyrimidine: m/z (ES$^+$) 540 (M+H$^+$).

The foregoing compound was deprotected as described in Example 61, Step 2 and purified on an SCX cartridge, followed by column chromatography on silica, using 10% MeOH/CH$_2$Cl$_2$ as eluent, to afford 2-{3-[2-(1-benzyl-1,2,3,6-tetrahydropyridin-4-yl)pyrimidin-4-yl]imidazo[1,2-α]pyrimidin-7-yl}propan-2-ol (20 mg, 6%): $^1$H NMR (360 MHz, CDCl$_3$) δ 10.24 (1H, d, J 7.3), 8.68 (1H, d, J 5.4), 8.44 (1H, s), 7.48–7.20 (8H, m), 3.70 (2H, s), 3.38–3.30 (2H, m), 2.85–2.75 (4H, m), 1.66 (6H, s); m/z (ES$^+$) 427 (M+H$^+$).

EXAMPLE 113

2-{3-[2-(1,1-Difluoroethyl)pyrimidin-4-yl]imidazo[1,2-α]pyrimidin-7-yl}propan-2-ol A solution of isopropylmagnesium chloride (4.2 mmol) in THF (2.0M, 2.1 ml) was added dropwise to a stirred solution of 2-iodo-4-methoxypyrimidine (prepared according to Leprete et al. in *Tetrahedron*, 2000, 56, 265–273) (1.0 g, 4.2 mmol) in THF (12 ml) at 0° C. under N$_2$. The reaction was stirred for 30 min at 0° C. and then DMA (409 µl, 4.4 mmol) was added. The reaction was stirred for 1 h and then quenched by addition of NH$_4$Cl solution (15 ml) and extracted with EtOAc (50 ml and 20 ml). The combined organics were concentrated under reduced pressure and purified by column chromatography on silica, using 75% Et2O/iso-hexanes as eluent, to yield 1-(4-methoxypyrimidin-2-yl)ethanone (206 mg, 32%): $^1$H NMR (360 MHz, CDCl$_3$) δ 8.59 (1H, d, J 5.7), 6.83 (1H, d, J 5.7), 4.08 (3H, s), 2.74 (3H, s); m/z (ES$^+$) 153 (M$^+$).

The foregoing compound (505 mg, 3.3 mmol) in 1,2-dichloroethane (20 ml) was treated with [bis(2-methoxyethyl)amino]sulfur trifluoride (1.66 ml, 9.9 mmol) and the reaction mixture was heated at reflux overnight. The mixture was poured into ice (50 ml) and neutralised by addition of NaHCO$_3$. The organic products were extracted with CH$_2$Cl$_2$ (2×30 ml) and then concentrated under reduced pressure. The crude residue was purified by column chromatography on silica, using 40% Et$_2$O/isohexanes as eluent, to yield 2-(1,1-difluoroethyl)-4-methoxypyrimidine (271 mg, 47%): $^1$H NMR (400 MHz, CDCl$_3$) δ 8.51 (1H, d, J 5.7), 6.77 (1H, d, J 5.7), 4.01 (3H, s), 2.04 (3H, t, J 18.5); m/z (ES$^+$) 175 (M+H$^+$).

The forementioned compound was heated in the presence of 5N HCl (15 ml) at reflux for 12 h and then concentrated under reduced pressure and dried under reduced pressure to yield 2-(1,1-difluoroethyl)pyrimidin-4-ol: $^1$H NMR (400 MHz, d$^6$-DMSO) δ 8.51 (1H, d, J 6.2), 6.65 (1H, d, J 6.2), 1.96 (3H, t, J 19.2).

The crude pyrimidinol (230 mg, 1.43 mmol) in 1,2-dichloroethane (10 ml) was heated at reflux in the presence of POCl$_3$ (669 µl, 7.2 mmol) for 16 h. Ice (20 ml) was added, the organics were extracted with CH$_2$Cl$_2$ (3×50 ml) and then concentrated under reduced pressure to yield 4-chloro-2-(1,1-difluoroethyl)pyrimidine (209 mg, 82%): $^1$H NMR (400 MHz, CDCl$_3$) δ 8.72 (1H, d, J 5.2), 7.45 (1H, d, J 5.2), 2.06 (3H, t, J 18.5); m/z (ES$^+$) 179, 181 (3:1, M+H$^+$).

3-Bromo-7-(1-methyl-1-triethylsilanyloxyethyl)imidazo[1,2-α]pyrimidine (567 mg, 1.4 mmol) and 4-chloro-2-(1,1-difluoroethyl)pyrimidine (209 mg, 1.17 mmol) were reacted together as described in Example 39, Step 1. Purification by column chromatography on silica using 3% MeOH/CH$_2$Cl$_2$ gave 3-[2-(1,1-difluoroethyl)pyrimidin-4-yl]-7-(1-methyl-1-triethylsilanyloxyethyl)imidazo[1,2-α]pyrimidine.

The foregoing compound in EtOH (8 ml) was treated with conc. HCl (15 drops) and stirred at room temperature for 4 h. The resulting mixture was poured onto an SCX cartridge (5 g) and washed firstly with MeOH to remove the impurities and then 2N NH$_3$ in MeOH to elute the desired compound. The fractions containing the desired material were concentrated under reduced pressure while dry loading onto MgSO$_4$. The residue was purified by column chromatography on silica, using 7% MeOH/dichloromethane containing 1% NH$_3$ solution as eluent, and then by preparative HPLC using 15–40% MeCN/[0.1% TFA/H$_2$O], to yield 2-{3-[2-(1,1-difluoroethyl)pyrimidin-4-yl]imidazo[1,2-α]pyrimidin-7-yl}propan-2-ol (37 mg, 8%): $^1$H NMR (400 MHz, d$^6$-DMSO) δ 10.05 (1H, d, J 7.2), 8.92 (1H, d, J 5.5), 8.90 (1H, s), 8.20 (1H, d, J 5.5), 7.71 (1H, d, J 7.2), 5.60 (1H, s), 2.13 (3H, t, J 19.1), 1.53 (6H, s); m/z (ES$^+$) 320 (M+H$^+$).

EXAMPLE 114

1-{4-[7-(1-Hydroxy-1-methylethyl)imidazo[1,2-α]pyrimidin-3-yl]pyrimidin-2-yl}ethanone 3-Bromo-7-(1-methyl-1-triethylsilanyloxyethyl)imidazo[1,2-α]pyrimidine (5.0 g, 13.5 mmol) and 2,4-diiodopyrimidine (prepared according to Leprete et al. in *Tetrahedron*, 2000, 56, 265–273) (5.6 g, 16.9 mmol) were reacted together as described in Example 39, Step 1. Purification by column chromatography on silica using 2.5% MeOH/CH$_2$Cl$_2$ gave 3-(2-iodopyrimidin-4-yl)-7-(1-methyl-1-triethylsilanyloxyethyl)imidazo[1,2-α]pyrimidine (4.97 g, 74%): $^1$H NMR (400 MHz, CDCl$_3$) δ 9.95 (1H, d, J 7.3), 8.47 (1H, s), 8.35 (1H, d, J 5.4), 7.66 (1H, d, J 7.3), 7.59 (1H, d, J 5.4), 1.66 (6H, s), 1.00 (9H, t, J 8.0), 0.67 (6H, q, J 8.0).

A solution of isopropylmagnesium chloride (10.8 mmol) in THF (2.0M, 5.4 ml) was added dropwise to a stirred solution of the forementioned compound (2.68 g, 5.4 mmol) in THF (70 ml) at −78° C. under N$_2$. The reaction was stirred for 30 min at −78° C. and then ethanal (665 µl, 11.9 mmol) was added. The reaction was warmed to room temperature, stirred for a further 30 min and then quenched by the addition of NH$_4$Cl solution (30 ml). The organics were extracted with EtOAc (3×50 ml), then concentrated under reduced pressure while dry loading onto MgSO$_4$. The residue was purified by column chromatography on silica, using 6% EtOH/EtOAc as eluent, to yield 1-{4-[7-(1-methyl-1-triethylsilanyl-oxyethyl)imidazo[1,2-α]pyrimidin-3-yl]pyrimidin-2-yl}ethanol (930 mg, 42%): $^1$H NMR (400 MHz, CDCl$_3$) δ 10.10 (1H, d, J 7.2), 8.67 (1H, d, J 5.5), 8.48 (1H, s), 7.61 (1H, d, J 7.2), 7.55 (1H, d, J 5.5), 5.03 (1H, quintet, J 5.1), 4.07 (1H, d, J 5.1), 1.62–1.55 (9H, m), 0.99 (9H, t, J 7.8), 0.67 (6H, q, J 7.8); m/z (ES$^+$) 414 (M+H$^+$).

Dess-Martin periodinane (1.02 g, 2.4 mmol) was added to a stirred solution of the above alcohol (500 mg, 1.2 mmol) in CH$_2$Cl$_2$ (20 ml) and the reaction was stirred for 3 h. Further CH$_2$Cl$_2$ (50 ml) was added and then washed with 2N NaOH (50 ml) and brine (30 ml). The organics were concentrated under reduced pressure and purified by column chromatography on silica, using 3% MeOH/CH$_2$Cl$_2$ as eluent, to yield 1-{4-[7-(1-methyl-1-triethylsilanyloxyethyl)imidazo[1,2-α]pyrimidin-3-yl]pyrimidin-2-yl}ethanone (320 mg, 64%): $^1$H NMR (360 MHz, CDCl$_3$) δ 10.33 (1H, d, J 7.2), 8.82 (1H, d, J 5.5), 8.53 (1H, s), 7.74 (1H, d, J 5.5), 7.67 (1H, d, J 7.2), 2.85 (3H, s), 1.70 (6H, s), 1.58 (6H, m), 0.99 (9H, t, J 7.8), 0.67 (6H, q, J 7.8); m/z (ES$^+$) 411 (M+H$^+$).

The foregoing compound (114 mg, 0.28 mmol) was deprotected as described in Example 61, Step 2 to yield after chromatography on silica, using 12–14% EtOH/EtOAc as eluent, 1-{4-[7-(1-hydroxy-1-methylethyl)-imidazo[1,2-α]pyrimidin-3-yl]pyrimidin-2-yl}ethanone (20 mg, 24%): $^1$H NMR (400 MHz, CDCl$_3$) δ 10.43 (1H, d, J 7.3), 8.84 (1H, d, J 5.4), 8.55 (1H, s), 7.77 (1H, d, J 5.4), 7.36 (1H, d, J 7.3), 5.59 (1H, s), 2.84 (3H, s), 1.66 (6H, s); m/z (ES$^+$) 298 (M+H$^+$).

EXAMPLE 115

2-{3-[2-(1-Hydroxy-1-methylethyl)pyrimidin-4-yl]imidazo[1,2-α]pyrimidin-7-yl}propan-2-ol A solution of methylmagnesium chloride (1.65 mmol) in THF (3.0 M, 550 µl) was added dropwise to a stirred solution of 1-{4-[7-(1-methyl-1-triethylsilanyloxyethyl)imidazo[1,2-α]pyrimidin-3-yl]pyrimidin-2-yl}ethanone (Example 114, Step 3) (452 mg, 1.1 mmol) in THF (10 ml) at −78° C. under N$_2$. The reaction was stirred overnight slowly warming to room temperature and then quenched by the addition of NH$_4$Cl solution (30 ml). The organics were extracted with EtOAc (3×50 ml), then concentrated under reduced pressure while dry loading onto MgSO$_4$. The residue was purified by column chromatography on silica, using 6% iPrOH/EtOAc as eluent, to yield 2-{4-[7-(1-methyl-1-triethylsilanyl-oxyethyl)imidazo[1,2-α]pyrimidin-3-yl]pyrimidin-2-yl}propan-2-ol (330 mg, 70%): ¹H NMR (400 MHz, CDCl₃) δ 10.05 (1H, d, J 7.3), 8.67 (1H, d, J 5.5), 8.48 (1H, s), 7.61 (1H, d, J 7.2), 7.55 (1H, d, J 5.5), 4.10–3.97 (2H, m), 1.21 (6H, s), 1.20 (6H, s), 0.99 (9H, t, J 7.9), 0.67 (6H, q, J 7.9); m/z (ES⁺) 428 (M+H⁺).

The foregoing compound (65 mg, 0.15 mmol) in EtOH (15 ml) was treated with conc. HCl (10 drops) and stirred at room temperature for 6 h. The resulting mixture was concentrated under reduced pressure and then dissolved in DMSO (4 ml) and purified by preparative HPLC using 10–20% MeCN/[0.1% TFA/H₂O]. The MeCN was removed under reduced pressure and NaHCO₃ solution (50 ml) added. The organics were extracted with CH₂Cl₂ (2×100 ml), dried (MgSO₄) and concentrated to yield 2-{3-[2-(1-hydroxy-1-methylethyl)pyrimidin-4-yl]imidazo[1,2-α]pyrimidin-7-yl}propan-2-ol (20 mg, 42%): ¹H NMR (360 MHz, CDCl₃) δ 10.16 (1H, d, J 7.3), 8.70 (1H, d, J 5.5), 8.51 (1H, s), 7.57 (1H, d, J 5.5), 7.32 (1H, d, J 7.3), 4.56 (1H, s), 4.24 (1H, s), 1.69 (6H, s), 1.66 (6H, s); m/z (ES⁺) 314 (M+H⁺).

EXAMPLE 116

2-{3-[2-(1-Fluoro-1-methylethyl)pyrimidin-4-yl]imidazo[1,2-α]pyrimidin-7-yl}propan-2-ol (Diethylamino)sulphur trifluoride (150 mg, 0.95 mmol) was added to a stirred solution of 2-{4-[7-(1-methyl-1-triethylsilanyloxyethyl)-imidazo[1,2-α]pyrimidin-3-yl]pyrimidin-2-yl}propan-2-ol (Example 115, Step 1) (200 mg, 0.47 mmol) in 1,2-dichloroethane (5 ml) at room temperature under N₂ and the reaction was stirred overnight. Water (20 ml) was added followed by NaHCO₃ solution (20 ml) and then the organics were extracted with CH₂Cl₂ (3×50 ml) and concentrated under reduced pressure. The residue was purified by column chromatography on silica using 7% EtOH/EtOAc to yield 3-[2-(1-fluoro-1-methylethyl)pyrimidin-4-yl]-7-(1-methyl-1-triethylsilanyloxyethyl)imidazo[1,2-α]pyrimidine (60 mg, 30%): ¹H NMR (400 MHz, CDCl₃) δ 10.25 (1H, d, J 7.3), 8.71 (1H, d, J 5.5), 8.48 (1H, s), 7.60 (1H, d, J 7.2), 7.55 (1H, d, J 5.5), 1.87 (6H, d, J 21.6), 0.99 (9H, t, J 8.0), 0.68 (6H, q, J 8.0); m/z (ES⁺) 430 (M+H⁺).

3-[2-(1-Fluoro-1-methylethyl)pyrimidin-4-yl]-7-(1-methyl-1-triethylsilanyloxyethyl)imidazo[1,2-α]pyrimidine (60 mg, 0.14 mmol) was deprotected as described in Example 61, Step 2 to yield after chromatography on silica, using 6–12% MeOH/CH₂Cl₂ as eluent, 2-{3-[2-(1-fluoro-1-methylethyl)pyrimidin-4-yl]imidazo[1,2-α]pyrimidin-7-yl}propan-2-ol (27 mg, 61%): ¹H NMR (400 MHz, d⁶-DMSO) δ 10.14 (1H, d, J 7.1), 8.85–8.75 (2H, m), 8.03 (1H, d, J 5.3), 7.68 (1H, d, J 7.1), 7.55 (1H, d, J 5.5), 5.59 (1H, s), 1.83 (6H, d, J 21.6), 1.54 (6H, s); m/z (ES⁺) 316 (M+H⁺).

EXAMPLE 117

2-[3-(2-Isopropylpyrimidin-4-yl)imidazo[1,2-α]pyrimidin-7-yl]propan-2-ol

A mixture of 2-(imidazo[1,2-α]pyrimidin-7-yl)propan-2-ol (Example 21, Step 3) (339 mg, 1.9 mmol), 4-chloro-2-isopropylpyrimidine (300 mg, 1.9 mmol), Cs₂CO₃ (1.25 g, 3.8 mmol) and tetrakis(triphenylphosphine)-palladium(0) (221 mg, 10 mol %) in 1,4-dioxane (10 ml) was heated at 100° C. under N₂ for 18 h. Water (75 ml) was added and the organic products were extracted with CH₂Cl₂ (3×50 ml). The combined organic layers were concentrated under reduced pressure and then purified by column chromatography on silica, using 10% EtOH/EtOAc as eluent, to yield 2-[3-(2-isopropylpyrimidin-4-yl)imidazo[1,2-α]pyrimidin-7-yl]propan-2-ol (121 mg, 22%): ¹H NMR (400 MHz, d⁶-DMSO) δ 10.21 (1H, d, J 8.1), 8.76 (1H, s), 8.72 (1H, d, J 6.1), 7.88 (1H, d, J 6.1), 7.66 (1H, d, J 8.1), 5.57 (1H, s), 3.24 (1H, septet, J 7.7), 1.53 (6H, s), 1.37 (6H, d, J 7.7); m/z (ES⁺) 298 (M+H⁺).

EXAMPLES 118 TO 200

The following compounds were made by methods analogous to those described above.

| Example No. | Z |
|---|---|
| | F₃C-[imidazo[1,2-a]pyrimidine with Z substituent] |
| 118 | 4-methyl-2-(pyridin-4-yl)pyridine |
| 119 | 4-methyl-2-(2,5-difluorophenyl)pyrimidine |
| 120 | 4-methyl-2-(3,4-difluorophenyl)pyridine |
| 121 | 4-methyl-2-(3-chlorophenyl)pyrimidine |

-continued
| Example No. | Z |
|---|---|
| 122 | 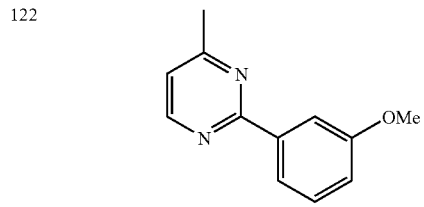 |
| 123 | 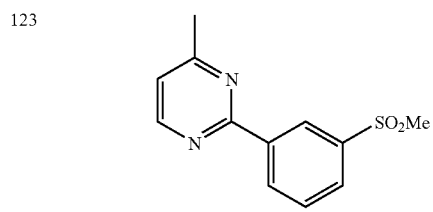 |
| 124 | 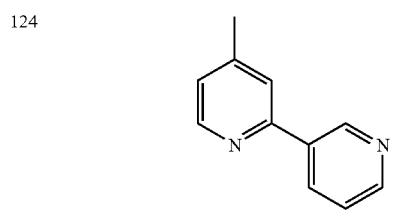 |
| 125 | 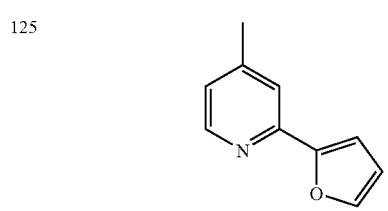 |
| | 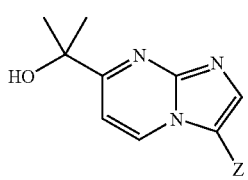 |
| 126 | 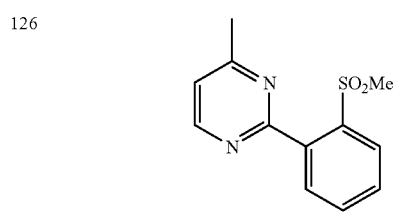 |
| 127 | 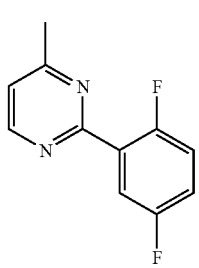 |
-continued
| Example No. | Z |
|---|---|
| 128 | 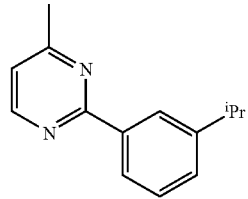 |
| 129 | 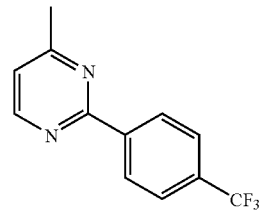 |
| 130 | 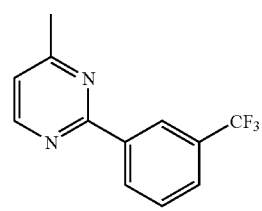 |
| 131 | 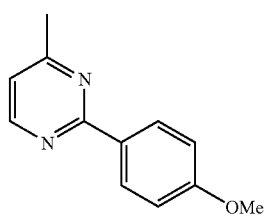 |
| 132 | 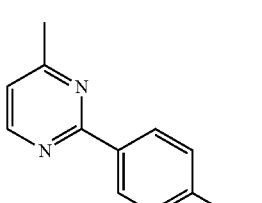 |
| 133 | 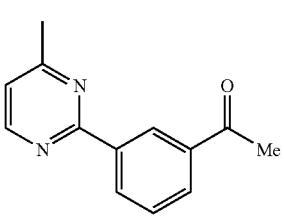 |
| 134 | 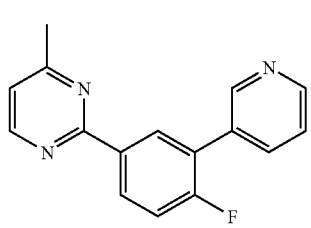 |

-continued
| Example No. | Z |
|---|---|
| 135 | 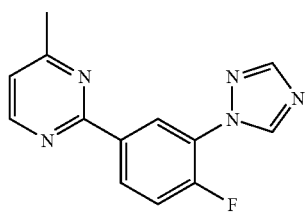 |
| 136 | 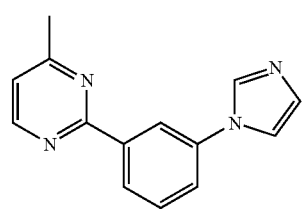 |
| 137 | 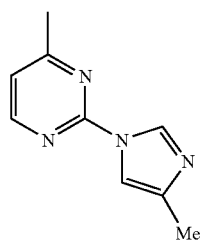 |
| 138 | 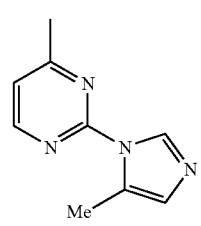 |
| 139 | 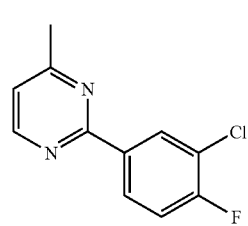 |
| 140 | 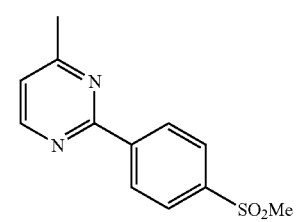 |
| 141 | 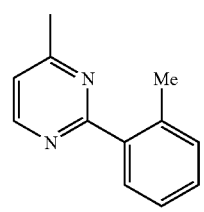 |
-continued
| Example No. | Z |
|---|---|
| 142 | 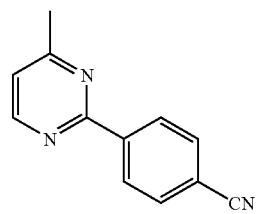 |
| 143 | 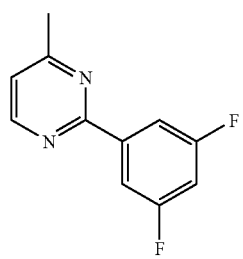 |
| 144 | 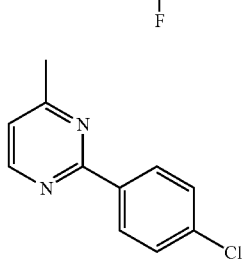 |
| 145 | 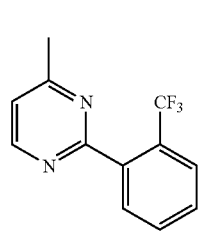 |
| 146 | 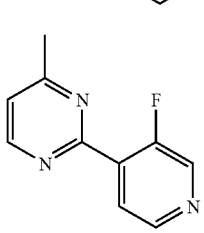 |
| 147 | 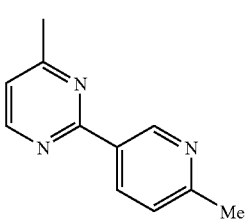 |
| 148 | 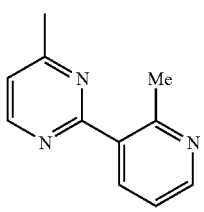 |

| Example No. | Z |
|---|---|
| 149 | 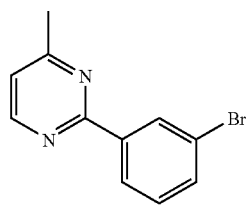 |
| 150 | 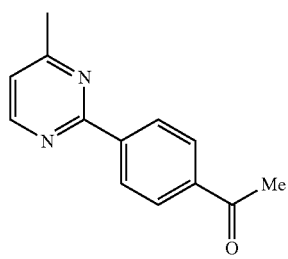 |
| 151 | 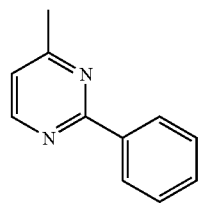 |
| 152 | 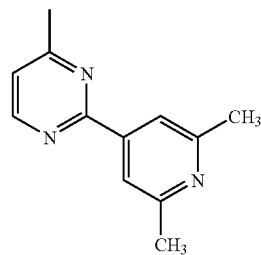 |
| 153 | 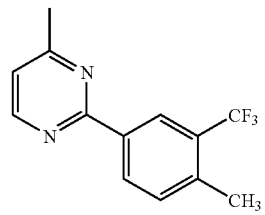 |
| 154 | 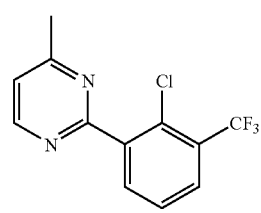 |
| Example No. | Z |
|---|---|
| 155 | 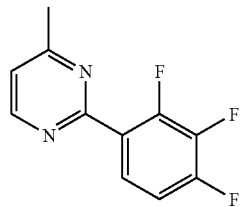 |
| 156 | 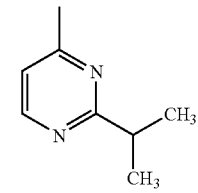 |
| 157 | 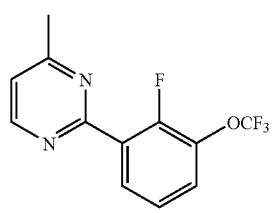 |
| 158 | 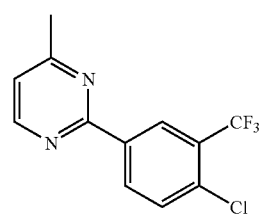 |
| 159 | 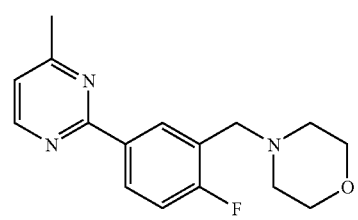 |
| 160 | 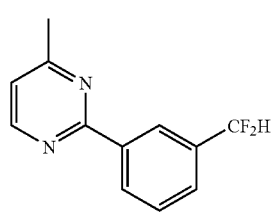 |
| 161 | 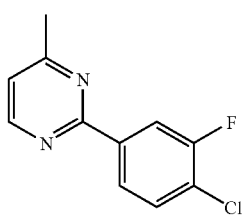 |

-continued
| Example No. | Z |
|---|---|
| 162 | 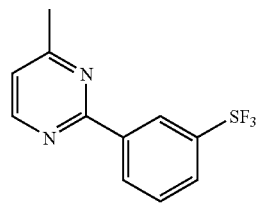 |
| 163 | 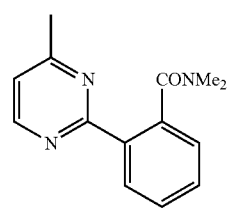 |
| 164 | 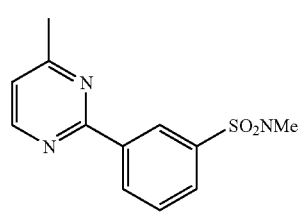 |
| 165 | 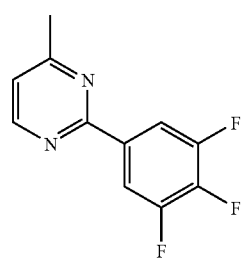 |
| 166 | 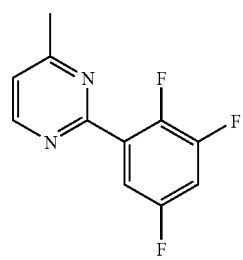 |
| 167 | 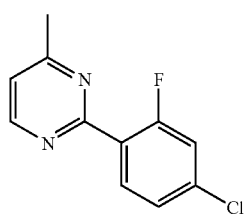 |
-continued
| Example No. | Z |
|---|---|
| 168 | 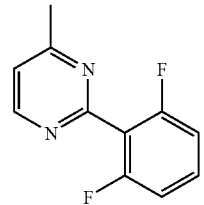 |
| 169 | 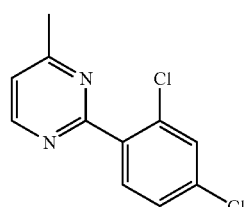 |
| 170 | 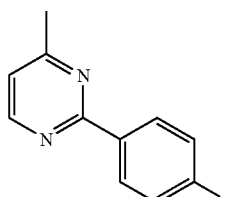 |
| 171 | 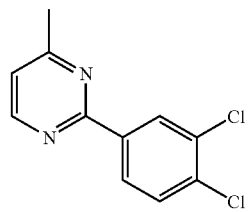 |
| 172 | 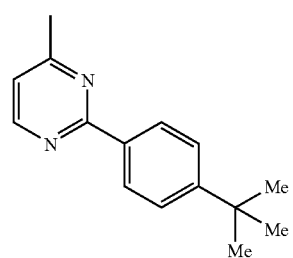 |
| 173 | 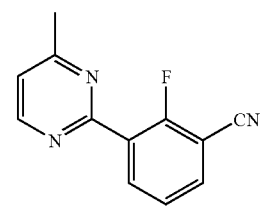 |
| 174 | 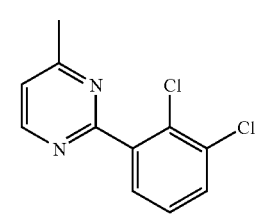 |

-continued
| Example No. | Z |
|---|---|
| 175 | 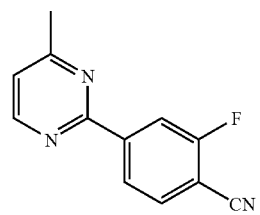 |
| 176 | 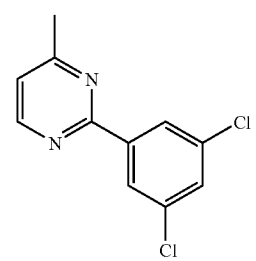 |
| 177 | 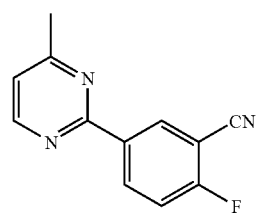 |
| 178 | 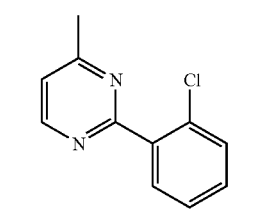 |
| 179 | 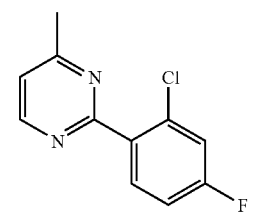 |
| 180 | 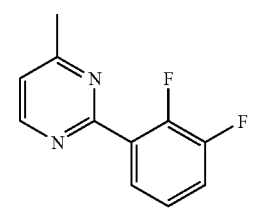 |
-continued
| Example No. | Z |
|---|---|
| 181 | 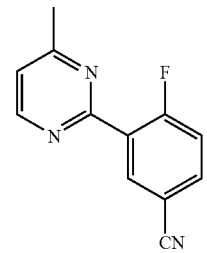 |
| 182 | 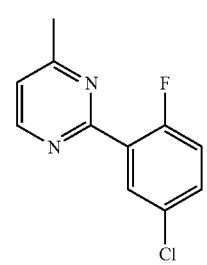 |
| 183 | 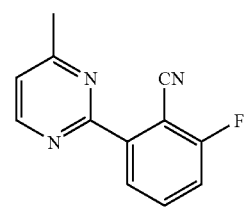 |
| 184 | 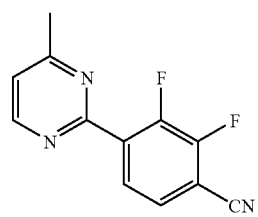 |
| 185 | 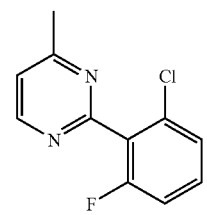 |
| 186 | 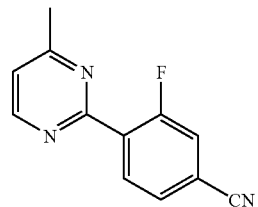 |

-continued
| Example No. | Z |
|---|---|
| 187 | 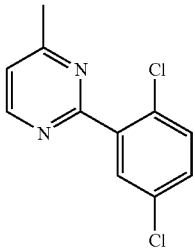 |
| 188 | 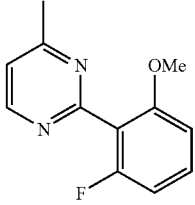 |
| 189 | 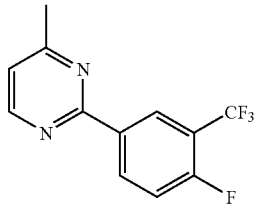 |
| 190 | 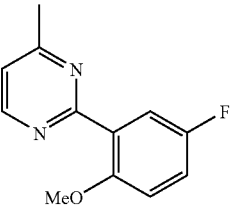 |
| 191 | 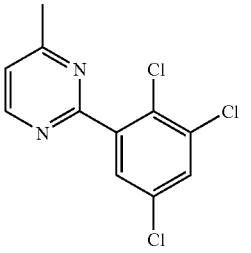 |
| 192 | 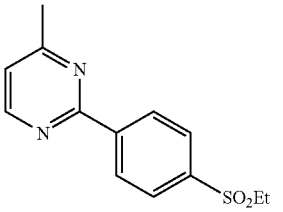 |
-continued
| Example No. | Z |
|---|---|
| 193 | 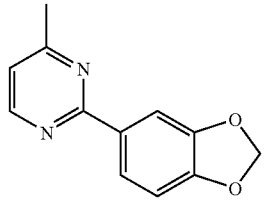 |
| 194 | 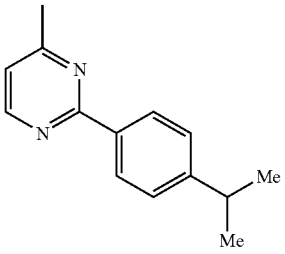 |
| 195 | 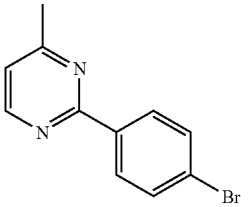 |
| 196 | 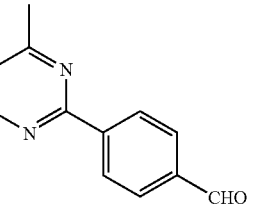 |
| 197 | 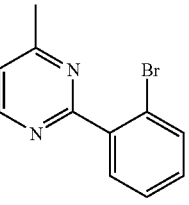 |
| 198 | 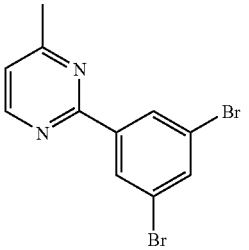 |

-continued

| Example No. | Z |
|---|---|
| 199 | 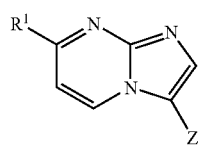 |
| 200 | |

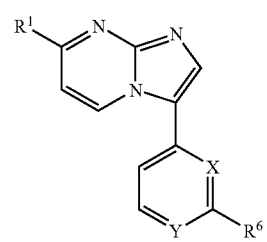

What is claimed is:

1. A compound of formula I, or a pharmaceutically acceptable salt thereof:

(I)

wherein:
Z represents a five-membered heteroaromatic ring selected from furan, thiophene, pyrrole, oxazole, thiazole, isoxazole, isothiazole, imidazole, pyrazole, oxadiazole, thiadiazole, triazole and tetrazole, wherein the ring is unsubstituted or substituted with a substituent selected from the group consisting of: halogen, cyano, trifluoromethyl, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, $C_{3-7}$ cycloalkyl, $C_{3-7}$ heterocycloalkyl, benzyl-tetrahydropyridinyl, $C_{1-6}$ alkoxy, methyltriazolyl($C_{1-6}$)alkoxy, $C_{1-6}$ alkylthio, $C_{1-6}$ alkylsulphonyl, $C_{2-6}$ alkylcarbonyl, amino, $C_{1-6}$ alkylamino, di($C_{1-6}$)alkylamino, $C_{2-6}$ alkylcarbonylamino, phenyl, ($C_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, ($C_{2-6}$)alkylcarbonyl-phenyl, trifluorothio-phenyl, ($C_{1-6}$)alkylsulphonyl-phenyl, di($C_{1-6}$)alklaminocarbonyl-phenyl, di($C_{1-6}$) alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, and methyltetrazolyl-phenyl; or Z represents a six-membered heteroaromatic ring selected from pyridine, pyrazine, pyrimidine and pyridazine, wherein the ring is unsubstituted or substituted with a substituent selected from the group consisting of: halogen, cyano, trifluoromethyl, $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, $C_{3-7}$ cycloalkyl, $C_{3-7}$ heterocycloalkyl, benzyl-tetrahydropyridinyl, $C_{1-6}$ alkoxy, methyltriazolyl($C_{1-6}$)alkoxy, $C_{1-6}$ alkylthio, $C_{1-6}$ alkylsulphonyl, $C_{2-6}$ alkylcarbonyl, amino, $C_{1-6}$ alkylamino, di($C_{1-6}$)alkylamino, $C_{2-6}$ alkylcarbonylamino, phenyl, ($C_{1-6}$)alkyl-phenyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl)phenyl, (halo)(trifluoromethyl)phenyl, nitrophenyl, methoxyphenyl, (halo)(methoxy)phenyl, trifluoromethoxy-phenyl, (halo)(trifluoromethoxy)phenyl, methylenedioxy-phenyl, ($C_{2-6}$)alkylcarbonyl-phenyl, trifluorothio-phenyl, ($C_{1-6}$)alkylsulphonyl-phenyl, di($C_{1-6}$)alkylaminocarbonyl-phenyl, di($C_{1-6}$) alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, and methyltetrazolyl-phenyl;

$R^1$ represents hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, phenyl, phenyl($C_{1-6}$)alkyl, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$, —$CONR^aR^b$ or —$CR^a$=$NOR^b$; and $R^a$ and $R^b$ independently represent hydrogen, $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, phenyl, or phenyl($C_{1-6}$) alkyl.

2. The compound of claim 1 of the formula IIA, or a pharmaceutically acceptable salt thereof:

(IIA)

wherein:
X represents CH and Y represents N; or
X represents N and Y represents CH or N;
$R^6$ represents hydrogen, halogen, cyano, trifluoromethyl, $C_{1-6}$ alkyl, halo($C_{1-6}$)alkyl, dihalo($C_{1-6}$)alkyl, hydroxy ($C_{1-6}$)alkyl, $C_{1-6}$ alkoxy($C_{1-6}$)alkyl, $C_{3-7}$ cycloalkyl, $C_{3-7}$ heterocycloalkyl, benzyl-tetrahydropyridinyl, $C_{1-6}$ alkoxy, methyltriazolyl($C_{1-6}$)alkoxy, $C_{1-6}$ alkylthio, $C_{1-6}$ alkylsulphonyl, $C_{2-6}$ alkylcarbonyl, amino, $C_{1-6}$ alkylamino, di($C_{1-6}$)alkylamino, $C_{2-6}$ alkylcarbonylamino, phenyl, ($C_{1-6}$)alkyl-pheyl, halophenyl, dihalophenyl, trihalophenyl, (fluoro)(methyl)phenyl, cyanophenyl, (cyano)(fluoro)phenyl, (cyano)(difluoro)phenyl, difluoromethyl-phenyl, trifluoromethyl-phenyl, (methyl)(trifluoromethyl) phenyl, (halo)(trifluoromethyl)-phenyl, nitrophenyl, methoxyphenyl, (halo)(methoxy)phenyl, trifluoromethoxy-phenyl, (halo)(trifluoromethoxy)

phenyl, methylenedioxy-phenyl, $(C_{2-6})$alkylcarbonyl-phenyl, trifluorothio-phenyl, $(C_{1-6})$alkylsulphonyl-phenyl, di$(C_{1-6})$alkylaminocarbonyl-phenyl, di$(C_{1-6})$alkylaminosulphonyl-phenyl, (halo)(morpholinylmethyl)phenyl, (halo)(pyridinyl)phenyl, imidazolyl-phenyl, thiadiazolyl-phenyl, methylthiadiazolyl-phenyl, (halo)(triazolyl)phenyl, or methyltetrazolyl-phenyl.

3. The compound of claim 2 of the formula IIB, or a pharmaceutically acceptable salt thereof:

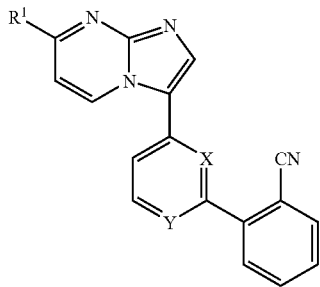

(IIB)

4. The compound of claim 2 of the formula IIC, or a pharmaceutically acceptable salt thereof:

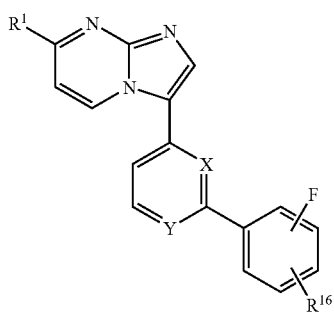

(IIC)

wherein:
$R^{16}$ represents hydrogen, fluoro or cyano.

5. A compound which is selected from:
3-(6-bromopyridin-2-yl)-7-trifluoromethylimidazo[1,2-α]pyrimidine;
2-[6-(7-trifluoromethylimidazo[1,2-α]pyrimidin-3-yl)pyridin-2-yl]-benzonitrile;
2-[4-(7-trifluoromethylimidazo[1,2α]pyrimidin-3-yl)pyridin-2-yl]-benzonitrile;
3-(3-chloromethyl-[1,2,4]thiadiazol-5-yl)-7-trifluoromethylimidazo[1,2-α]pyrimidine;
3-(2-chloropyrimidin-4-yl)-7-trifluoromethylimidazo[1,2-α]pyrimidine;
3(thiazol-2-yl)-7-trifluoromethylimidazo[1,2-α]pyrimidine;
6-(7-trifluoromethylimidazo[1,2-α]pyrimidin-3-yl) nicotinonitrile;
3-(pyridin-2-yl)-7-trifluoromethylimidazo[1,2-α]pyrimidine;
3-[6-(pyrrolidin-1-yl)pyridin-2-yl]-7-trifluoromethylimidazo[1,2-α]pyrimidine;
7-trifluoromethyl-3-(6-trifluoromethylpyridin-2-yl)imidazo[1,2-α]pyrimidine;
3-(6-methylpyridin-2-yl)-7-trifluoromethylimidazo[1,2-α]pyrimidine;
3(6-methoxypyridin-2-yl)-7-trifluoromethylimidazo[1,2-α]pyrimidine;
3-(6-cyclopentylpyridin-2-yl)-7-trifluoromethylimidazo[1,2-α]pyrimidine;
3-(5-methylpyridin-2-yl)-7-trifluoromethylimidazo[1,2-α]pyrimidine;
7-trifluoromethyl-3-(5-trifluoromethylpyridin-2-yl)imidazo[1,2-α]pyrimidine;
2-[4-(7-trifluoromethylimidazo[1,2-α]pyrimidin-3-yl)pyrimidin-2-yl]benzonitrile;
3-[3-(thien-2-yl)-[1,2,4]thiadiazol-5-yl]-7trifluoromethylimidazo[1,2-α]pyrimidine;
3-[4-(pyridin-3-yl)thien-2-yl]-7-trifluoromethylimidazo[1,2-α]pyrimidine;
3-[5-(pyridin-3-yl)thien-3-yl]-7-trifluoromethylimidazo[1,2-α]pyrimidine;
3-[4-(pyridin-3-yl)thiazol-2-yl]-7-trifluoromethylimidazo[1,2-α]pyrimidine;
and pharmaceutically acceptable salts thereof.

6. A compound which is selected from:
2-{6-[7-(1-hydroxy-1-methylethyl)imidazo[1,2-α]pyrimidin-3-yl]pyridin-2-yl}benzonitrile;
5-fluoro-2-{6-[7-(1-hydroxy-1-methylethyl)imidazo[1,2-α]pyrimidin-3-yl]pyridin-2-yl}benzonitrile;
3-{6-[7-(1-hydroxy-1-methylethyl)imidazo[1,2-α]pyrimidin-3-yl]pyridin-2-yl) thiophene-2-carbonitrile;
4-fluoro-2-{6-[7-(1-hydroxy-1-methylethyl)imidazo[1,2-α]pyrimidin-3-yl]pyridin-2-yl}benzonitrile;
3-(6-bromopyridin-2-yl)-7-(1-fluoro-1-methylethyl)imidazo[1,2-α]pyrimidine;
2-{6-[7-(1-fluoro-1-methylethyl)imidazo[1,2-α]pyrimidin-3-yl]pyridin-2-yl}benzonitrile;
2-{6-[7-(1-cyano-1-methylethyl)imidazo[1,2-α]pyrimidin-3-yl]pyridin-2-yl}benzonitrile;
2-[6-(7-tert-butylimidazo[1,2-α]pyrimidin-3-yl)pyridin-2-yl]-5-fluorobenzonitrile;
4-fluoro-2-[6-(7-trifluoromethylimidazo[1,2-α]pyrimidin-3-yl)pyridin-2-yl]benzonitrile;
3-(2-fluoropyridin-5-yl)-7-trifluoromethylimidazo[1,2-α]pyrimidine;
3-(2-phenylpyridin-5-yl)-7-trifluoromethylimidazo[1,2-α]pyrimidine;
3-[2-(4-fluoropheny)pyridin-5-yl)]-7-trifluoromethylimidazo[1,2-α]pyrimidine;
3-[2-(1H-pyrrol-1-yl)pyridin-5-yl]-7-trifluoromethylimidazo[1,2-α]pyrimidine;
3-(2-chloropyrimidin-4-yl)-7-(1-hydroxy-1-methylethyl)imidazo[1,2-α]pyrimidine;
5-fluoro-2-{4-[7-(1-hydroxy-1-methylethyl)imidazo[1,2-α]pyrimidin-3-yl]-pyrimidin-2-yl)benzonitrile;
2-[3-(2-(pyridin-3-yl)pyrimidin-4-yl)imidazo[1,2-α]pyrimidin-7-yl]propan-2-ol;
2-{4-[7-(1-hydroxy-1-methylethyl)imidazo[1,2-α]pyrimidin-3-yl]pyrimidin-2-yl)thiophene-3-carbonitrile;
5-fluoro-2-{4-[7-trifluoromethylimidazo[1,2-α]pyrimidin-3-yl]pyrimidin-2-yl)benzonitrile;
2-[3-(2-trifluoromethylpyrimidin-4-yl)imidazo[1,2-α]pyrimidin-7-yl]propan-2-ol;
2-[3-(2-(thiazol-2-yl)pyrimidin-4-yl)imidazo[1,2-α]pyrimidin-7-yl]propan-2-ol;
2-[3-(2-(imidazol-1-yl)pyrimidin-4yl)imidazo[1,2-α]pyrimidin-7-yl]propan-2-ol;
2-[3-(2(pyridin-4-yl)pyrimidin-4-yl)imidazo[1,2-α]pyrimidin-7-yl]propan-2-ol
2-[3(2-(furan-2-yl)pyrimidin-4-yl)imidazo[1,2-α]pyrimidin-7-yl]propan-2ol;
2-[3-(2-(furan-3-yl)pyrimidin-4-yl)imidazo[1,,2-α]pyrimidin-7-yl]propan-2-ol;
2-{3-[2-(1-oxypyridin-4-yl)pyrimidin-4-yl]imidazo[1,2-α]pyrimidin-7-yl}propan-2-ol;
3-[6-(1H-imidazol-1-yl)pyridin-2-yl]-7-trifluoromethylimidazo[1,2-α]pyrimidine;

3-[6-(morpholin-4-yl)pyridin-2-yl]-7-trifluoromethylimidazo[1,2-α]pyrimidine;
3-(6-phenylpyridin-2-yl)-7-trifluoromethylimidazo[1,2-α]pyrimidine;
6-(7-trifluoromethylimidazo[1,2-α]pyrimidin-3-yl)-2,3'-bipyridine;
N-[6-(7-trifluoromethylimidazo[1,2-α]pyrimidin-3-yl)pyridin-2-yl]acetamide;
N-(tert-butyl)-6-(7-trifluoromethylimidazo[1,2-α]pyrimidin-3-yl)pyridin-2-ylamine;
3-[6-(1H-[1,2,4]triazol-1-yl)pyridin-2-yl]-7-trifluoromethylimidazo[1,2-α]pyrimidine;
3-[6-(isothiazol-4-yl)pyridin-2-yl]-7-trifluoromethylimidazo[1,2-α]pyrimidine;
3-(6-isopropoxypyridin-2-yl)-7-trifluoromethylimidazo[1,2-α]pyrimidine;
3-(6-ethoxypyridin-2-yl)-7-trifluoromethylimidazo[1,2-α]pyrimidine;
6-(7-trifluoromethylimidazo[1,2-α]pyrimidin-3-yl)-2,2'-bipyridine;
6-(7-trifluoromethylimidazo[1,2-α]pyrimidin-3-yl)-2,4'-bipyridine;
3-(6-methoxymethylpyridin-2-yl)-7trifluoromethylimidazo[1,2-α]pyrimidine;
3-[6-(thien-3-yl)pyridin-2-yl]-7-trifluoromethylimidazo[1,2-α]pyrimidine;
7-(1,1-dimethoxyethyl)-3-[2-(pyridin-4-yl)pyrimidin-4-yl]imidazo[1,2-α]pyrimidine;
2-{3-[2-(3-nitrophenyl)pyrimidin-4-yl]imidazo[1,2-α]pyrimidin-7-yl}propan-2-ol;
2-{3-[2-(3-fluorophenyl)pyrimidin-4-yl]imidazo[1,2-α]pyrimidin-7-yl}propan-2-ol;
1-[3-(2-(pyridin-4-yl)pyrimidin-4-yl)imidazo[1,2-α]pyrimidin-7-yl]ethanone;
6-[7-([1,2,4]triazol-1-ylmethyl)imidazo[1,2-α]pyrimidinyl-3-yl]-2,3'bipyridine;
2-[6-(7-([1,2,4]triazol-1-ylmethyl)imidazo[1,2-α]pyrimidin-3-yl)pyridin-2-yl]benzonitrile;
6'-(7-trifluoromethylimidazo[1,2-α]pyrimidin-3-yl)-2,2'-bipyridinyl-3-carbonitrile;
6'-[7-(1-fluoro-1-methylethyl)imidazo[1,2-α]pyrimidin-3-yl]-2,2'-bipyridinyl-3-carbonitrile;
and pharmaceutically acceptable salts thereof.

7. A compound which is selected from:
2-{3-[2-(2,4-difluorophenyl)pyrimidin-4-yl]imidazo[1,2-α]pyrimidin-7-yl}propan-2-ol;
2-{3-[2-(3,4-difluorophenyl)pyrimidin-4-yl)imidazo[1,2-α]pyrimidin-7-yl}propan-2-ol;
2-{3-[2-(1-benzyl-1,2,3,6-tetrahydropyridin-4-yl)pyrimidin-4-yl]imidazo[1,2-α]pyrimidin-7-yl}propan-2-ol;
2-{3-[2-(1,1-difluoroethyl)pyrimidin-4-yl]imidazo[1,2-α]pyrimidin-7-yl}propan-2-ol;
1-{4-[7-(1-hydroxy-1-methylethyl)imidazo[1,2-α]pyrimidin-3-yl]pyrimidin-2-yl}ethanone;
2-{3-[2-(1-hydroxy-1-methylethyl)pyrimidin-4-yl]imidazo[1,2-α]pyrimidin-7yl}propan-2-ol;
2-{3-[2-(1-fluoro-1-methylethyl)pyrimidin-4-yl]imidazo[1,2-α]pyrimidin-7-yl}propan-2-ol;
2-[3-(2-isopropylpyrimidin-4-yl)imidazo[1,2-α]pyrimidin-7-yl]propan-2-ol; and pharmaceutically acceptable salts thereof.

8. A pharmaceutical composition comprising a compound of claim 1, or a pharmaceutically acceptable salt thereof and a pharmaceutically acceptable carrier.

9. A method for the treatment of anxiety which comprises administering to a patient is need of such treatment an effective amount of a compound of claim 1, or a pharmaceutically acceptable salt thereof.

10. A process for the preparation of the compound of claim 1, which comprises:

(A) reacting a compound of formula III with a compound of formula IV:

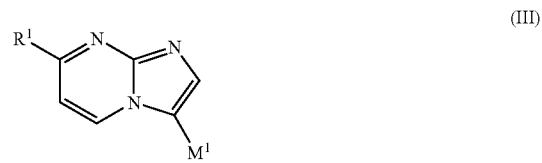

(III)

L¹—Z  (IV)

wherein Z and R¹ are as defined in claim 1, L¹ represents a suitable leaving group, and M¹ represents a boronic acid moiety —B(OH)₂ or a cyclic ester thereof formed with an organic diol, or M¹ represents —Sn(Alk)₃ in which Alk represents C$_{1-6}$ alkyl; in the presence of a transition metal catalyst; or (B) reacting a compound of formula V with a compound of formula VI:

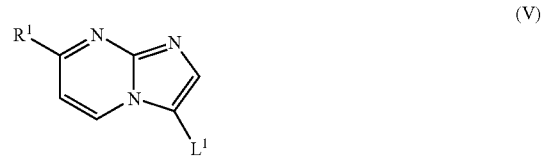

(V)

M¹—Z  (VI)

M¹—Z  (VI)

wherein Z and R¹ are as defined in claim 1, and L¹ and M¹ are as defined above; in the presence of a transition metal catalyst; or (C) reacting a compound of formula VII with a compound of formula VIII:

(VII)

(VIII)

wherein R¹ is defined in claim 1, R⁷ represents any allowable substituent on the group Z, and Hal represents a halogen atom; or (D) reacting a compound of formula XV with a compound of formula XVI:

R$^{1a}$—M¹  (XV)

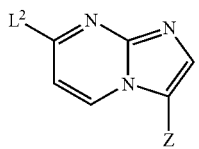

(XVI)

wherein Z is as defined in claim 1, $M^1$ is as defined above, $R^{1a}$ represents an aryl or heteroaryl moiety, and $L^2$ represents a suitable leaving group; in the presence of a transition metal catalyst; or (E) reacting a compound of formula IV as defined above with a compound of formula IX:

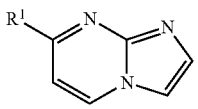

(IX)

wherein $R^1$ is as defined in claim 1; in the presence of a transition metal catalyst.

* * * * *